United States Patent
Sheinerman et al.

(10) Patent No.: US 10,781,487 B2
(45) Date of Patent: Sep. 22, 2020

(54) MIRNA-BASED METHODS FOR DETECTING AND MONITORING AGING

(71) Applicant: DiamiR, LLC, Princeton, NJ (US)

(72) Inventors: Kira S. Sheinerman, New York, NY (US); Vladimir G. Tsivinsky, Sharon, MA (US); Samuil R. Umansky, Princeton, NJ (US)

(73) Assignee: DIAMIR, LLC, Princeton, NJ (US)

( * ) Notice: Subject to any disclaimer, the term of this patent is extended or adjusted under 35 U.S.C. 154(b) by 0 days.

(21) Appl. No.: 16/044,279

(22) Filed: Jul. 24, 2018

(65) Prior Publication Data

US 2019/0024169 A1  Jan. 24, 2019

Related U.S. Application Data

(60) Provisional application No. 62/536,320, filed on Jul. 24, 2017.

(51) Int. Cl.
| | | |
|---|---|---|
| *A61K 48/00* | (2006.01) | |
| *C07H 21/04* | (2006.01) | |
| *C12Q 1/6876* | (2018.01) | |
| *C12Q 1/6883* | (2018.01) | |

(52) U.S. Cl.
CPC ......... *C12Q 1/6876* (2013.01); *C12Q 1/6883* (2013.01); *C12Q 2600/178* (2013.01)

(58) Field of Classification Search
CPC .......................... C12N 2310/14; C12N 15/113
See application file for complete search history.

(56) References Cited

U.S. PATENT DOCUMENTS

| | | |
|---|---|---|
| 4,785,507 A | 11/1988 | Miyazaki et al. |
| 4,829,304 A | 5/1989 | Baird |
| 4,939,663 A | 7/1990 | Baird |
| 7,653,509 B2 | 1/2010 | Bagwell |
| 7,897,356 B2 | 3/2011 | Klass et al. |
| 7,993,831 B2 | 8/2011 | Latham et al. |
| 8,486,626 B2 | 7/2013 | Umansky et al. |
| 8,632,967 B2 | 1/2014 | Kuroda et al. |
| 8,648,017 B2 | 2/2014 | Umansky et al. |
| 9,447,471 B2 | 9/2016 | Qu et al. |
| 9,540,692 B2 | 1/2017 | Xu |
| 9,605,315 B2 | 3/2017 | Patel et al. |
| 9,611,511 B2 | 4/2017 | Keller et al. |
| 9,708,667 B2 | 7/2017 | Yanai et al. |
| 9,726,676 B2 | 8/2017 | Grabe et al. |
| 9,790,554 B2 | 10/2017 | Keller et al. |
| 9,803,242 B2 | 10/2017 | Umansky et al. |
| 9,809,857 B2 | 11/2017 | Wang |
| 9,933,440 B2 | 4/2018 | Goetzl |
| 2007/0161004 A1 | 7/2007 | Brown et al. |
| 2008/0020390 A1 | 1/2008 | Mitchell et al. |
| 2008/0139801 A1 | 6/2008 | Umansky et al. |
| 2008/0171667 A1 | 7/2008 | Brown et al. |
| 2009/0004668 A1 | 1/2009 | Chen et al. |
| 2009/0075258 A1 | 3/2009 | Latham et al. |
| 2009/0081640 A1 | 3/2009 | Umansky et al. |
| 2009/0176723 A1 | 7/2009 | Brown et al. |
| 2010/0151480 A1 | 6/2010 | Taylor et al. |
| 2010/0167937 A1 | 7/2010 | Goldknopf et al. |
| 2010/0167948 A1 | 7/2010 | Krichevsky et al. |
| 2010/0184046 A1 | 7/2010 | Klass et al. |
| 2010/0196426 A1 | 8/2010 | Skog et al. |
| 2010/0216139 A1 | 8/2010 | Galas et al. |
| 2010/0227908 A1 | 9/2010 | Cairns |
| 2010/0267804 A1 | 10/2010 | Port et al. |
| 2010/0279292 A1 | 11/2010 | Marsh et al. |
| 2010/0286044 A1 | 11/2010 | Litman et al. |
| 2010/0323357 A1 | 12/2010 | Nana-Sinkam et al. |
| 2011/0003704 A1 | 1/2011 | Skog et al. |
| 2011/0053157 A1 | 3/2011 | Skog et al. |
| 2011/0053158 A1 | 3/2011 | Mambo et al. |
| 2011/0086348 A1 | 4/2011 | Prasad et al. |
| 2011/0111976 A1 | 5/2011 | Fare et al. |
| 2011/0117111 A1 | 5/2011 | Kwon et al. |
| 2011/0117560 A1 | 5/2011 | Spinale et al. |
| 2011/0143360 A1 | 6/2011 | Kuroda et al. |
| 2011/0160285 A1 | 6/2011 | Anderson et al. |
| 2011/0160290 A1 | 6/2011 | Tewari |
| 2012/0034608 A1 | 2/2012 | Zhou et al. |
| 2012/0093936 A1 | 4/2012 | Lindenberg et al. |
| 2012/0184599 A1 | 7/2012 | Marcet et al. |
| 2012/0252693 A1 | 10/2012 | Umansky et al. |
| 2012/0270746 A1 | 10/2012 | Kuroda et al. |
| 2013/0012403 A1 | 1/2013 | Hu |
| 2013/0131194 A1 | 5/2013 | Skog et al. |
| 2014/0120545 A1 | 5/2014 | Umansky et al. |

(Continued)

FOREIGN PATENT DOCUMENTS

| | | |
|---|---|---|
| CN | 101942502 A | 1/2011 |
| CN | 101962685 A | 2/2011 |

(Continued)

OTHER PUBLICATIONS

Harman (Ann NY Acad Sci, 2002, 959, 384-395).*
Cogwell et al. (Journal of Alzheimer's Disease, 14, 2008, 27-41).*
Osmanovic-Barilar et al. (Drugs Aging, 2016, 33, 787-808).*
Chinese Office Action dated Mar. 26, 2019, which issued during prosecution of Chinese Application No. 201480073413.0, 8 pages total.
Chinese Office Action dated Mar. 25, 2019, which issued during prosecution of Chinese Application No. 201610344816.5, 13 pages total.
Canadian Communication received for Canadian Patent Application No. 2,780,222 dated Jan. 28, 2019, 5 pages total.
Canadian Communication received for Canadian Patent Application No. 2,833,375, dated Oct. 12, 2018, 7 pages total.

(Continued)

*Primary Examiner* — Amy H Bowman
(74) *Attorney, Agent, or Firm* — Troutman Pepper Hamilton Sanders LLP

(57) ABSTRACT

The present invention is directed to methods for detection, treatment monitoring, and slowing of aging by quantifying miRNAs in bodily fluids.

18 Claims, 36 Drawing Sheets

(56) References Cited

U.S. PATENT DOCUMENTS

| | | | |
|---|---|---|---|
| 2014/0170648 A1 | 6/2014 | Kuroda et al. | |
| 2014/0194319 A1 | 7/2014 | Skog et al. | |
| 2014/0194613 A1 | 7/2014 | Skog et al. | |
| 2014/0256562 A1 | 9/2014 | Umansky et al. | |
| 2014/0259192 A1* | 9/2014 | Saarma .............. | A01K 67/0276 800/12 |
| 2014/0357507 A1 | 12/2014 | Umansky et al. | |
| 2015/0005365 A1 | 1/2015 | Zakharenko et al. | |
| 2016/0273043 A1 | 9/2016 | Umansky et al. | |
| 2017/0107575 A1 | 4/2017 | Umansky et al. | |
| 2017/0362656 A1 | 12/2017 | Umansky et al. | |

FOREIGN PATENT DOCUMENTS

| | | | |
|---|---|---|---|
| EP | 2699666 B1 | 2/2014 | |
| EP | 2699697 A1 | 2/2014 | |
| EP | 2496714 B1 | 8/2016 | |
| EP | 3071712 | 9/2016 | |
| EP | 3118334 A1 | 1/2017 | |
| EP | 3133147 A1 | 2/2017 | |
| JP | 2010536372 A | 12/2010 | |
| JP | 2010538653 A | 12/2010 | |
| JP | 5624470 B2 | 11/2014 | |
| RU | 2367959 C1 | 9/2009 | |
| WO | 2005118806 A2 | 12/2005 | |
| WO | 2007073737 A1 | 7/2007 | |
| WO | 2008045505 A2 | 4/2008 | |
| WO | 2008153692 A2 | 12/2008 | |
| WO | 2009009457 A1 | 1/2009 | |
| WO | 2009012468 A2 | 1/2009 | |
| WO | 2009015357 A1 | 1/2009 | |
| WO | 2009025852 A2 | 2/2009 | |
| WO | 2009036236 A1 | 3/2009 | |
| WO | 2009070653 A1 | 6/2009 | |
| WO | 2009100029 A1 | 8/2009 | |
| WO | 2009114681 A2 | 9/2009 | |
| WO | 2009120877 A2 | 10/2009 | |
| WO | 2009132273 A2 | 10/2009 | |
| WO | 2009133915 A1 | 11/2009 | |
| WO | 2009143379 A2 | 11/2009 | |
| WO | WO 2009/147519 A1 * | 12/2009 | ........... A61K 31/713 |
| WO | 2010054386 A2 | 5/2010 | |
| WO | 2010117829 A2 | 10/2010 | |
| WO | 2011015720 A1 | 2/2011 | |
| WO | 2011057003 A2 | 5/2011 | |
| WO | 2012145363 A1 | 10/2012 | |
| WO | 2012145409 A1 | 10/2012 | |
| WO | 2013036936 A1 | 3/2013 | |
| WO | 2015073972 A1 | 5/2015 | |
| WO | 2015164431 A2 | 10/2015 | |
| WO | 2017120285 A1 | 7/2017 | |
| WO | 2017165458 A1 | 9/2017 | |
| WO | WO 2017/161256 A1 * | 9/2017 | ........... A61K 31/713 |

OTHER PUBLICATIONS

Canadian Communication received for Canadian Patent Application No. 2,833,389, dated Oct. 18, 2018, 3 pages total.
European Communication (Article 94(3) EPC) received for European Application No. 14862355.6, dated Jan. 22, 2019, 8 pages total.
Japanese Communication (First Office Action) received for Japanese Patent Application No. 2017-174778, dated Nov. 16, 2018, 21 pages total.
Japanese Communication received for Japanese Patent Application No. 2016-532043, dated Oct. 2, 2018, 17 pages total.
Sheinerman, K.S. et al., "Circulating Brain-Enriched MicroRNAs as Novel Biomarkers for Detection and Differentiation of Neurodegenerative Diseases" Alzheimer's Research & Therapy (2017) vol. 9, No. 89, 13 pages total.
Final Office Action received for U.S. Appl. No. 15/606,747, dated Dec. 26, 2018, 40 pages.
Non-Final Office Action received for U.S. Appl. No. 15/390,110, dated Sep. 25, 2018, 30 pages.
Final Office Action received for U.S. Appl. No. 13/508,262, dated Jul. 30, 2013, 10 pages.
Final Office Action received for U.S. Appl. No. 14/112,684, dated Apr. 28, 2016, 19 pages.
Final Office Action received for U.S. Appl. No. 14/112,765, dated Oct. 9, 2015, 18 pages.
Final Office Action received for U.S. Appl. No. 15/037,559, dated Apr. 18, 2018, 26 pages.
Geekiyanage, H. et al., "Blood serum miRNA: Non-invasive biomarkers for Alzheimer's disease" Exp Neurol. (2011) vol. 235, pp. 491-496, ePub Dec. 1, 2011.
Gene Cards entry for MIR146A, retrieved from https://www.genecards.org/cgi-bin/carddisp.pl?gene=MIR146A&Keywords=mir146 on Apr. 14, 2018, 11 pages total.
Gillardon, F. et al. "MicroRNA and proteome expression profiling in early-symptomatic α-synuclein(A30P)-transgenic mice" Proteomics Clinical Application (2008) vol. 2, No. 5, pp. 697-705.
Goetz, C.G. "The History of Parkinson's Disease: Early Clinical Descriptions and Neurological Therapies" Cold Spring Harbor Perspect Med. (2011) vol. 1, a008862.
Griffiths-Jones, S. et al., "miRBase: microRNA sequences, targets and gene nomenclature" Nucleic Acids Research (2006) vol. 34, Database issue: D140-D144.
Hebert, S.S. et al. "Alterations of the microRNA network cause neurodegenerative disease" Trends in Neurosciences (2009) vol. 32, No. 4, pp. 199-206.
Hebert, S.S. et al., "Loss of microRNA cluster miR-29a/b-1 in sporadic Alzheimer's disease correlates with increased BACEI/beta-secretase expression" Proc Natl Acad Sci USA (2008) vol. 105, pp. 6415-6420.
Henriksen, K. et al., "The future of blood-based biomarkers for Alzheimer's disease" Alzheimer's & Dementia (2014) vol. 10, pp. 115-131.
Hua, D. et al., "A Catalogue of Glioblastoma and Brain MicroRNAs Identified by Deep Sequencing" OMICS A of Journal Integrative Biology (2012) vol. 16, No. 12, pp. 690-699.
Hua, Y-J. et al., "Identification and target prediction of miRNAs specifically expressed in rat neural tissue" BMC Genomics (2009) vol. 10, pp. 214-225.
Hunter, M.P. et al., "Detection of microRNA Expression in Human Peripheral Blood Microvesicles" PLoS One (2008) vol. 3, No. 11, e3694.
International Preliminary Report on Patentability for International Appl. No. PCT/US2010/055495, dated May 8, 2012, 14 pages total.
International Preliminary Report on Patentability issued in PCT/US2012/034098 dated Oct. 22, 2013, 15 pages total.
International Preliminary Report on Patentability received for PCT Patent Application No. PCT/US2012/034025, dated Oct. 31, 2013, 9 pages.
International Preliminary Report on Patentability received for PCT Patent Application No. PCT/US2014/065959, dated May 24, 2016, 15 pages.
International Preliminary Report on Patentability received for PCT Patent Application No. PCT/US2017/012258, dated Jul. 10, 2018, 12 pages.
International Search Report and Written Opinion for International Appl. No. PCT/US2010/055495, dated Jun. 6, 2011, 20 pages total.
International Search Report and Written Opinion of the International Searching Authority for International Application No. PCT/US2012/034025, dated Sep. 28, 2012, 14 pages total.
International Search Report and Written Opinion of the International Searching Authority for International Application No. PCT/US2012/034098, dated Jul. 17, 2012, 16 pages total.
International Search Report and Written Opinion of the International Searching Authority dated Apr. 28, 2015 issued during prosecution of International Application No. PCT/US2014/065959, 17 pages total.
International Search Report and Written Opinion of the International Searching Authority dated May 8, 2017 issued during prosecution of International Application No. PCT/US2017/012258, 14 pages total.

(56) References Cited

OTHER PUBLICATIONS

International Search Report and Written Opinion of the International Searching Authority for International Application No. PCT/US2017/23470, dated Jul. 31, 2017, 24 pages total.
Issler, O. et al., "Determining the Role of MicroRNAs in Psychiatric Disorders" Nature Reviews Neuroscience (2015) vol. 16, pp. 201-212.
Japanese Office Action issued in Japanese Patent Application No. 2014-506501 dated Mar. 16, 2016 (and English-language translation thereof), 15 pages.
Japanese Office Action issued in Japanese Patent Application No. 2014-506516 dated Apr. 4, 2016 (and English-language translation thereof), 20 pages.
Japanese Office Action issued in Japanese Patent Application No. 2014-506516 dated Mar. 1, 2017, 10 pages total.
Ji, X. et al., "Plasma miR-208 as a Biomarker of Myocardial Injury" Clinical Chemistry (2009) vol. 55, No. 11, pp. 1944-1949.
Kemppainen, et al., "MicroRNAs as biomarkers in blood and other biofluids, poster 2010?" [Retrieved from the Internet Sep. 8, 2012: <http://www.asuragen.comipdfs/postersibiomarkers.pdf>].
Koirala S. et al., "Pruning an Axon Piece by Piece" Neuron (2004) vol. 44, pp. 578-580.
Kosaka, N. et al., "Circulating microRNA in body fluid: a new potential biomarker for cancer diagnosis and prognosis" Cancer Sci. (2010) vol. 101, No. 10, pp. 2087-2092.
Kosaka, N. et al., "Secretory Mechanisms and Intercellular Transfer of MicroRNAs in Living Cells" J Biol Chem. (2010) vol. 285, No. 23, pp. 17442-17452.
Kroh, E.M. et al., "Analysis of Circulating MircoRNA Biomarkers in Plasma and Serum Using Quantitative Reverse Transcription-PCR (qRT-PCR)" Methods (2010) vol. 50, pp. 298-301.
Kye, M.J. et al., "Somatodendritic microRNAs identified by laser capture and multiplex RT-PCR" RNA (2007) vol. 13, pp. 1224-1234.
Landgraf, P., "A Mammalian microRNA Expression Atlas Based on Small RNA Library Sequencing" Cell (2007) vol. 129, No. 7, pp. 1401-1414.
Laterza, O.F. et al., "Plasma MicroRNAs as Diagnostically Sensitive and Specific Biomarkers of Tissue Injury" Clinical Chemistry (2009) vol. 55, No. 11, pp. 1-7.
Lee, E.J. et al., "Systematic evaluation of microRNA processing patterns in tissues, cell lines, and tumors" RNA (2008) vol. 14, pp. 35-42.
Liang, Y. et al., "Characterization of microRNA expression profiles in normal human tissues" BMC Genomics (2007) vol. 8, pp. 166-185.
Liang, Y. "An expression meta-analysis of predicated microRNA targets identifies a diagnostic signature for lung cancer" BMC Med. Genomics (2008) vol. 1, No. 61, pp. 1-16.
Lin, A-L. et al., "Multimodal MRI Neuroimaging Biomarkers for Cognitive Normal Adults, Amnestic Mild Cognitive Impairment, and Alzheimer's Disease" Neurology Research International vol. 2012, Article ID 907409, 17 pages.
Lindner, K. et al. "Circulating microRNAs: emerging biomarkers for diagnosis and prognosis in patients with gastrointestinal cancers" Clinical Science (2015) vol. 128, pp. 1-15.
Liu, D-Z. et al., "Brain and blood microRNA expression profiling of ischemic stroke, intracerebral hemorrhage, and kainate seizures" J Cereb Blood Flow Metab., advance online publication (2009) doi:10.1038/jcbfm.2009, vol. 186, pp. 1-10.
Liu, R. et al., "A Five-microRNA Signature Identified from Genome-wide Serum microRNA Expression Profiling Serves as a Fingerprint for Gastric Cancer Diagnosis" European Journal of Cancer (2011) vol. 47, pp. 784-791.
Lodes, M. J. et al., "Detection of Cancer with Serum miRNAs on an Oligonucleotide Microarray" PLoS One (2009) vol. 4, No. 7, e6229.
Londin, E. et al., "Analysis of 13 cell types reveals evidence for the expression of numerous novel primate- and tissue-specific microRNAs" Proc. Natl. Acad. Sci. USA (2015) E1106-E1115.
Low, L.K. et al., "Axon pruning: an essential step underlying the developmental plasticity of neuronal connections" Phil Trans R Soc B. (2006) vol. 361, pp. 1531-1544.
Lugli, G. et al., "Expression of microRNAs and their precursors in synaptic fractions of adult mouse forebrain" Journal of Neurochemistry (2008) vol. 106, pp. 650-661.
Non-Final Office Action received for U.S. Appl. No. 15/037,559, dated Jun. 25, 2019, 34 pages.
Chinese Office Action dated Sep. 20, 2019, which issued during prosecution of Chinese Application No. 201480073413.0, 15 pages total.
Japanese Office Action dated Aug. 13, 2019, which issued during prosecution of Japanese Application No. 2016-532043, 10 pages total, only English portion considered.
Canadian Communication received for Canadian Patent Application No. 2,833,389, dated Nov. 22, 2019, 4 pages total.
European Communication (Extended European Search Report) received for European Application No. 17771018.3, dated Sep. 20, 2019, 9 pages total.
Cloutier, F. et al., "MicroRNAs as Potential Circulating Biomarkers for Amyotrophic Lateral Sclerosis" Journal of Molecular Neuroscience (2014) vol. 56, No. 1, pp. 102-112.
Weber, J.A. et al., "The microRNA spectrum in 12 body fluids" Clin. Chem. (2010) vol. 56, pp. 1733-1741.
Wu, Q. et al., "Next-Generation Sequencing of MicroRNAs for Breast Cancer Detection" Journal of Biomedicine and Biotechnology (2011) vol. 2011, Article ID 597145, 7 pages total.
Xu, S. et al. "MicroRNA (miRNA) transcriptome of mouse retina and identification of a sensory organ-specific miRNA cluster" Journal of Biological Chemistry (2007) vol. 282, pp. 25053-25066.
Yoo, M.S. et al., "Oxidative Stress Regulated Genes in Nigral Dopaminergic Neuronal Cells: Correlation with the Known Pathology in Parkinson's Disease" Molecular Brain Research (2003) vol. 110, pp. 76-84.
Yoshiyama, Y. et al., "Synapse Loss and Microglial Activation Precede Tangles in P301S Tauopathy Mouse Model" Neuron (2007) vol. 53, pp. 337-351.
Zampetaki, A. et al., "Plasma microRNA Profiling Reveals Loss of Endothelial MiR-126 and Other microRNAs in Type 2 Diabetes" Circulation Research (2010) vol. 107, pp. 810-817.
Zhao, H. et al., "A Pilot Study of Circulating miRNAs as Potential Biomarkers of Early Stage Breast Cancer" PLoS One (2010) vol. 5, No. 10, 12 pages total.
Communication (International Preliminary Report on Patentability) issued by the International Searching Authority in International Patent Application No. PCT/US2017/023470 dated Jul. 31, 2017, 20 pages total.
Lugli, G. et al., "File S2. Entire list of measured human, rat and mouse microRNAs by microarray after filtering and normalization" Journal of Neurochemistry (2008) vol. 106.
Maes, O. C. et al. "Methodology for Discovery of Alzheimer's Disease Blood-Based Biomarkers" J Gerontol a Biol Sci Med Sci. (2009) vol. 64A, pp. 636-645.
Maes, O. C. et al., "MicroRNA: Implications for Alzheimer Disease and other Human CNS Disorders" Current Genomics (2009) vol. 10, pp. 154-168.
Mapstone, M. et al., "Plasma phospholipids identify antecedent memory impairment in older adults" Nature Medicine (2013) vol. 20, No. 4, pp. 415-418.
Mature Sequence hsa-miR-127-3p, Available online at: <http://www.mirbase.org/cgi-bin/mature.pl?mature_acc=MIMAT0000446>, 1 page.
McDonald, J.S. et al., "Analysis of circulating microRNA: pre analytical and analytical challenges" Clin Chem. (2011) vol. 57, pp. 833-840.
McKhann, G.M. et al., "The diagnosis of dementia due to Alzheimer's disease: Recommendations from National Institute on Aging-Alzheimer's Association workgroups on diagnostic guidelines for Alzheimer's disease" Alzheimer's Dement. (2011) vol. 7, pp. 263-269.
Mestdagh, P. et al., "High-throughput Stem-loop RT-qPCR miRNA Expression Profiling Using Minute Amounts of Input RNA" Nucleic Acids Research (2008) vol. 36, No. 21, 8 pages.

(56) References Cited

OTHER PUBLICATIONS

Meyer, S.U. et al., "Normalization Strategies for MircoRNA Profiling Experiments: A 'Normal' Way to a Hidden Layer of Complexity?" Biotechnol. Lett. (2010) vol. 32, pp. 1777-1788.
Miller, G., "Alzheimer's biomarker initiative hits its stride" Science (2009) vol. 326, pp. 386-389.
MirVana PARIS Kit Instructions Ambion, Life Technologies (2011) 36 pages total.
Mitchell, P.S. et al., "Circulating microRNAs as stable blood-based markers for cancer detection" Proc Natl Acad Sci USA (2008) vol. 105, No. 30, pp. 10513-10518.
Miyachi, M. et al. "Circulating muscle-specific microRNA, miR-206, as a potential diagnostic marker for rhabdomyosarcoma" Biochem. Biophys. Res. Commun. (2010), vol. 400, pp. 89-93.
Murayama, S. et al., "The Pathology of Alzheimer's Disease" Clinician (2006) No. 553, pp. 15-19.
Natera-Naranjo, O. et al., "Identification and quantitative analyses of microRNAs located in the distal axons of sympathetic neurons" RNA (2010) vol. 16, pp. 1516-1529.
Non-Final Office Action received for U.S. Appl. No. 13/508,262, dated Mar. 7, 2013, 12 pages.
Non-Final Office Action received for U.S. Appl. No. 14/112,684, dated Jul. 9, 2015, 23 pages.
Non-Final Office Action received for U.S. Appl. No. 14/112,765, dated Apr. 28, 2015, 15 pages.
Non-Final Office Action received for U.S. Appl. No. 15/037,559, dated Jul. 27, 2017, 14 pages.
Non-Final Office Action received for U.S. Appl. No. 15/390,110, dated Jan. 31, 2018, 46 pages.
Non-Final Office Action received for U.S. Appl. No. 15/606,747, dated Jun. 1, 2018, 60 pages.
Olsen, L. et al., "MicroRNAs Show Mutually Exclusive Expression Patterns in the Brain of Adult Male Rats" PLoS One (2009) vol. 4, No. 10, e7225.
Peltier, H.J. et al., "Normalization of microRNA expression levels in quantitative RT-PCR assays: identification of suitable reference RNA targets in normal and cancerous human solid tissues" RNA (2008) vol. 14, pp. 844-852.
Petersen, R.C. et al., "Prevalence of Mild Cognitive Impairment is Higher in Men" The Mayo Clinic Study of Aging, Neurology (2010) vol. 75, pp. 889-897.
Pogue, A.I. et al., "Micro RNA-125b (miRNA-125b) Function in Astrogliosis and Glial Cell Proliferation" Neuroscience Letters (2010) vol. 476, pp. 18-22.
Ray, S. et al., "Classification and prediction of clinical Alzheimer's diagnosis based on plasma signaling proteins" Nat Med. (2007) vol. 13, No. 11, pp. 1359-1362.
Satoh, J-i., "Molecular network of microRNA targets in Alzheimer's disease brains" Exp Neurol. (2012) vol. 235, pp. 436-446, ePub Sep. 16, 2011.
Satoh, J-i., "MicroRNAs and Their Therapeutic Potential for Human Diseases: Aberrant MicroRNA Expression in Alzheimer's Disease Brain" J Pharmacol Sci. (2010) vol. 114, pp. 269-275.
Schipper, H.M. et al., "MicroRNA expression in Alzheimer blood mononuclear cells" Gene Regul. Syst. Bio. (2007) vol. 1, pp. 263-274.
Schmand, B. et al., "Value of Neurophysiological Tests, Neuroimaging, and Biomarkers for Diagnosing Alzheimer's Disease in Younger and Older Age Cohorts" J Am Geriatr Soc. (2001) vol. 59, pp. 1705-1710.
Schratt, G. M. et al., "A brain-specific microRNA regulates dendritic spine development" Nature (2006) vol. 439, pp. 283-289.
Schratt, G., "microRNAs at the synapse" Nature Reviews Neuroscience (2009) vol. 10, pp. 842-849.
Sempere, L. F. et al., "Expression profiling of mammalian microRNAs uncovers a subset of brain-expressed microRNAs with possible roles in murine and human neuronal differentiation" Genome Biology (2004) vol. 5, No. R13, pp. R13.1-R13.11.
Sheinerman, K.S. et al., "Plasma microRNA biomarkers for detection of mild cognitive impairment" Aging (2012) vol. 4, No. 9, pp. 590-605.
Sheinerman, K.S. et al., "Analysis of organ-enriched micro-RNAs in plasma as an approach to development of Universal Screening Test: feasibility study" Journal of Translational Medicine (2013) vol. 11, No. 304.
Sheinerman, K.S. et al., "Circulating cell-free microRNA as biomarkers for screening, diagnosis, and monitoring of neurode-generative diseases and other neurologic pathologies" Front.Cell.Neurosci. (2013) vol. 7, Art. 150, pp. 1-10.
Sheinerman, K.S. et al., "Early detection of neurodegenerative diseases" Cell Cycle (2013) vol. 12, No. 1.
Sheinerman, K.S. et al., "Plasma microRNA biomarkers for detection of mild cognitive impairment: biomarker validation study" Aging (2012) vol. 4, No. 9, pp. 17-18, 560-605.
Sheinerman, K.S. et al., Universal screening test based on analysis of circulating organ-enriched microRNAs: a novel approach to diagnostic screening, Expert Rev. Mol. Diagn. (2015) vol. 15, No. 3, pp. 329-338.
Shingara, J. et al. "An optimized isolation and labeling platform for accurate microRNA expression profiling" RNA (2005) vol. 11, pp. 1461-1470.
Skog, J. et al., "Glioblastoma microvesicles transport RNA and proteins that promote tumour growth and provide diagnostic biomarkers" Nat Cell Biol. (2008) vol. 10, No. 12, pp. 1470-1476.
Sperling, R.A. et al., "Toward Defining the Preclinical Stages of Alzheimer's Disease: Recommendations from the National Institute on Aging and the Alzheimer's Association Workgroup" Alzheimer's & Dementia (2011) pp. 1-13.
Sperling, R.A. et al., "Toward Defining the Preclinical Stages of Alzheimer's Disease: Recommendations from the National Institute on Aging-Alzheimer's Association workgroups on diagnostic guidelines for Alzheimer's disease" Alzheimer's Dement. (2011) vol. 7, pp. 280-292.
Supplementary Figures and Tables from Peltier et al. (RNA (2008), 14-844-852) (the balance of the article is of record as citation C47 in the IDS of Oct. 18, 2013).
Veerla, S. et al. "MiRNA expression in urothelial carcinomas: important roles of miR-10a, miR-222, miR-125b, miR-7 and miR452 for lung stage and metastasis, and frequent homozygous losses of miR-31" International Journal of Cancer (2009), vol. 124, pp. 2236-2242.
Vlaminck, I. et al., "Circulating Cell-Free DNA Enables Noninvasive Diagnosis of Heart Transplant Rejection" Science Translational Medicine (2014) vol. 6, No. 241, pp. 1-19.
Wang, G-K. et al., "Circulating microRNA: a novel potential biomarker for early diagnosis of acute myocardial infarction in humans" European Heart Journal (2010) vol. 31, Issue 6, pp. 659-666.
Wang, K. et al., "Circulating microRNAs, potential biomarkers for drug-induced liver injury" Proc Natl Acad Sci USA (2009) vol. 106, No. 11, pp. 4402-4407.
Wang, W-X. et al., "The Expression of MicroRNA miR-107 Decreases Early in Alzheimer's Disease and May Accelerate Disease Progression through Regulation of β-Site Amyloid Precursor Protein-Cleaving Enzyme 1" The Journal of Neuroscience (2008) vol. 28, pp. 1213-1223.
Wang, X., "A PCR-based Platform for microRNA Expression Profiling Studies" RNA (2009) vol. 15, pp. 716-723.
Adachi, T. et al., Plasma MicroRNA 499 as a Biomarker of Acute Myocardial Infarction, Clinical Chemistry, vol. 56, No. 7, pp. 1183-1185, 2010.
Albert, M.S. et al., "The diagnosis of mild cognitive impairment due to Alzheimer's disease: Recommendations from National Institute on Aging-Alzheimer's Association workgroup" Alzheimer's & Dementia (2011) vol. 7, pp. 270-279.
Australia Patent Examination Report No. 1 issued in Australian Patent Application No. 2012245580 dated Aug. 30, 2016, 3 pages.
Australia Patent Examination Report No. 1 issued in Australian Patent Application No. 2012245628 dated Jun. 8, 2016, 6 pages.
Australia Patent Examination Report No. 2 issued in Australian Patent Application No. 2012245580 dated Jun. 2, 2017, 4 pages.

(56) References Cited

OTHER PUBLICATIONS

Backes, C. et al., "A dictionary on microRNAs and their putative target pathways" Nucleic Acids Research (2010) vol. 38, pages 4476-4486.
Bak, M. et al., "MicroRNA expression in the adult mouse central nervous system" RNA. (2008) vol. 14, No. 3, pp. 432-444.
Bartel, D.P., "MicroRNAs: target recognition and regulatory functions" Cell (2009) vol. 136, pp. 215-233.
Bishop, D.L. et al., "Axon branch removal at developing synapses by axosome shedding" Neuron (2004) vol. 44, pp. 651-661.
Boeri, M. et al., "MicroRNA Signatures in Tissues and Plasma Predict Development and Prognosis of Computed Tomography Detected Lung Cancer" PNAS (2011) vol. 108, No. 9, pp. 3713-3718.
Braak, H. et al., "Neuropathological staging of Alzheimer's related changes" Acta Neuropathol (1991) vol. 82, pp. 239-259.
Brase, J. C. et al., "Circulating miRNAs are correlated with tumor progression in prostate cancer" International Journal of Cancer (2011) vol. 128, No. 3, pp. 608-616.
Brase, J. C. et al., "Serum microRNAs as non-invasive biomarkers for cancer" Molecular Cancer (2010) vol. 9, pp. 306-315.
Bredesen, D., "mCiRNA-Synaptic Crystal Ball?" Aging (2012) vol. 4, No. 11, pp. 732-733.
Canadian Communication received for Canadian Patent Application No. 2,780,222, dated Jan. 18, 2018, 5 pages.
Canadian Communication received for Canadian Patent Application No. 2,780,222, dated Nov. 18, 2016, 4 pages.
Canadian Communication received for Canadian Patent Application No. 2,833,375, dated Nov. 24, 2017, 7 pages.
Canadian Communication received for Canadian Patent Application No. 2,833,389, dated Nov. 21, 2017, 4 pages.
Charras, G. T. et al., "Life and times of a cellular bleb" Biophys J. (2008) vol. 94, No. 5, pp. 1836-1853.
Chen, X., "Characterization of microRNAs in serum: a novel class of biomarkers for diagnosis of cancer and other diseases" Cell Research (2008) vol. 18, pp. 997-1006.
Chim, S.S.C. et al., "Detection and Characterization of Placental MicroRNAs in Maternal Plasma" Clinical Chemistry (2008) vol. 54, No. 3, pp. 482-490.
Chinese Communication received for Chinese Patent Application No. 201280030048.6, dated Aug. 5, 2014, 13 pages total.
Chinese Office Action dated Aug. 15, 2016, which issued during prosecution of Chinese Application No. 201280030033.X, 8 pages total.
Chinese Office Action dated Aug. 5, 2015, which issued during prosecution of Chinese Application No. 201280030048.6, 16 pages total.
Chinese Office Action dated Jul. 23, 2014, which issued during prosecution of Chinese Application No. 201280030033.X, 12 pages total.
Chinese Office Action dated Jun. 2, 2015, which issued during prosecution of Chinese Application No. 201280030033.X, 12 pages total.
Chinese Office Action dated Mar. 26, 2015, which issued during prosecution of Chinese Application No. 201280030048.6, 10 pages total.
Chinese Office Action dated Nov. 24, 2015, which issued during prosecution of Chinese Application No. 201280030033.X, 10 pages total.
Cogswell, J. P. et al., "Identification of miRNA Changes in Alzheimer's Disease Brain and CSF Yields Putative Biomarkers and Insights into Disease Pathways" Journal of Alzheimer's Disease (2008) vol. 14, pp. 27-41.
Delrieu, J. et al., "Managing Cognitive Dysfunction through the Continuum of Alzheimer's Disease" CNS Drugs (2011) vol. 25, No. 3, pp. 213-226.
Eaton, B.A. et al., "Synapse disassembly" Genes Dev. (2003) vol. 17, pp. 2075-2082.
Edbauer, D. et al., "Regulation of synaptic structure and function by FMRP-associated microRNAs miR-125b and miR-132" Neuron (2010) vol. 65, No. 3, pp. 373-384.
Emery, V., "Alzheimer disease: are we intervening too late?" J Neural Transm. (2011) vol. 118, No. 9, pp. 1361-1378.
European Communication (extended European search report) dated Feb. 27, 2018, which issued during prosecution of European Application No. 17207859.4, 9 pages total.
European Communication dated Nov. 15, 2016, which issued during prosecution of European Application No. 16 185 046.6, 12 pages total.
European Communication (Extended European Search Report) dated Jun. 9, 2017, which issued during prosecution of European Application No. 14862355.6, 9 pages total.
European Communication pursuant to Article 94(3) EPC dated Aug. 21, 2014, which issued during prosecution of European Application No. 10 779 376.2, 6 pages total.
European Communication pursuant to Article 94(3) EPC dated Dec. 8, 2016, which issued during prosecution of European Application No. 12 773 705.4, 4 pages total.
European Communication pursuant to Article 94(3) EPC dated Jan. 5, 2016, which issued during prosecution of European Application No. 12 773 705.4, 6 pages total.
European Communication pursuant to Article 94(3) EPC dated Jun. 25, 2015, which issued during prosecution of European Application No. 12 774 179.1, 4 pages total.
European Communication pursuant to Article 94(3) EPC dated May 24, 2013, which issued during prosecution of European Application No. 10 779 376.2, 11 pages total.
European Communication pursuant to Article 94(3) EPC dated Nov. 6, 2015, which issued during prosecution of European Application No. 10 779 376.2, 7 pages total.
European Communication pursuant to Article 94(3) EPC received for European Patent Application No. 14862355.6, dated Mar. 20, 2018, 5 pages.
European Communication pursuant to Rules 161(2) and 162 EPC dated Nov. 26, 2013, which issued during prosecution of European Application No. 12 774 179.1, 3 pages total.
European Communication pursuant to Rules 70(2) and 70a(2) EPC received for European Application No. 12 774 179.1, dated Nov. 18, 2014, 1 page.
European Communication received for European Patent Application No. 12773705.4, dated Sep. 16, 2014, 6 pages.
European Extended Search Report issued in European Application No. EP16 192 259.6; dated Jan. 24, 2017, 8 pages.
European Search Report dated Jan. 26, 2015, which issued during prosecution of European Application No. 12 773 705.4, 12 pages total.
European Search Report dated Oct. 30, 2014, which issued during prosecution of European Application No. 12 774 179.1, 7 pages total.
Fackler, O.T., et al., "Cell motility through plasma membrane blebbing" J Cell Biol. (2008) vol. 181, No. 6, pp. 879-884.
Abdel-Salam, O.M.E. et al., "Drugs Used to Treat Parkinson's Disease, Present Status and Future Directions" CNS & Neurological Disorders—Drug Targets (2008) vol. 7, pp. 321-342.
Canadian Communication received for Canadian Patent Application No. 2,833,375, dated Dec. 9, 2019, 5 pages.
Gazewood, J.D. et al., "Parkinson Disease: An Update" American Family Physician (2013) vol. 87, No. 4, 7 pages total.
Kansara, S. et al., "Early Diagnosis and Therapy of Parkinson's Disease: Can Disease Progression be Curbed?" J. Neural Transm. (2013) vol. 120, pp. 197-210.
Restriction Requirement received for U.S. Appl. No. 16/028,206, dated Dec. 13, 2019, 11 pages total.
Final Office Action received for U.S. Appl. No. 15/037,559, dated Feb. 27, 2020, 17 pages.
Stem-loop Sequence has-mir-335 Accession No. MI0000816, Available online at: <http://www.mirbase.org/cgi-bin/mirna_entry.pl?acc=MI0000291>, 4 pages total.

(56) References Cited

OTHER PUBLICATIONS

Stem-loop Sequence has-mir-491 Accession No. MI0003126, Available online at: <http://www.mirbase.org/cgi-bin/mirna_entry.pl?acc=MI0003126>, 3 pages total.

Schymick, J. C. et al., "Expanding the Genetics of Amyotrophic Lateral Sclerosis and Frontotemporal Dementia" Alzheimer's Research & Therapy (2012) vol. 4, No. 30, 6 pages total.

Alzforum: Networking for a Cure, "Genetics Tie ALS into the Frontotemporal Dementia Spectrum" (2018) Available online at: <https://www.alzforum.org/news/research-news/genetics-tie-als-frontotemporal-dementia-spectrum>, 5 pages total.

Restriction Requirement received for U.S. Appl. No. 16/086,881, dated Jan. 15, 2020, 8 pages total.

Ashrafi, A. et al., "Leukocyte Telomere Length is Unrelated to Cognitive Performance Among Non-Demented and Demented Persons: An Examination of Long Life Family Study Participants" Journal of International Neuropsychological Society (2020) 12 pages total.

Coleman, R.A., "Of Mouse and Man—What is the Value of the Mouse in Predicting Gene Expression in Humans?" Drug Discovery Today (2003) vol. 8, No. 6, pp. 233-235.

Heegaard, N.H.H. et al., "Circulating Micro-RNA Expression Profiles in Early Stage Nonsmall Cell Lung Cancer" International Journal of Cancer (2012) vol. 130, pp. 1378-1386.

Liu, Z. et al., "Comparison of Differentually Expressed Genes in T Lymphocytes Between Human Autoimmune Disease and Murine Models of Autoimmune Disease" Clinical Immunology (2004) vol. 112, pp. 225-230.

Non-Final Office Action received for U.S. Appl. No. 16/086,881, dated Jun. 9, 2020, 34 pages total.

Urdinguio, R.G. et al., "Disrupted microRNA Expression Caused by Mecp2 Loss in a Mouse Model of Rett Syndrome" Epigenetics (2010) vol. 5, Issue 7, pp. 656-663.

Non-Final Office Action received for U.S. Appl. No. 16/028,206, dated May 21, 2020, 22 pages total.

\* cited by examiner

MIRNA-BASED METHODS FOR DETECTING AND MONITORING AGING

CROSS-REFERENCE TO RELATED APPLICATIONS

The present application claims priority to U.S. Provisional Patent Application Ser. No. 62/536,320, filed on Jul. 24, 2017, which application is hereby incorporated by reference in its entirety.

STATEMENT AS TO FEDERALLY SPONSORED RESEARCH

This invention was made with government support under grant AG053116 awarded by the National Institutes of Health. The government has certain rights in the invention.

TECHNICAL FIELD OF THE INVENTION

The present invention is directed to methods for detection, treatment monitoring, and slowing of aging by quantifying miRNAs in bodily fluids.

BACKGROUND OF THE INVENTION

After considerable success in fighting infections and a significant increase in life expectancy, diseases associated with aging became main causes of premature death in developed countries. Alzheimer's, Parkinson's and other neurodegenerative diseases (AD, PD and ND, respectively), cancer, diabetes and cardiovascular diseases (CVD) are most common pathologies, which in the best case complicate life and very often lead to patient's death (Xu J, Murphy S L, Kochanek K D, Arias E. Mortality in the United States, 2015. NCHS Data Brief. 2016; 267:1-7). In addition, these diseases have highly negative economic consequences for a patient, his/her family and society as a whole. Although both terms, "age associated diseases" and "aging associated diseases", are used to define these and some less common pathologies the latter is more correct because it currently becomes clear that their clinical manifestation is preceded by long (10-20 years) asymptomatic periods of disease development. Thus, better understanding of aging process could clarify the nature of mechanisms involved in their initiation and early stages of development.

Despite the significant efforts made in recent years that focused on elucidating the mechanisms of aging-related disease progression, much more work is needed to develop effective assays for early detection and treatment of these diseases.

There are two major reasons of this relative failure. First, in spite of significant progress in understanding underlying processes in development of these diseases, the real initiating mechanisms are mostly unclear. In addition, successful treatment of a single disease does not lead to significant gains in life span, because patients die from other pathologies (Olshansky S J, Carnes B A, Cassel C K. In search of Methuselah: estimating the upper limits to human longevity. Science. 1990; 250:634-640.; Scott C T, DeFrancesco L. Selling long life. Nature Biotechnol. 2015; 33:31-40). A popular emerging concept is that focusing on the development of drugs targeting aging early may be more beneficial than treatment of particular diseases (Kennedy B K, et al. Geroscience: Linking Aging to Chronic Disease. Cell. 2014; 159:709-713).

SUMMARY OF THE INVENTION

There is a need to develop methods for detecting biological age, monitoring progression of aging, monitoring anti-aging treatments, and methods for screening new compounds for slowing aging and aging-associated diseases. The present invention addresses these and other needs by providing the methods and compositions disclosed herein.

In one aspect, the invention provides a method for determining a biological age of a subject, which method comprises:

a) measuring the level of a first miRNA in a bodily fluid sample collected from the subject;

b) measuring the level of a second miRNA in the same bodily fluid sample as in step (a);

c) calculating the ratio of the levels of the miRNAs measured in steps (a) and (b); and d) comparing the ratio of the levels of the miRNAs calculated in step (c) with a corresponding control range of ratios for a given sex and age group;

e) (i) identifying the subject's biological age based on whether the ratio of the levels of the miRNAs calculated in step (c) falls within the corresponding control range of ratios for a given sex and age group, wherein said given sex and age group is within +/−10 years from the chronological age of the subject, and wherein (i) the subject is a 26-45 year old female by chronological age and miRNA pairs are selected from miR-182/miR-375, miR-487b/miR-370, miR-134/miR-370, miR-132/miR-375, miR-874/miR-375, miR-99a/miR-375, let-7e/miR-375, miR-134/miR-127, miR-433/miR-370, miR-182/miR-382, miR-874/miR-7, miR-135a/miR-7, and any combinations thereof;

(ii) the subject is a 36-55 year old female by chronological age and miRNA pairs are selected from miR-370/miR-323-3p, miR-491-5p/miR-182, miR-375/miR-99a, miR-411/miR-182, miR-370/miR-382, miR-370/miR-134, miR-370/miR-127, miR-135a/miR-182, miR-491-5p/miR-874, miR-375/miR-182, miR-370/miR-487b, miR-132/miR-874, miR-370/miR-182, miR-127/miR-182, miR-135a/miR-874, miR-195/miR-182, miR-370/miR-874, miR-433/miR-182, miR-411/miR-134, miR-375/miR-874, and any combinations thereof;

(iii) the subject is a 46-65 year old female by chronological age and miRNA pairs are selected from miR-491-5p/miR-411, miR-195/miR-135a, miR-195/miR-99a, miR-182/miR-135a, miR-323-3p/miR-411, miR-382/miR-411, miR-132/miR-135a, miR-132/let-7e, miR-195/miR-411, miR-132/miR-411, miR-323-3p/miR-370, and any combinations thereof;

(iv) the subject is a 56-75 year old female by chronological age and miRNA pairs are selected from miR-135a/miR-195, miR-181a/miR-195, miR-134/miR-323-3p, miR-874/miR-195, miR-134/miR-382, and any combinations thereof;

(vi) the subject is a 26-45 year old male by chronological age and miRNA pairs are selected from miR-135a/let-7e, miR-135a/miR-487b, miR-132/miR-411, miR-132/miR-127, miR-382/miR-487b, miR-135a/miR-411, miR-135a/miR-127, miR-132/miR-487b, miR-134/miR-127, miR-135a/miR-134, miR-135a/miR-181a, miR-99a/miR-487b, miR-99a/miR-127, miR-135a/miR-382, miR-135a/miR-7, miR-134/miR-487b, miR-135a/miR-370, miR-491-5p/miR-411, miR-874/miR-487b, miR-135a/miR-433, and any combinations thereof;

(vii) the subject is a 36-55 year old male by chronological age and miRNA pairs are selected from miR-370/miR-134, miR-127/miR-135a, miR-127/miR-134, miR-134/miR- 135a, miR-323-3p/miR-135a, miR-7/miR-135a, miR-487b/miR-134, and any combinations thereof; (viii) the subject is a 46-65 year old male by chronological age and miRNA pairs are selected from miR-433/miR-182, miR-433/miR-411, miR-433/miR-132, miR-382/miR-411, miR-433/miR-195, miR-491-5p/miR-181a, miR-135a/miR-182, miR-491-5p/let-7e, miR-433/miR-181a, miR-135a/miR-181a, miR-370/miR-182, miR-487b/miR-411, miR-135a/miR-7, miR-433/miR-370, and any combinations thereof;
(ix) the subject is a 56-75 year old male by chronological age and miRNA pairs are selected from miR-182/miR-370, miR-134/miR-382, miR-7/miR-370, miR-195/miR-370, miR-411/miR-382, miR-182/miR-433, miR-195/miR-433, miR-874/miR-433, miR-181a/miR-370, miR-874/miR-370, miR-132/miR-433, miR-127/miR-370, miR-181a/miR-433, miR-7/miR-433 miR-134/miR-370, miR-99a/miR-382, miR-181a/miR-874, miR-182/miR-411, miR-127/miR-382, miR-181a/let-7e, miR-132/miR-370, and any combinations thereof.

In one embodiment, the method comprises further refining the biological age of the subject, which method comprises:

f) measuring the level of a third miRNA in a bodily fluid sample collected from the subject (the same or different bodily fluid sample as in step (a));

g) measuring the level of a fourth miRNA in the same bodily fluid sample as in step (f);

h) calculating the ratio of the levels of the miRNAs measured in steps (f) and (g); and i) comparing the ratio of the levels of the miRNAs calculated in step (h) with a corresponding control range of ratios for a given sex and age group;

j) (i) identifying the subject's biological age based on whether the ratio of the levels of the miRNAs calculated in step (h) falls within the corresponding control range of ratios for a given sex and age group, wherein said given sex and age group is within +/−5 years from the chronological age of the subject, and wherein (i) the subject is a 26-35 year old female by chronological age and miRNA pairs are selected from miR-135a/miR-323-3p, miR-411/miR-370, miR-411/miR-127, and any combinations thereof;

(ii) the subject is a 36-45 year old female by chronological age and miRNA pairs are selected from miR-134/miR-135a, miR-375/let-7e, miR-375/miR-135a, and any combinations thereof;

(iii) the subject is a 46-55 year old female by chronological age and miRNA pairs are selected from miR-182/miR-195, miR-433/miR-411, let-7e/miR-135a, and any combinations thereof;

(iv) the subject is a 56-65 year old female by chronological age and miRNA pairs are selected from miR-323-3p/miR-433, miR-382/miR-134, miR-132/miR-135a, and any combinations thereof;

(v) the subject is a 66-75 year old female by chronological age and miRNA pairs are selected from miR-132/miR-181a, miR-127/miR-487b, and any combinations thereof;

(vi) the subject is a 26-35 year old male by chronological age and miRNA pairs are selected from miR-135a/miR-491-5p, miR-135a/miR-195, miR-411/miR-323-3p, miR-127/miR-323-3p, and any combinations thereof;

(vii) the subject is a 36-45 year old male by chronological age and miRNA pairs are selected from miR-127/miR-134, miR-382/let-7e, miR-132/let-7e, and any combinations thereof;

(viii) the subject is a 46-55 year old male by chronological age and miRNA pairs are selected from miR-135a/miR-99a, miR-323-3p/miR-127, miR-181a/miR-411, and any combinations thereof;

(ix) the subject is a 56-65 year old male by chronological age and miRNA pairs are selected from miR-182/miR-491-5p, miR-135a/miR-99a, and any combinations thereof;

(x) the subject is a 66-75 year old male by chronological age and miRNA pairs are selected from miR-874/miR-491-5p, miR-874/miR-132, miR-127/miR-433, and any combinations thereof.

In one embodiment of any of the above methods, the control range of ratios for a given sex and age group is a statistically validated predetermined range of values established by determining the ratios of the same miRNAs in a similarly processed bodily fluid in a large cohort of healthy subjects (e.g., at least 50 subjects).

In one embodiment of any of the above methods, the comparison involves using Logistic Regression.

In one embodiment of any of the above methods,
step (c) involves
(1) calculating using a suitably programmed processor, the ratio of the levels of the miRNAs measured in steps (a) and (b);
(2) calculating, by the processor and based on the ratio determined in step (c)(1), a first probability based on a first predefined probability distribution curve, wherein the first predefined probability distribution curve corresponds to the biological age status;
(3) calculating, by the processor and based on the ratio determined in step (c)(1), a second probability based on a second predefined probability distribution curve, wherein the second predefined probability distribution curve corresponds to a sex- and age-matched control; and step (e) involves (i) identifying, by the processor, the subject's biological age based on whether the first probability falls within the corresponding control range of probabilities for the given sex and age group.

In another aspect, the invention provides a method for monitoring the rate of progression of aging (e.g., brain aging) in a subject, which method comprises:

a) measuring the level of a first miRNA in two or more bodily fluid samples collected from the subject, wherein the samples have been collected at spaced apart time points (e.g., within 0.5-2 years of each other);

b) measuring the level of a second miRNA in the same bodily fluids samples as in step (a);

c) calculating the ratio of the levels of the miRNAs measured in steps (a) and (b) for each bodily fluid sample;

d) calculating a difference in the ratio of the levels of the miRNAs calculated in step (c) between an earlier collected and a later collected bodily fluid samples by subtracting the ratio of the levels of the miRNAs calculated in step (c) for an the earlier collected bodily fluid sample from the ratio of the levels of the miRNAs calculated in step (c) for the later collected bodily fluid sample;

e) comparing the difference calculated in step (d) with a corresponding control range of differences for a given sex and age group, and f) (i) determining that the aging in the subject has progressed at a higher than normal rate if the difference calculated in step (d) is larger than the corresponding control range of differences, or (ii) determining that the aging in the subject has progressed at a normal rate if the difference calculated in step (d) falls within the corresponding control range of differences, or (iii) determining that the aging in the subject has progressed at a lower than normal rate if the difference calculated in step (c) is smaller than the corresponding control range of differences, wherein
(i) the subject is a 26-35 year old female by chronological or biological age and miRNA pairs are selected from miR-135a/miR-323-3p, miR-411/miR-370, miR-411/miR-127, and any combinations thereof;
(ii) the subject is a 36-45 year old female by chronological or biological age and miRNA pairs are selected from miR-134/miR-135a, miR-375/let-7e, miR-375/miR-135a, and any combinations thereof;
(iii) the subject is a 46-55 year old female by chronological or biological age and miRNA pairs are selected from miR-182/miR-195, miR-433/miR-411, let-7e/miR-135a, and any combinations thereof;
(iv) the subject is a 56-65 year old female by chronological or biological age and miRNA pairs are selected from miR-323-3p/miR-433, miR-382/miR-134, miR-132/miR-135a, and any combinations thereof;
(v) the subject is a 66-75 year old female by chronological or biological age and miRNA pairs are selected from miR-132/miR-181a, miR-127/miR-487b, and any combinations thereof (vi) the subject is a 26-35 year old male by chronological or biological age and miRNA pairs are selected from miR-135a/miR-491-5p, miR-135a/miR-195, miR-411/miR-323-3p, miR-127/miR-323-3p, and any combinations thereof;
(vii) the subject is a 36-45 year old male by chronological or biological age and miRNA pairs are selected from miR-127/miR-134, miR-382/let-7e, miR-132/let-7e, and any combinations thereof;
(viii) the subject is a 46-55 year old male by chronological or biological age and miRNA pairs are selected from miR-135a/miR-99a, miR-323-3p/miR-127, miR-181a/miR-411, and any combinations thereof;
(ix) the subject is a 56-65 year old male by chronological or biological age and miRNA pairs are selected from miR-182/miR-491-5p, miR-135a/miR-99a, and any combinations thereof;
(x) the subject is a 66-75 year old male by chronological or biological age and miRNA pairs are selected from miR-874/miR-491-5p, miR-874/miR-132, miR-127/miR-433, and any combinations thereof.

In one embodiment of the above method, the subject is a female subject during perimenopause or menopause, or after oophorectomy, or undergoing a sex hormone therapy or anti sex hormone therapy, and wherein miRNA pairs are selected from miR-182/miR-195, miR-433/miR-411, let-7e/miR-135a, miR-323-3p/miR-433, miR-382/miR-134, miR-132/miR-135a, and any combinations thereof In one embodiment of the above aging monitoring method, the subject is a male subject undergoing a sex hormone therapy or anti sex hormone therapy, and wherein miRNA pairs are selected from miR-182/miR-491-5p, miR-135a/miR-99a, miR-874/miR-491-5p, miR-874/miR-132, miR-127/miR-433, and any combinations thereof.

In one embodiment of the above aging monitoring method, the control range of differences for a given sex and age group is a statistically validated predetermined range of values established by determining the ratios of the same miRNAs in a similarly processed bodily fluid in a large cohort of healthy subjects (e.g., at least 50 subjects).

In one embodiment of any of the above methods of the invention, the method further comprises administering an anti-aging treatment to the subject. Non-limiting examples of anti-aging treatments include, e.g., diets, exercise regimens, cognitive work, antioxidants, anti-aging drugs (e.g., drugs targeting neurodegeneration, anti-apoptotic compounds, stem cells, metformin, rapamycin, resveratrol, NAD+ precursors, TORC1 inhibitors, etc.), miRNAs (e.g., PG-secreted and/or PG-enriched miRNAs as discussed below), oligonucleotides targeting miRNAs, and any combinations thereof.

In another aspect, the invention provides a method for monitoring the effect of a treatment on progression of aging (e.g., brain aging) in a subject, which method comprises:
a) measuring the level of a first miRNA in a bodily fluid sample collected from the subject prior to initiation of the treatment;
b) measuring the level of a second miRNA in the same bodily fluid sample as in step (a);
c) calculating the ratio of the levels of the miRNAs measured in steps (a) and (b);
d) measuring the level of the same first miRNA as in step (a) in one or more bodily fluid sample(s) collected from the subject in the course of or following the treatment;
e) measuring the level of the same second miRNA as in step (b) in the same bodily fluid sample(s) as in step (d);
f) calculating the ratio of the levels of the miRNAs measured in steps (d) and (e) for each bodily fluid sample;
g) calculating a difference in the ratios of the levels of the miRNAs calculated in steps (c) and (f) by subtracting the ratio of the levels of the miRNAs calculated in step (f) from the ratio of the levels of the miRNAs calculated in step (c), and optionally comparing the ratios of the levels of the miRNA calculated in step (f) between different samples in step (d), and
h) comparing the difference(s) calculated in step (g) with a corresponding control range of differences for a given sex and age group, and
i) (i) determining that the treatment is effective for slowing aging if the difference calculated in step (g) is larger than or falls within the corresponding control range of differences, or (ii) determining that the treatment is not effective for slowing aging if the difference calculated in step (g) is smaller than the corresponding control range of differences, wherein
(i) the subject is a 26-35 year old female by chronological or biological age and miRNA pairs are selected from miR-135a/miR-323-3p, miR-411/miR-370, miR-411/miR-127, and any combinations thereof;
(ii) the subject is a 36-45 year old female by chronological or biological age and miRNA pairs are selected from miR-134/miR-135a, miR-375/let-7e, miR-375/miR-135a, and any combinations thereof;
(iii) the subject is a 46-55 year old female by chronological or biological age and miRNA pairs are selected from miR-182/miR-195, miR-433/miR-411, let-7e/miR-135a, and any combinations thereof;
(iv) the subject is a 56-65 year old female by chronological or biological age and miRNA pairs are selected from miR-323-3p/miR-433, miR-382/miR-134, miR-132/miR-135a, and any combinations thereof;
(v) the subject is a 66-75 year old female by chronological or biological age and miRNA pairs are selected from miR-132/miR-181a, miR-127/miR-487b, and any combinations thereof;
(vi) the subject is a 26-35 year old male by chronological or biological age and miRNA pairs are selected from miR-135a/miR-491-5p, miR-135a/miR-195, miR-411/miR-323-3p, miR-127/miR-323-3p, and any combinations thereof;

(vii) the subject is a 36-45 year old male by chronological or biological age and miRNA pairs are selected from miR-127/miR-134, miR-382/let-7e, miR-132/let-7e, and any combinations thereof;
(viii) the subject is a 46-55 year old male by chronological or biological age and miRNA pairs are selected from miR-135a/miR-99a, miR-323-3p/miR-127, miR-181a/miR-411, and any combinations thereof;
(ix) the subject is a 56-65 year old male by chronological or biological age and miRNA pairs are selected from miR-182/miR-491-5p, miR-135a/miR-99a, and any combinations thereof;
(x) the subject is a 66-75 year old male by chronological or biological age and miRNA pairs are selected from miR-874/miR-491-5p, miR-874/miR-132, miR-127/miR-433, and any combinations thereof.

In a related aspect, the invention provides a method for monitoring the effect of a treatment on progression of aging (e.g., brain aging) in a subject, which method comprises:

a) measuring the level of a first miRNA in a bodily fluid sample collected from the subject prior to initiation of the treatment;
b) measuring the level of a second miRNA in the same bodily fluid sample as in step (a);
c) calculating the ratio of the levels of the miRNAs measured in steps (a) and (b);
d) measuring the level of the same first miRNA as in step (a) in one or more bodily fluid sample(s) collected from the subject in the course of or following the treatment;
e) measuring the level of the same second miRNA as in step (b) in the same bodily fluid sample(s) as in step (d);
f) calculating the ratio of the levels of the miRNA measured in steps (d) and (e) for each bodily fluid sample;
g) comparing the ratios of the levels of the miRNA calculated in steps (c) and (f), and optionally comparing the ratios of the levels of the miRNA calculated in step (f) between different samples in step (d), and
h) (i) determining that the treatment is effective for slowing aging if the ratio of the levels of the miRNA calculated in step (c) is higher than the corresponding ratio(s) calculated in step (f), or (ii) determining that the treatment is not effective for slowing aging if the ratio of the levels of the miRNA calculated in step (c) is not higher than the corresponding ratio(s) calculated in step (f),
wherein
(i) the subject is a 26-35 year old female by chronological or biological age and miRNA pairs are selected from miR-135a/miR-323-3p, miR-411/miR-370, miR-411/miR-127, and any combinations thereof;
(ii) the subject is a 36-45 year old female by chronological or biological age and miRNA pairs are selected from miR-134/miR-135a, miR-375/let-7e, miR-375/miR-135a, and any combinations thereof;
(iii) the subject is a 46-55 year old female by chronological or biological age and miRNA pairs are selected from miR-182/miR-195, miR-433/miR-411, let-7e/miR-135a, and any combinations thereof;
(iv) the subject is a 56-65 year old female by chronological or biological age and miRNA pairs are selected from miR-323-3p/miR-433, miR-382/miR-134, miR-132/miR-135a, and any combinations thereof;
(v) the subject is a 66-75 year old female by chronological or biological age and miRNA pairs are selected from miR-132/miR-181a, miR-127/miR-487b, and any combinations thereof;
(vi) the subject is a 26-35 year old male by chronological or biological age and miRNA pairs are selected from miR-135a/miR-491-5p, miR-135a/miR-195, miR-411/miR-323-3p, miR-127/miR-323-3p, and any combinations thereof;
(vii) the subject is a 36-45 year old male by chronological or biological age and miRNA pairs are selected from miR-127/miR-134, miR-382/let-7e, miR-132/let-7e, and any combinations thereof;
(viii) the subject is a 46-55 year old male by chronological or biological age and miRNA pairs are selected from miR-135a/miR-99a, miR-323-3p/miR-127, miR-181a/miR-411, and any combinations thereof;
(ix) the subject is a 56-65 year old male by chronological or biological age and miRNA pairs are selected from miR-182/miR-491-5p, miR-135a/miR-99a, and any combinations thereof;
(x) the subject is a 66-75 year old male by chronological or biological age and miRNA pairs are selected from miR-874/miR-491-5p, miR-874/miR-132, miR-127/miR-433, and any combinations thereof.

In one embodiment of any of the above treatment monitoring methods, the subject is a female subject during perimenopause or menopause, or after oophorectomy.

In one embodiment of any of the above treatment monitoring methods, the subject is a female or male subject undergoing a sex hormone therapy or anti sex hormone therapy.

In one embodiment of any of the above treatment monitoring methods, the control range of differences for a given sex and age group is a statistically validated predetermined range of values established by determining the ratios of the same miRNAs in a similarly processed bodily fluid in a large cohort of healthy subjects (e.g., at least 50 subjects).

In one embodiment of any of the above treatment monitoring methods, the method comprises administering the treatment to the subject.

In another aspect, the invention provides a method for identifying a compound useful for slowing aging (e.g., brain aging) in a subject, which method comprises:

a) measuring the level of a first miRNA in a bodily fluid sample, wherein said bodily fluid sample(s) is collected from the subject prior to test compound administration;
b) measuring the level of a second miRNA in the same bodily fluid sample as in step (a);
c) calculating the ratio of the levels of the miRNA measured in steps (a) and (b);
d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) calculating the ratio of the levels of the miRNAs measured in steps (d) and (e) for each of the bodily fluid samples collected from the subject following administration of the test compound;
g) comparing the ratio of the levels of the miRNA calculated in steps (c) and (f), and
h) (i) identifying that the test compound is useful for slowing aging if the ratio of the levels of the miRNA calculated in step (f) is lower than the ratio of the levels of the miRNA calculated in step (c); (ii) identifying that the test compound is not useful for slowing aging if the ratio of the levels of the miRNA calculated in step (f) is not lower than the ratio of the levels of the miRNAs calculated in step (c),
wherein
(i) the subject is a 26-35 year old female by chronological or biological age and miRNA pairs are selected from miR-135a/miR-323-3p, miR-411/miR-370, miR-411/miR-127, and any combinations thereof;

(ii) the subject is a 36-45 year old female by chronological or biological age and miRNA pairs are selected from miR-134/miR-135a, miR-375/let-7e, miR-375/miR-135a, and any combinations thereof;

(iii) the subject is a 46-55 year old female by chronological or biological age and miRNA pairs are selected from miR-182/miR-195, miR-433/miR-411, let-7e/miR-135a, and any combinations thereof;

(iv) the subject is a 56-65 year old female by chronological or biological age and miRNA pairs are selected from miR-323-3p/miR-433, miR-382/miR-134, miR-132/miR-135a, and any combinations thereof;

(v) the subject is a 66-75 year old female by chronological or biological age and miRNA pairs are selected from miR-132/miR-181a, miR-127/miR-487b, and any combinations thereof;

(vi) the subject is a 26-35 year old male by chronological or biological age and miRNA pairs are selected from miR-135a/miR-491-5p, miR-135a/miR-195, miR-411/miR-323-3p, miR-127/miR-323-3p, and any combinations thereof;

(vii) the subject is a 36-45 year old male by chronological or biological age and miRNA pairs are selected from miR-127/miR-134, miR-382/let-7e, miR-132/let-7e, and any combinations thereof;

(viii) the subject is a 46-55 year old male by chronological or biological age and miRNA pairs are selected from miR-135a/miR-99a, miR-323-3p/miR-127, miR-181a/miR-411, and any combinations thereof;

(ix) the subject is a 56-65 year old male by chronological or biological age and miRNA pairs are selected from miR-182/miR-491-5p, miR-135a/miR-99a, and any combinations thereof;

(x) the subject is a 66-75 year old male by chronological or biological age and miRNA pairs are selected from miR-874/miR-491-5p, miR-874/miR-132, miR-127/miR-433, and any combinations thereof.

In one embodiment of the above method for identifying a compound useful for slowing aging, the method comprises administering the test compound to the subject.

In one embodiment of any of the above methods of the invention, the method comprises measuring the level and calculating the ratios of the levels for two or more different pairs of miRNAs.

In one embodiment of any of the above methods of the invention, the bodily fluid is selected from the group consisting of blood plasma, serum, urine, and saliva.

In one embodiment of any of the above methods of the invention, the method further comprises the step of collecting the bodily fluid sample(s) from the subject (e.g., performed prior to step (a)).

In one embodiment of any of the above methods of the invention, the level of the miRNAs is determined using a method selected from the group consisting of hybridization, polymerase chain reaction (PCR)-based detection, sequencing, and microfluidic technologies. Non-limiting examples of useful methods include, e.g., Northern blotting, bead-based flow-cytometry, oligonucleotide microchip, oligonucleotide microarray, solution hybridization assays, stem-loop reverse transcription-polymerase chain reaction [RT-PCR], quantitative RT-PCR based array method, Helicos small RNA sequencing, miRNA BeadArray, Roche 454, and ABI SOLiD. In one specific embodiment, the level of the miRNAs is determined using RT-PCR.

In one embodiment of any of the above methods of the invention, prior to measuring miRNA level, the miRNA is isolated and purified from the bodily fluid sample. Non-limiting examples of useful isolation and/or purification methods include, e.g., Trizol extraction, concentration and purification on anion-exchangers, magnetic beads covered by RNA-binding substances, and adsorption of miRNAs on complementary oligonucleotides.

In one embodiment of any of the above methods of the invention, the method further comprises reducing or eliminating degradation of the miRNAs. Non-limiting examples of useful methods for reducing or eliminating degradation of miRNAs include, e.g., adding RNase inhibitors, use of guanidine chloride, guanidine isothiocyanate, N-lauroylsarcosine, sodium dodecylsulphate (SDS), or a combination thereof.

In one embodiment of any of the above methods of the invention, the method further comprises applying one or more quality control (QC) and/or normalization steps. Non-limiting examples of useful QC or normalization steps include, e.g.:

a) comparing the concentration of ubiquitous miRNAs in the bodily fluid of the subject with pre-established normal values, b) synthesizing and using synthetic small RNA oligonucleotides as controls for losses during purification by adding them to bodily fluid samples before RNA purification, and c) normalizing miRNA concentration in urine on creatinine and/or albumin level to account for variations in kidney filtration.

In one embodiment of any of the above methods of the invention, the subject is human.

In one embodiment of any of the above methods of the invention, the subject is an experimental animal model.

In one embodiment of any of the above aging monitoring, treatment monitoring or compound screening methods, the aging is brain aging.

In one embodiment of any of the above aging monitoring, treatment monitoring or compound screening methods, the biological age is determined using the above method for determining a biological age.

In conjunction with any of the above diagnostic, monitoring and screening methods, the invention also provides various treatment methods relying on miRNA pair marker information as discussed above.

In a separate aspect, the invention provides a kit for determining a biological age, comprising primers and/or probes specific for one or more pairs of miRNAs selected from the group consisting of: miR-182/miR-375, miR-487b/miR-370, miR-134/miR-370, miR-132/miR-375, miR-874/miR-375, miR-99a/miR-375, let-7e/miR-375, miR-134/miR-127, miR-433/miR-370, miR-182/miR-382, miR-874/miR-7, miR-135a/miR-7, miR-370/miR-323-3p, miR-491-5p/miR-182, miR-375/miR-99a, miR-411/miR-182, miR-370/miR-382, miR-370/miR-134, miR-370/miR-127, miR-135a/miR-182, miR-491-5p/miR-874, miR-375/miR-182, miR-370/miR-487b, miR-132/miR-874, miR-370/miR-182, miR-127/miR-182, miR-135a/miR-874, miR-195/miR-182, miR-370/miR-874, miR-433/miR-182, miR-411/miR-134, miR-375/miR-874, miR-491-5p/miR-411, miR-195/miR-135a, miR-195/miR-99a, miR-182/miR-135a, miR-323-3p/miR-411, miR-382/miR-411, miR-132/miR-135a, miR-132/let-7e, miR-195/miR-411, miR-132/miR-411, miR-323-3p/miR-370, miR-135a/miR-195, miR-181a/miR-195, miR-134/miR-323-3p, miR-874/miR-195, miR-134/miR-382, miR-135a/let-7e, miR-135a/miR-487b, miR-132/miR-411, miR-132/miR-127, miR-382/miR-487b, miR-135a/miR-411, miR-135a/miR-127, miR-132/miR-487b, miR-134/miR-127, miR-135a/miR-134, miR-135a/miR-181a, miR-99a/miR-487b, miR-99a/miR-127, miR-135a/miR-382, miR-135a/miR-7, miR-134/miR-487b, miR-135a/miR-370, miR-491-5p/miR-411, miR-874/miR-487b, miR-135a/miR-433, miR-370/miR-134, miR-127/miR-135a, miR-127/miR-134, miR-134/miR-135a, miR-323-3p/miR-135a, miR-7/miR-135a, miR-487b/miR-134, miR-433/miR-182, miR-433/miR-411, miR-433/miR-132, miR-382/miR-411, miR-433/miR-195, miR-491-5p/miR-181a, miR-135a/miR-182, miR-491-5p/let-7e, miR-433/miR-181a, miR-135a/miR-181a, miR-370/miR-182, miR-487b/miR-411, miR-135a/miR-7, miR-433/miR-370, miR-182/miR-370, miR-134/miR-382, miR-7/miR-370, miR-195/miR-370, miR-411/miR-382, miR-182/miR-433, miR-195/miR-433, miR-874/miR-433, miR-181a/miR-370, miR-874/miR-370, miR-132/miR-433, miR-127/miR-370, miR-181a/miR-433, miR-7/miR-433, miR-134/miR-370, miR-99a/miR-382, miR-181a/miR-874, miR-182/miR-411, miR-127/miR-382, miR-181a/let-7e, miR-132/miR-370, and any combinations thereof.

In another aspect, the invention provides a kit for determining a biological age, monitoring aging (e.g., brain aging), monitoring the effect of a treatment on progression of aging (e.g., brain aging), or for identifying a compound useful for slowing aging (e.g., brain aging), said kit comprising primers and/or probes specific for one or more pairs of miRNAs selected from the group consisting of: miR-135a/miR-323-3p, miR-411/miR-370, miR-411/miR-127, miR-134/miR-135a, miR-375/let-7e, miR-375/miR-135a, miR-182/miR-195, miR-433/miR-411, and let-7e/miR-135a, miR-323-3p/miR-433, miR-382/miR-134, miR-132/miR-135a, miR-132/miR-181a and miR-127/miR-487b, miR-135a/miR-491-5p, miR-135a/miR-195, miR-411/miR-323-3p, and miR-127/miR-323-3p, miR-127/miR-134, miR-382/let-7e, and miR-132/let-7e, miR-135a/miR-99a, miR-323-3p/miR-127, miR-181a/miR-411, miR-182/miR-491-5p, miR-135a/miR-99a, miR-874/miR-491-5p, miR-874/miR-132, miR-127/miR-433, and any combinations thereof.

In one embodiment, the kits of the invention further comprise miRNA isolation means and/or miRNA purification means and/or instructions for use.

These and other aspects of the present invention will be apparent to those of ordinary skill in the art in the following description and claims.

BRIEF DESCRIPTION OF THE DRAWINGS

FIG. 6A shows old males versus young males. FIG. 6B shows old females versus young females. FIG. 6C shows all old subjects versus all young subjects. FIG. 6D shows young females versus young males. FIG. 6E shows old females versus old males. FIG. 6F shows all females versus all males.

DETAILED DESCRIPTION OF THE INVENTION

Figure 1A:
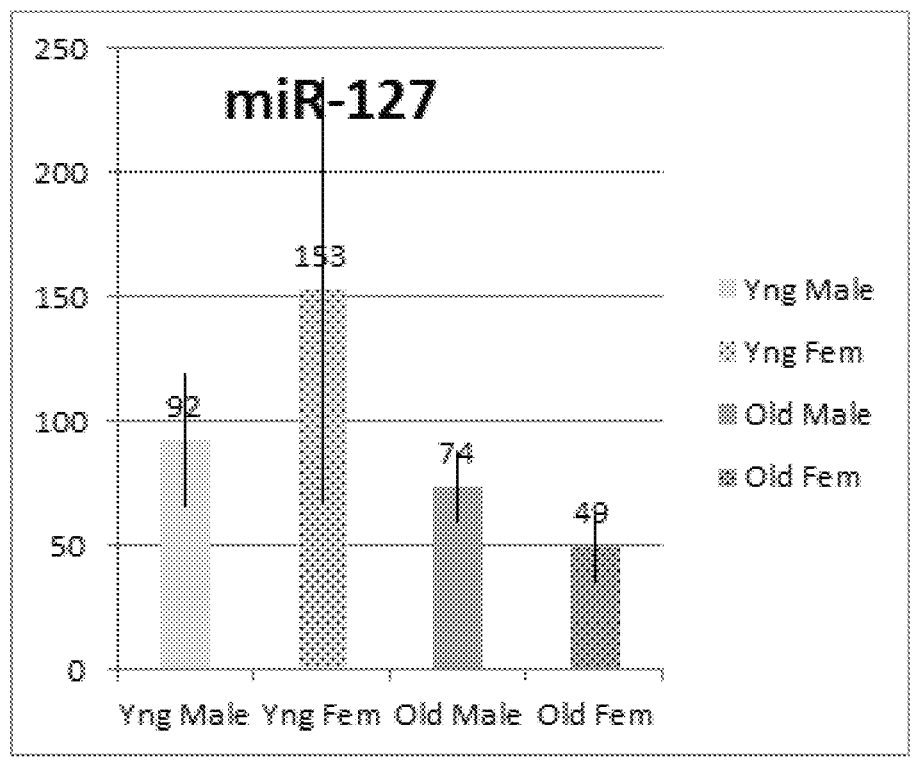
FIGS. 1A-1I show concentration of miR-134 family members (copies per 1 µl of plasma) in four groups of research participants (Example 1).
Figure 1B:
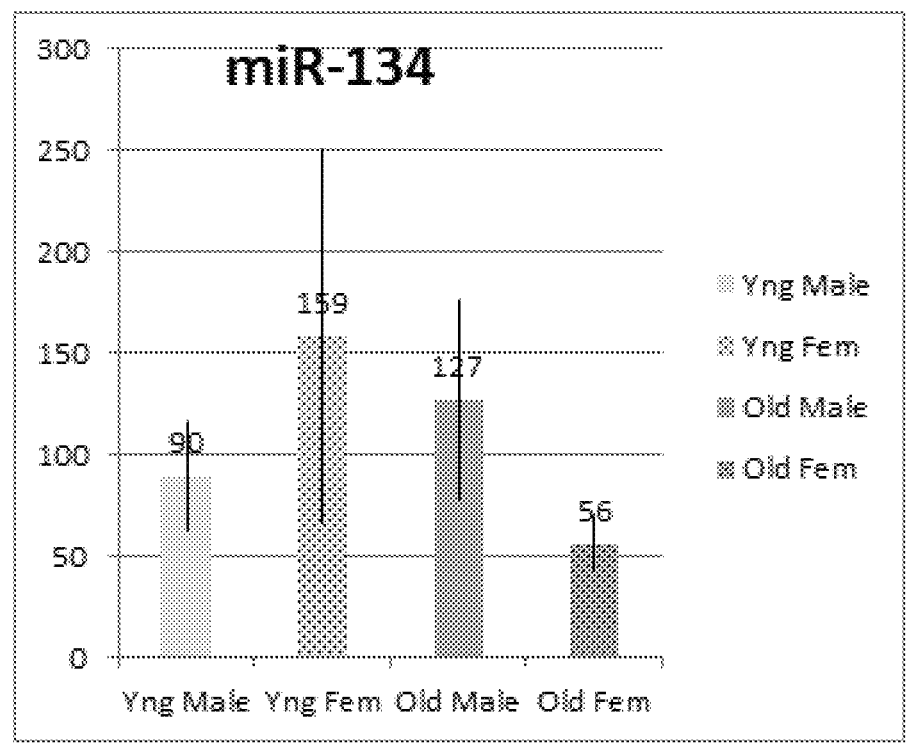
Figure 1C:
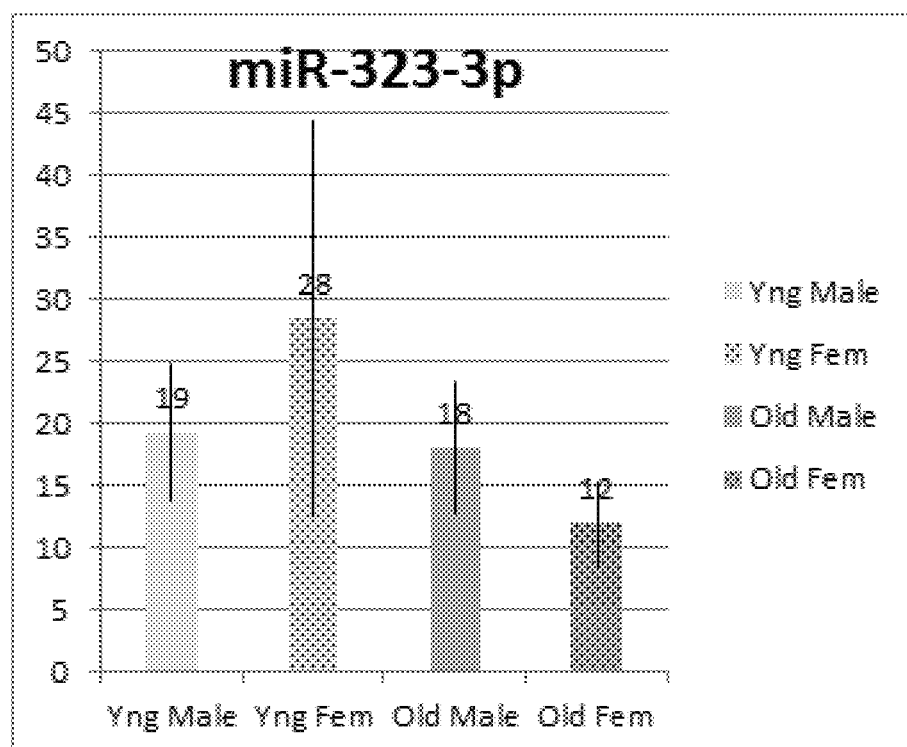
Figure 1D:
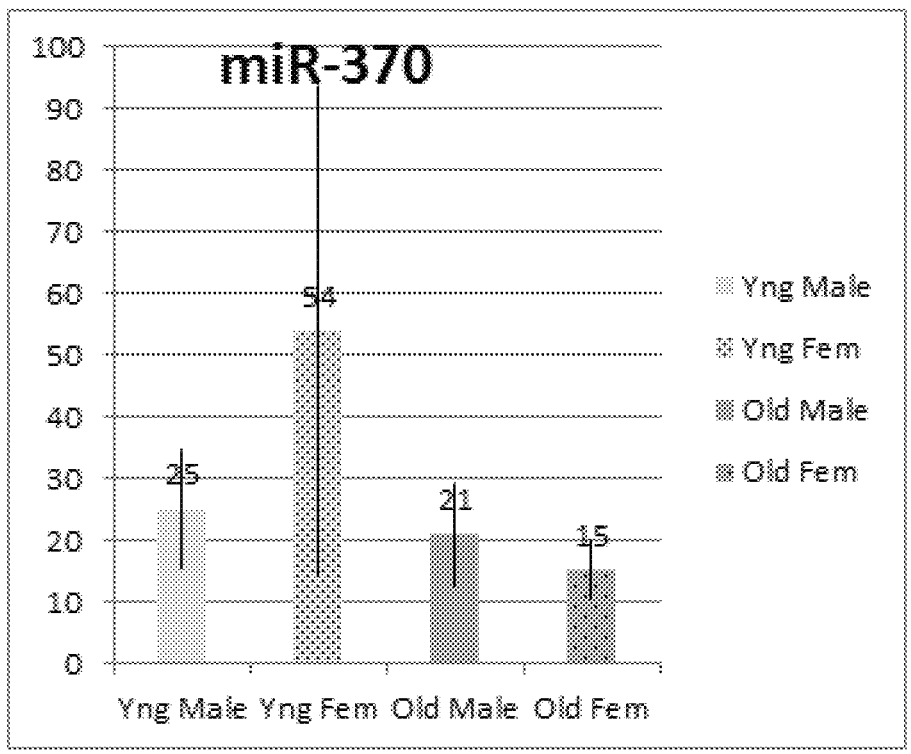
Figure 1E:
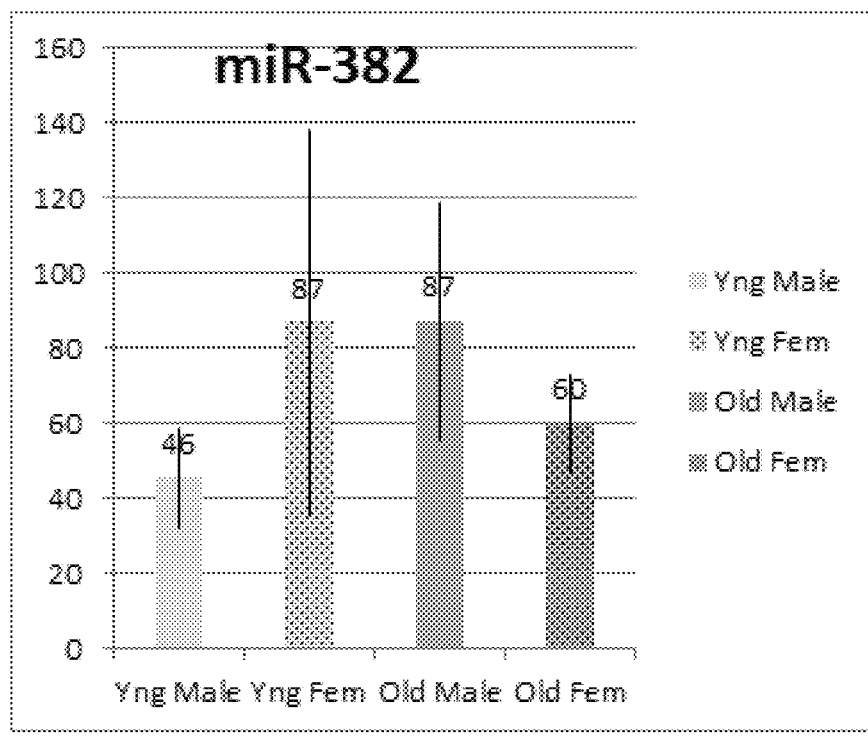
Figure 1F:
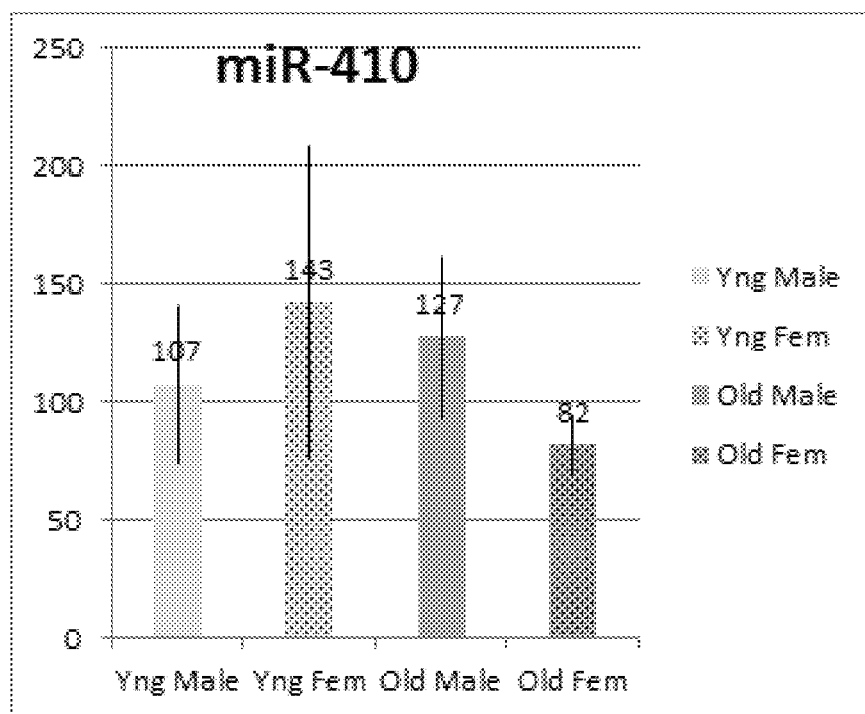
Figure 1G:
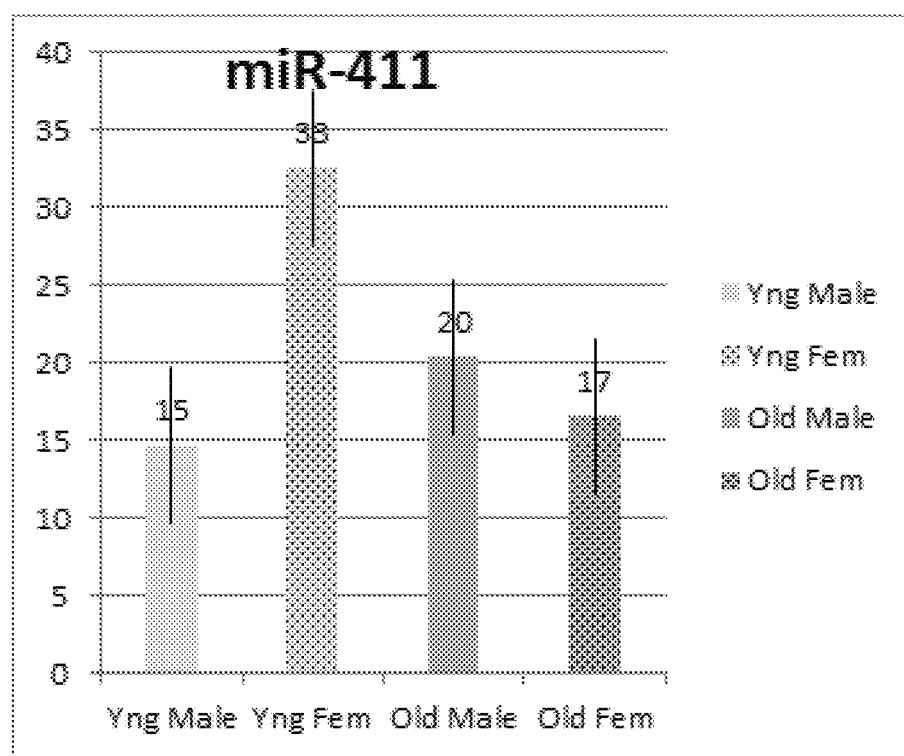
Figure 1H:
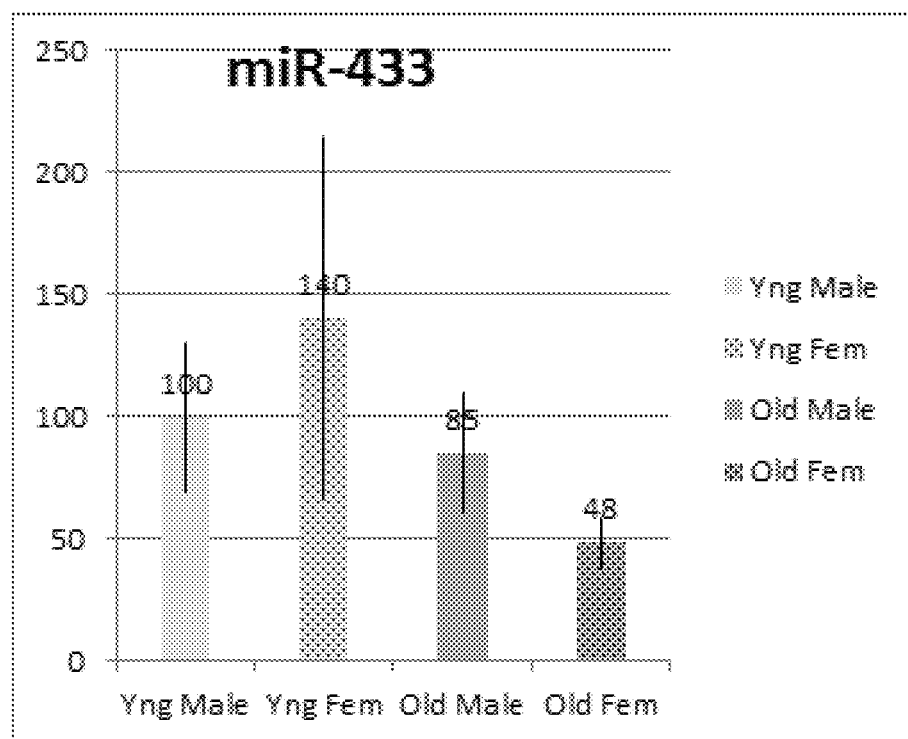
Figure 1I:
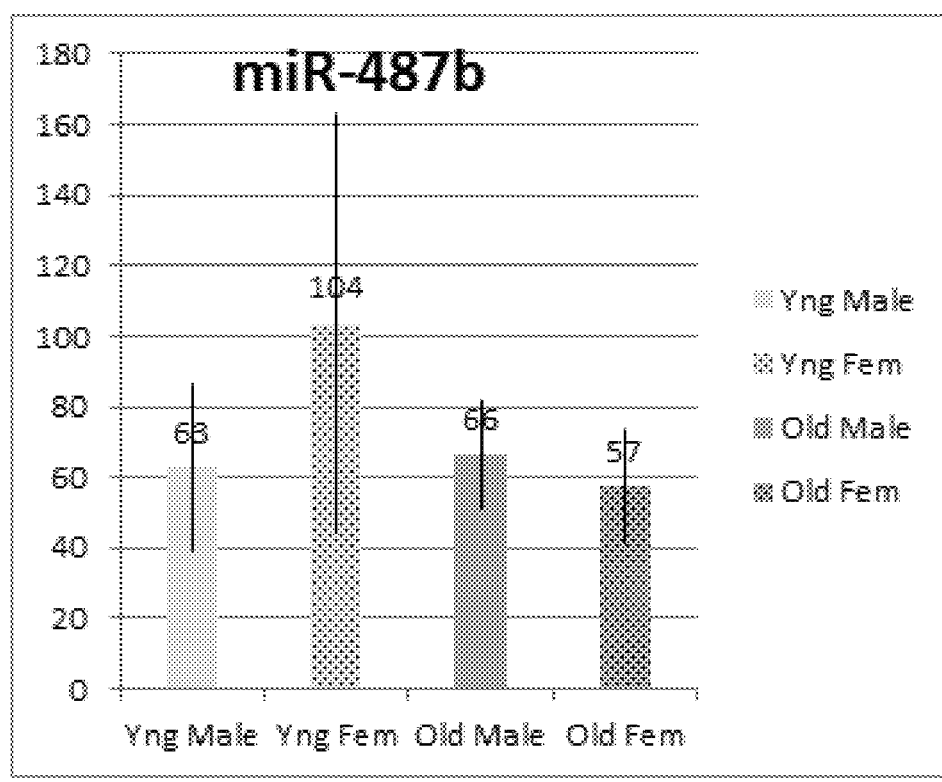
Figure 2A:
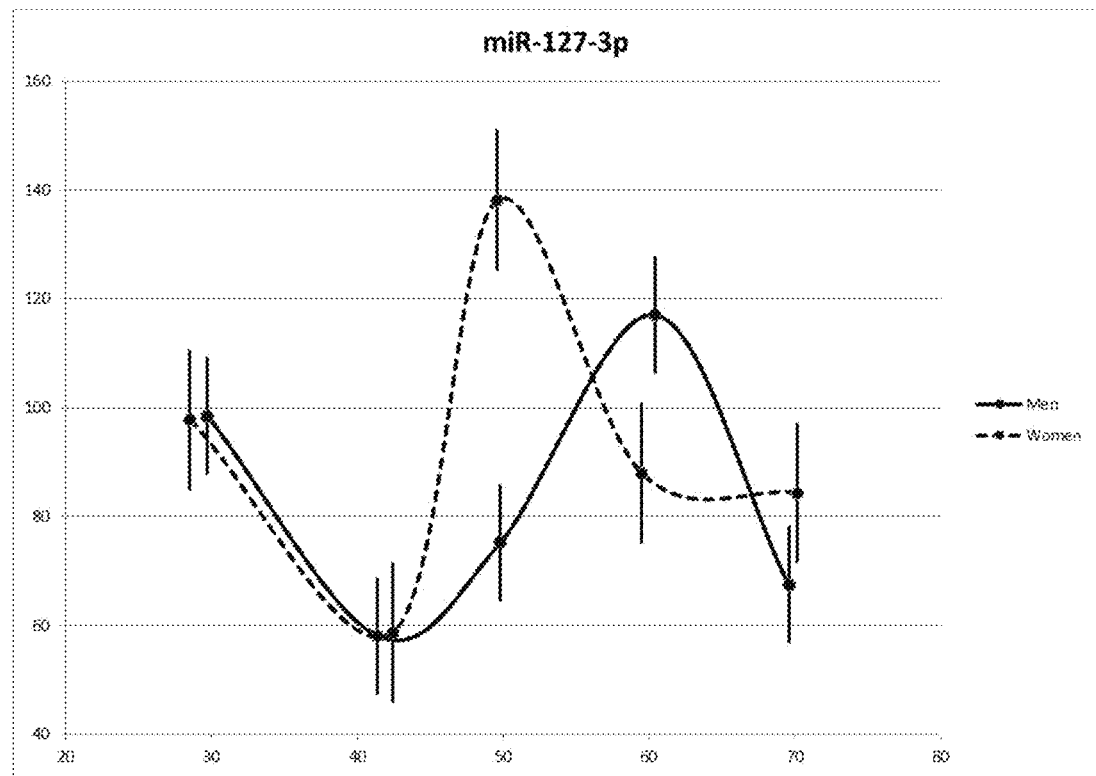
FIGS. 2A-H show age-dependent changes in plasma concentrations of miR-134 family members in male and female participants. Y axis indicates numbers of miRNA copies per 1 µl of plasma.
Figure 2B:
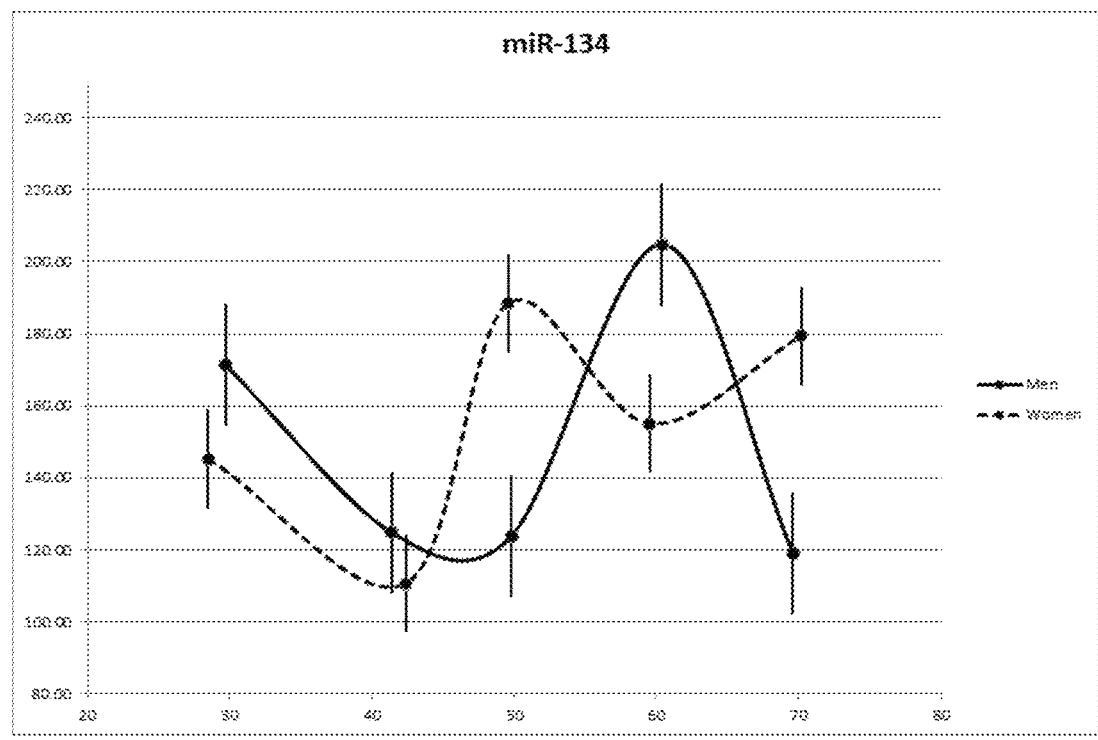
Figure 2C:
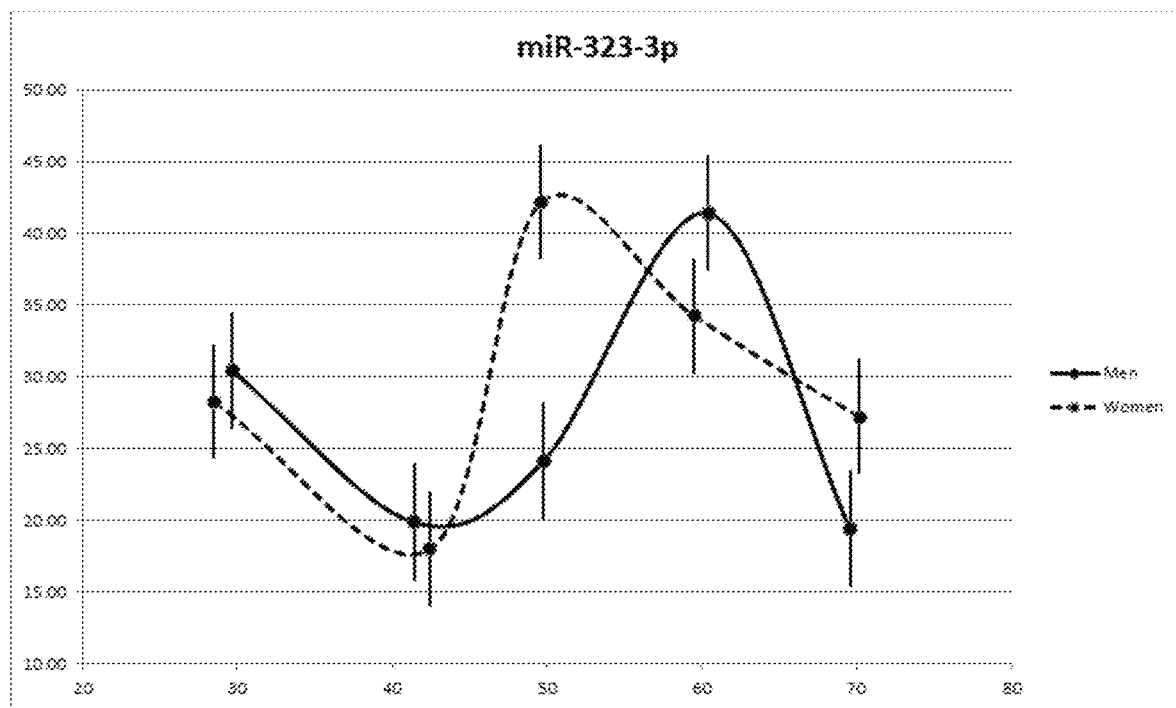
Figure 2D:
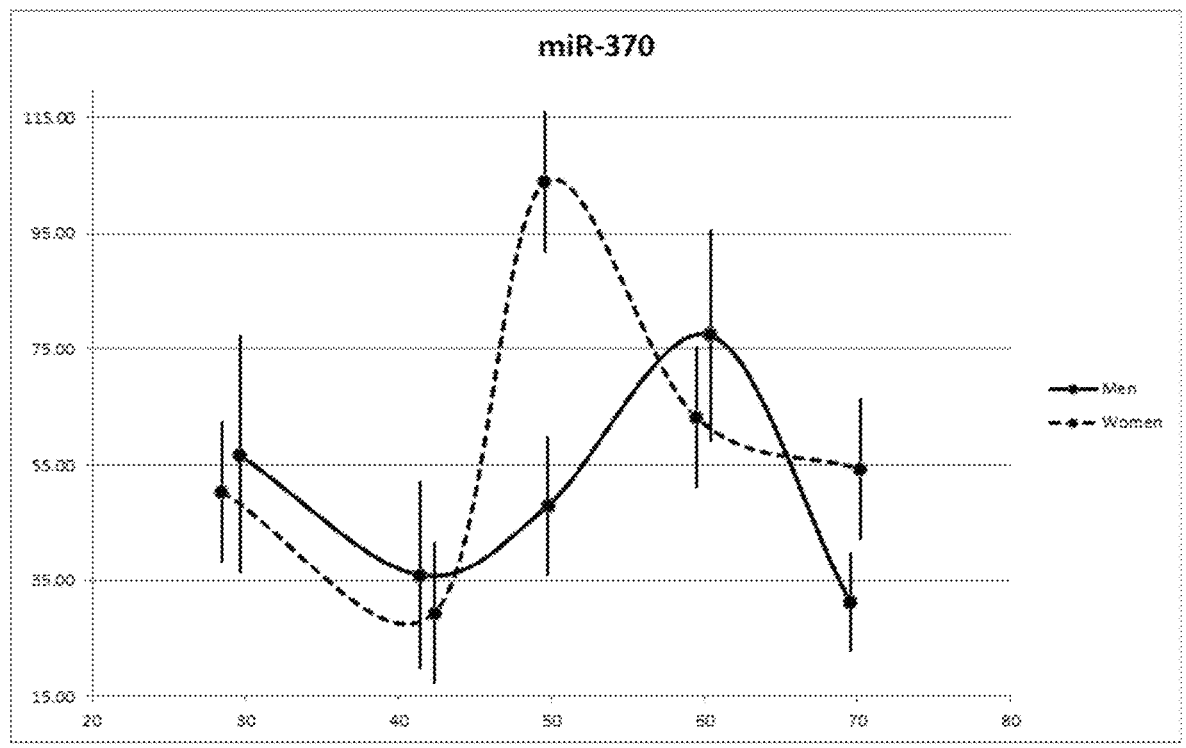
Figure 2E:
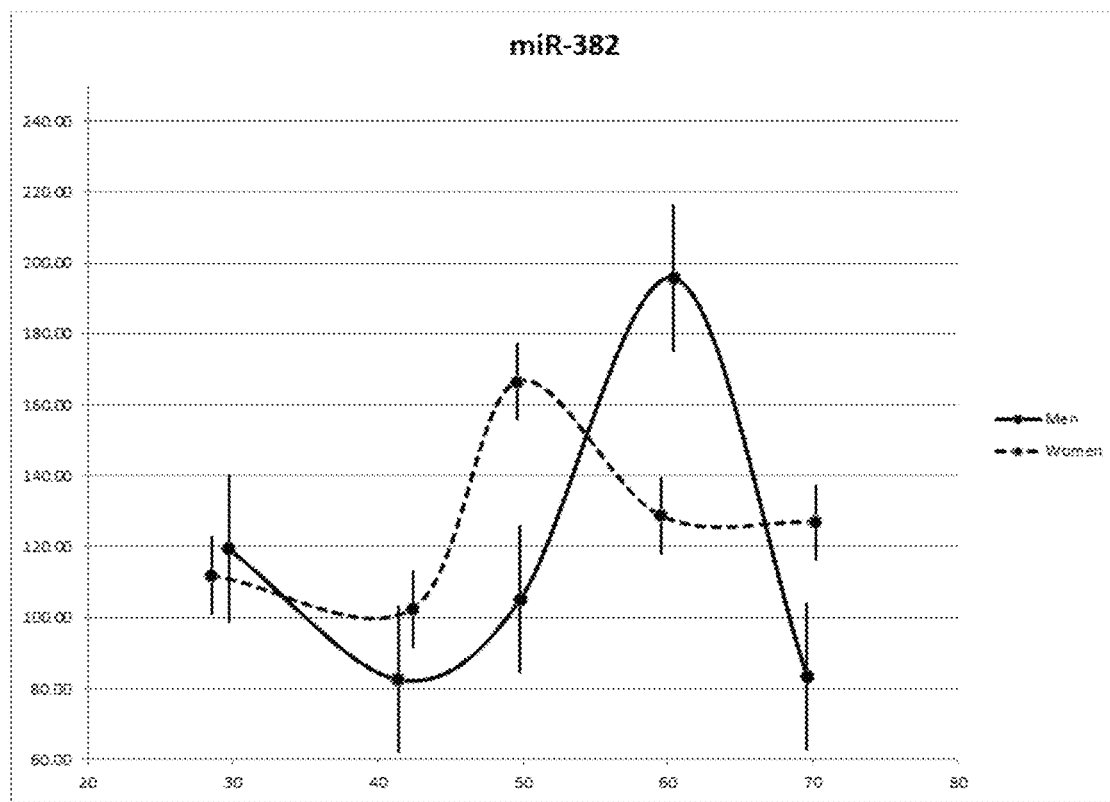
Figure 2F:
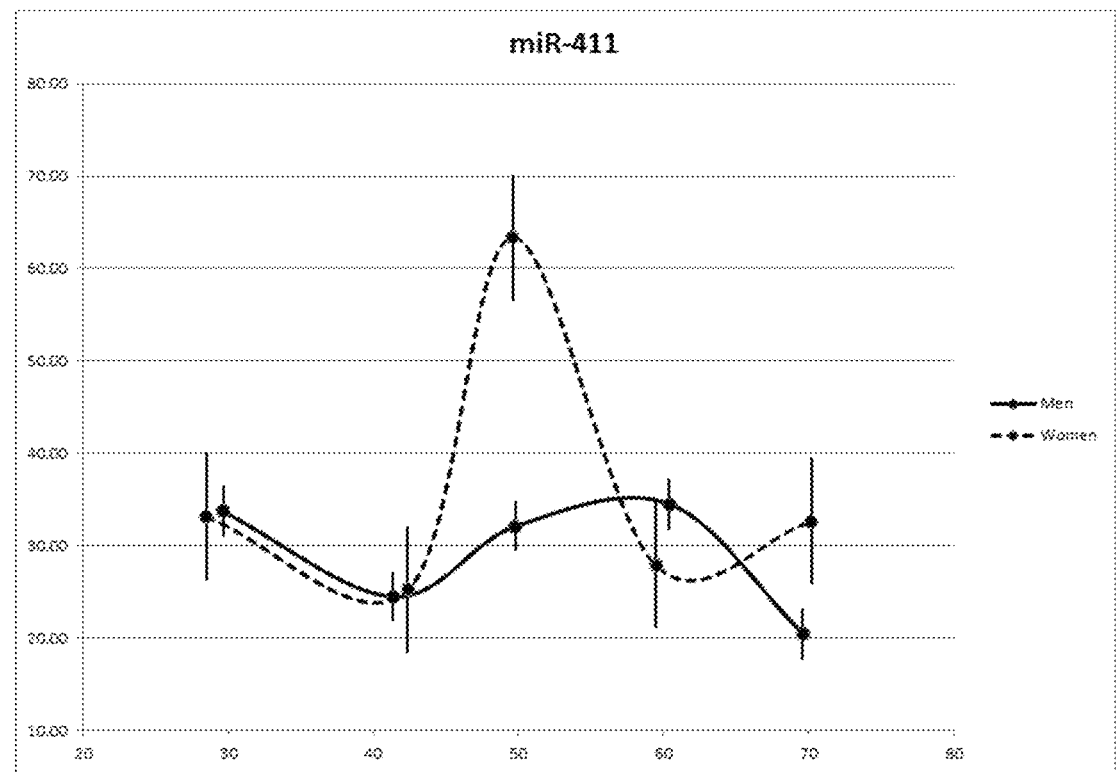
Figure 2G:
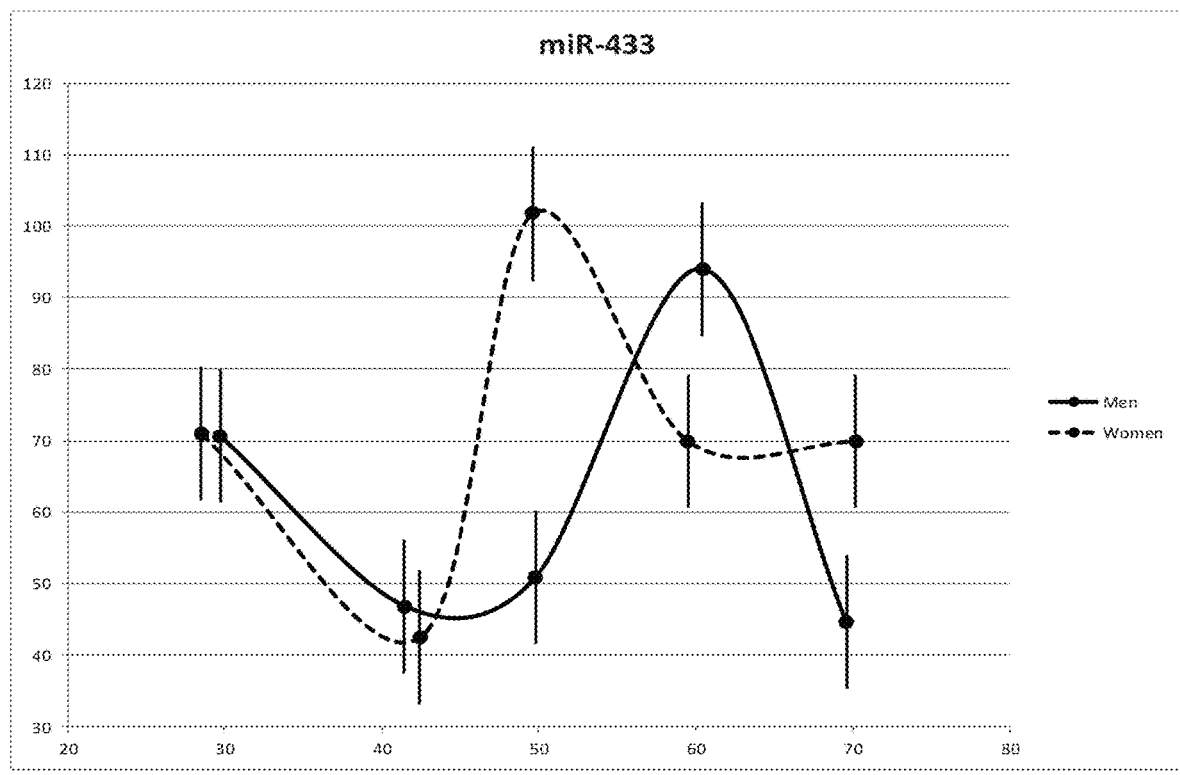
Figure 2H:
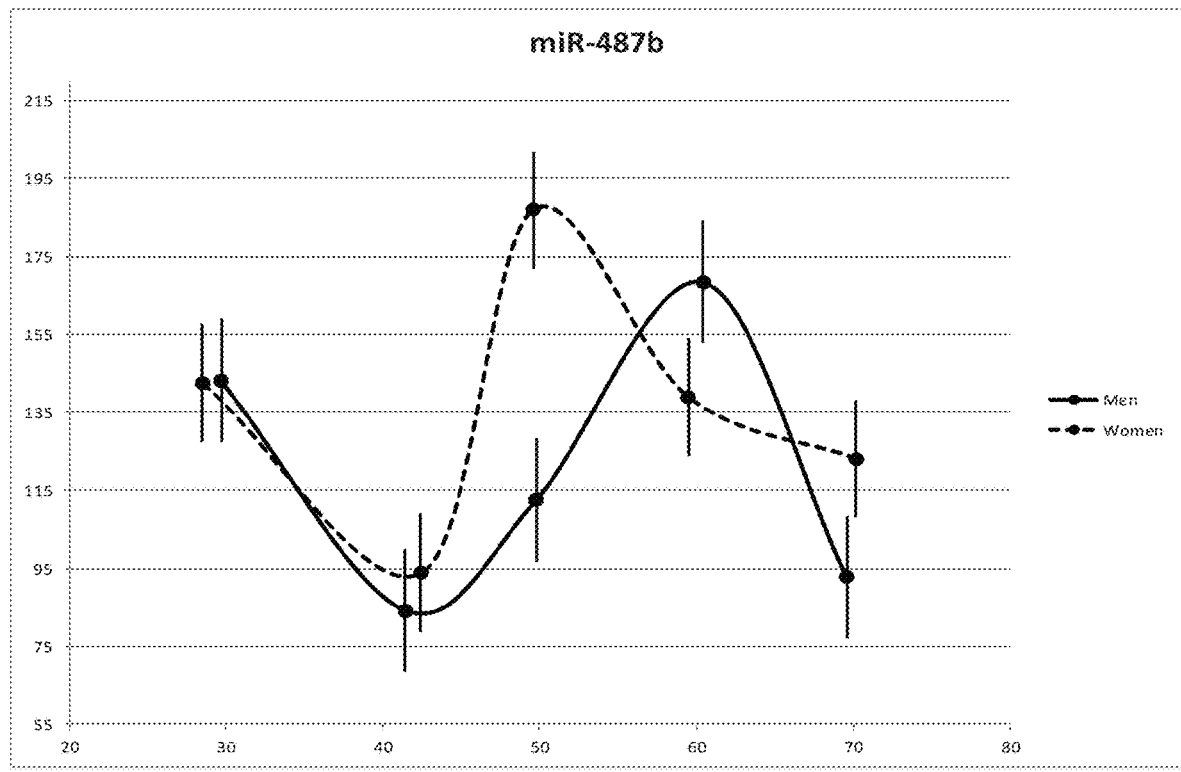
Figure 3A:
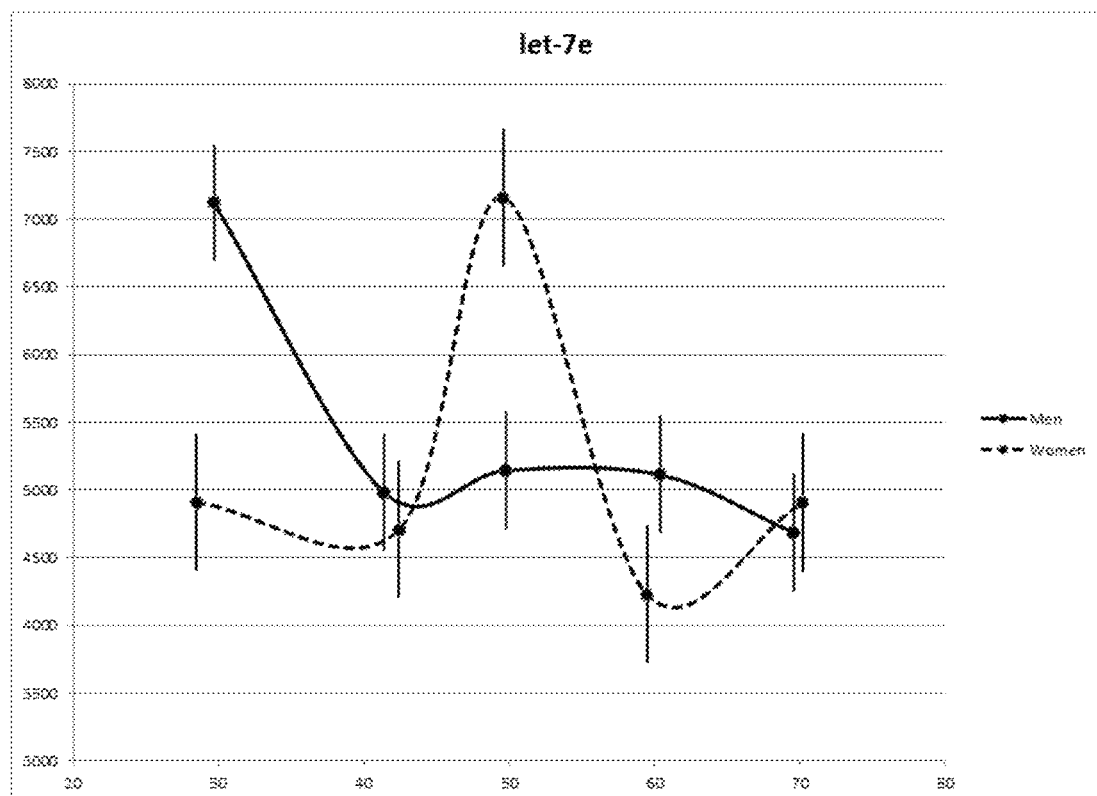
FIGS. 3A-F show age-dependent changes in plasma concentrations of miR-132 family members in male and female participants. Y axis indicates numbers of miRNA copies per 1 µl of plasma.
Figure 3B:
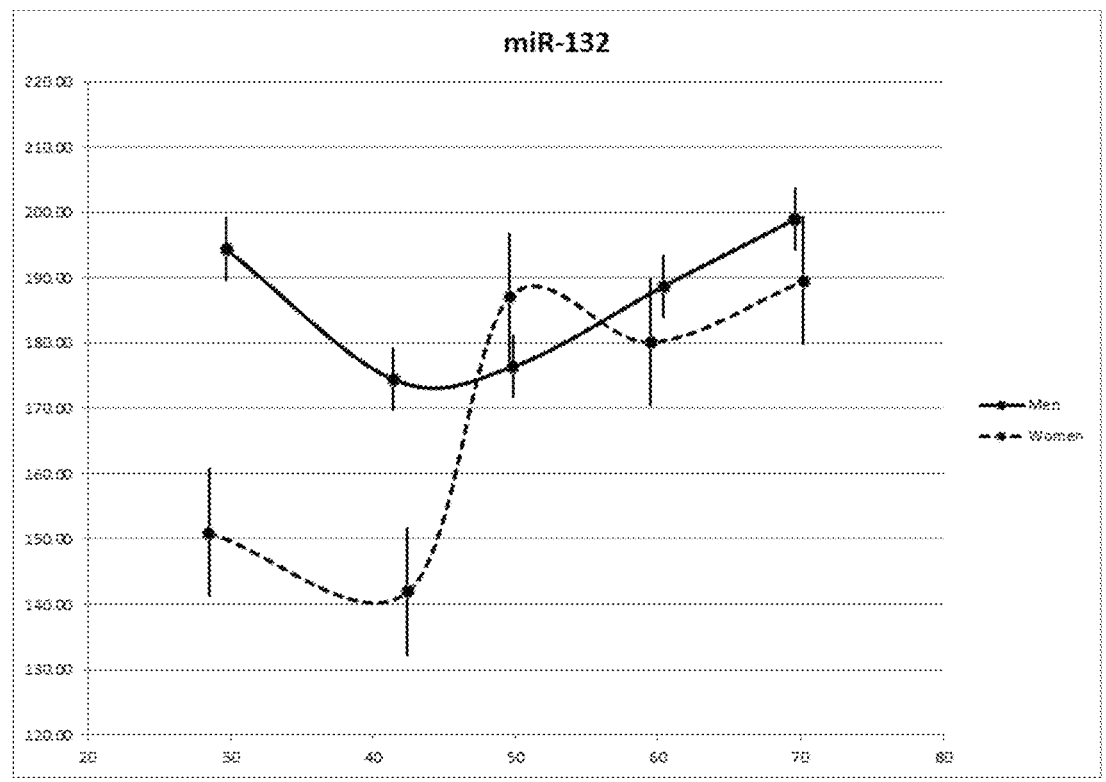
Figure 3C:
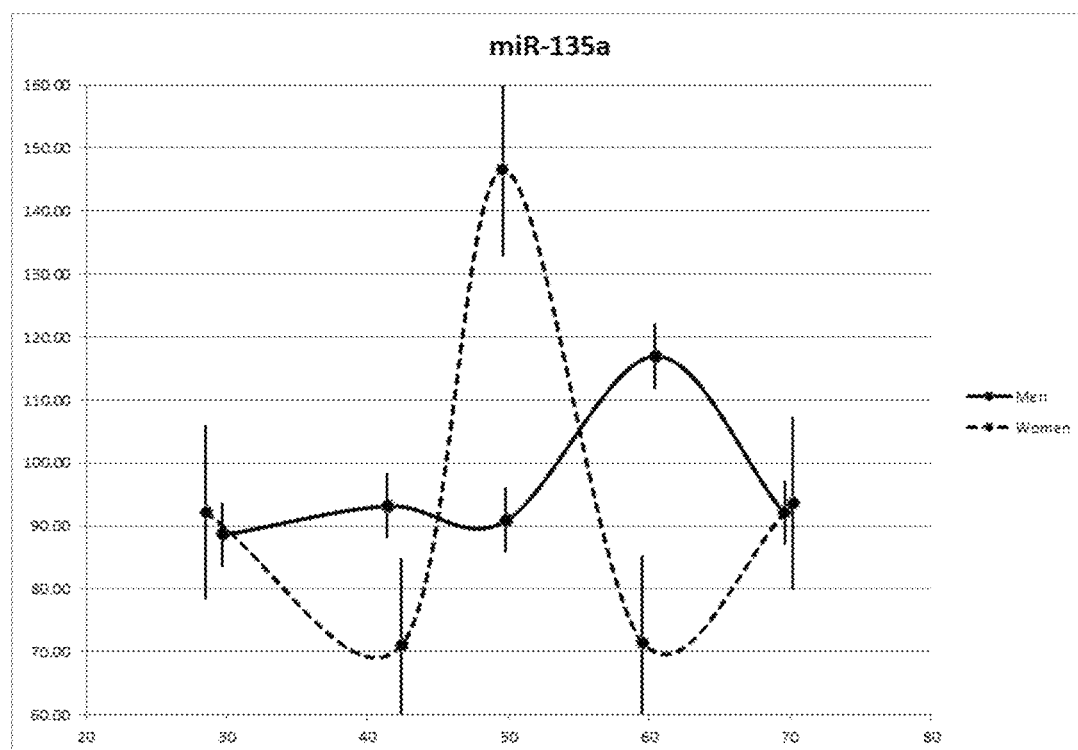
Figure 3D:
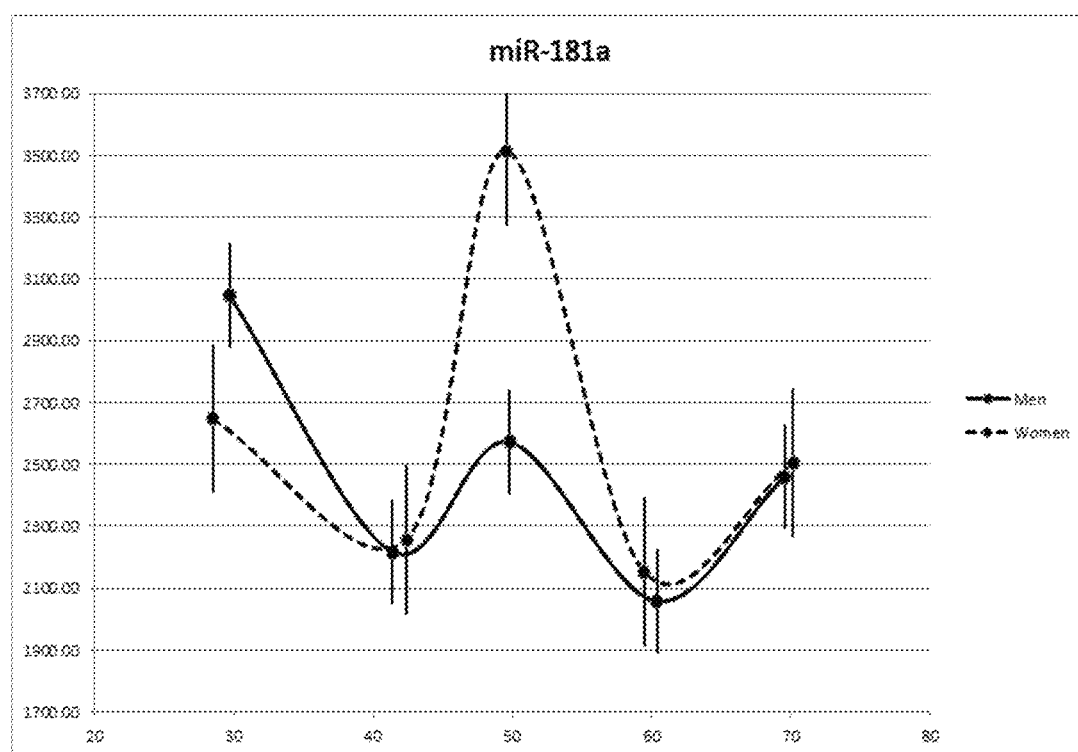
Figure 3E:
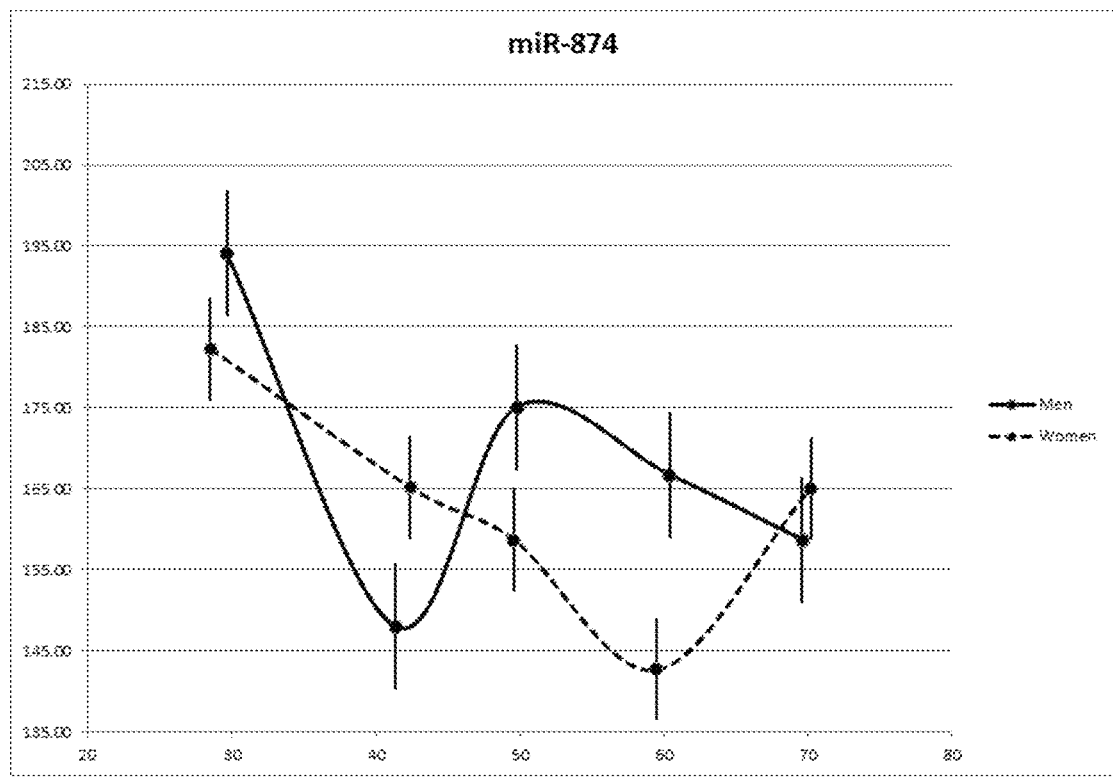
Figure 3F:
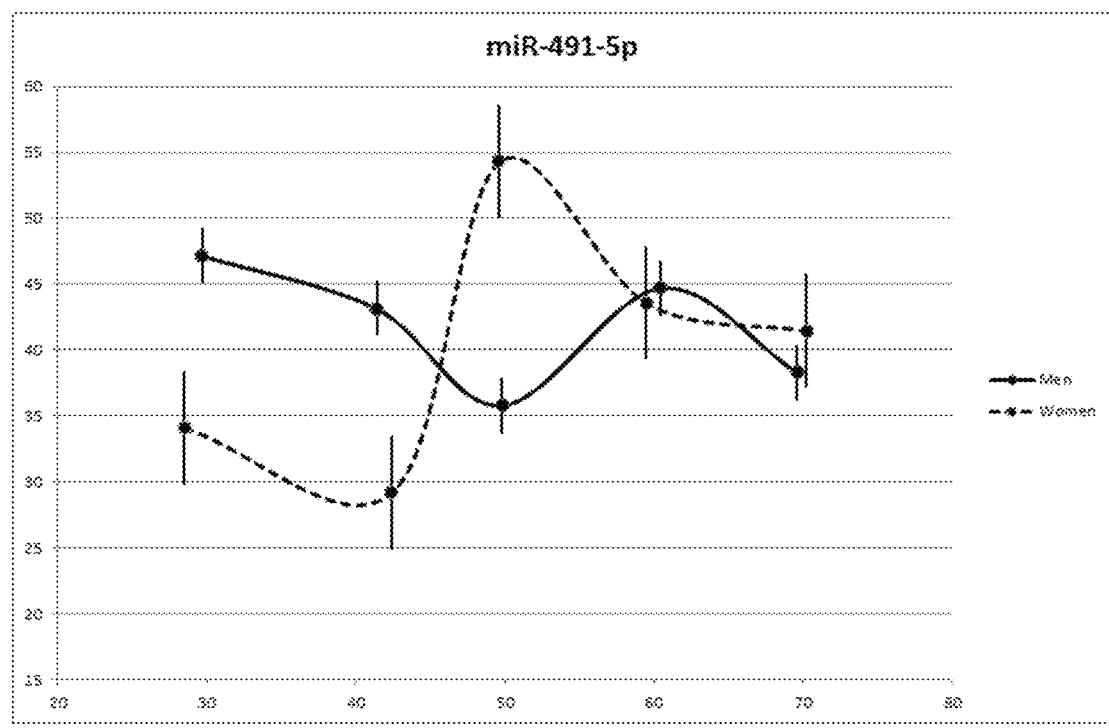
Figure 4A:
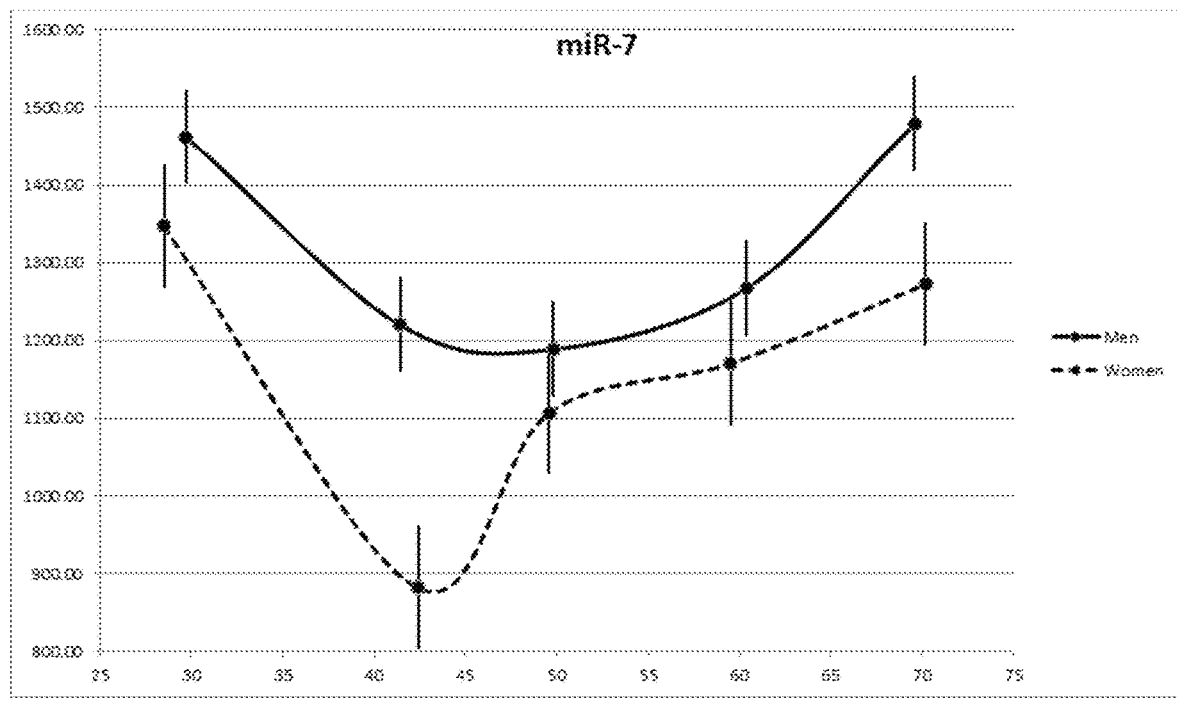
FIGS. 4A-E show age-dependent changes in plasma concentrations of miRNAs that do not belong to the miR-132 and miR-134 families in male and female participants. Y axis indicates numbers of miRNA copies per 1 µl of plasma.
Figure 4B:
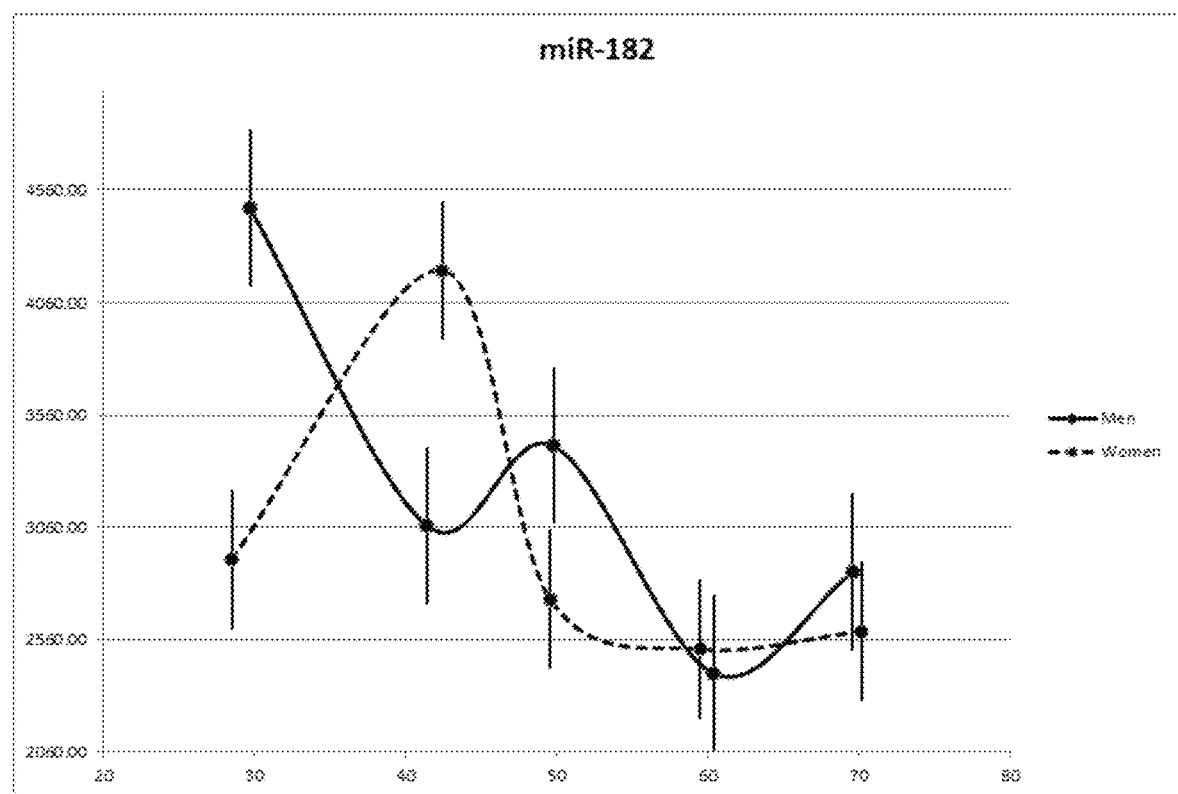
Figure 4C:
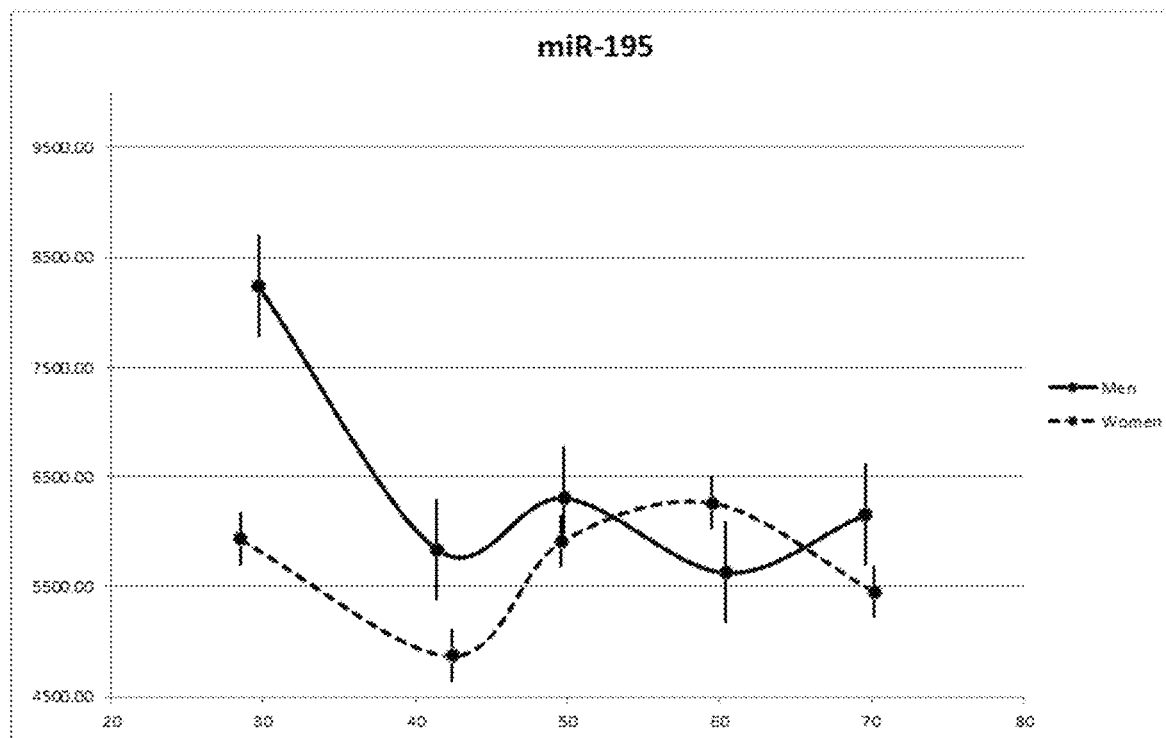
Figure 4D:
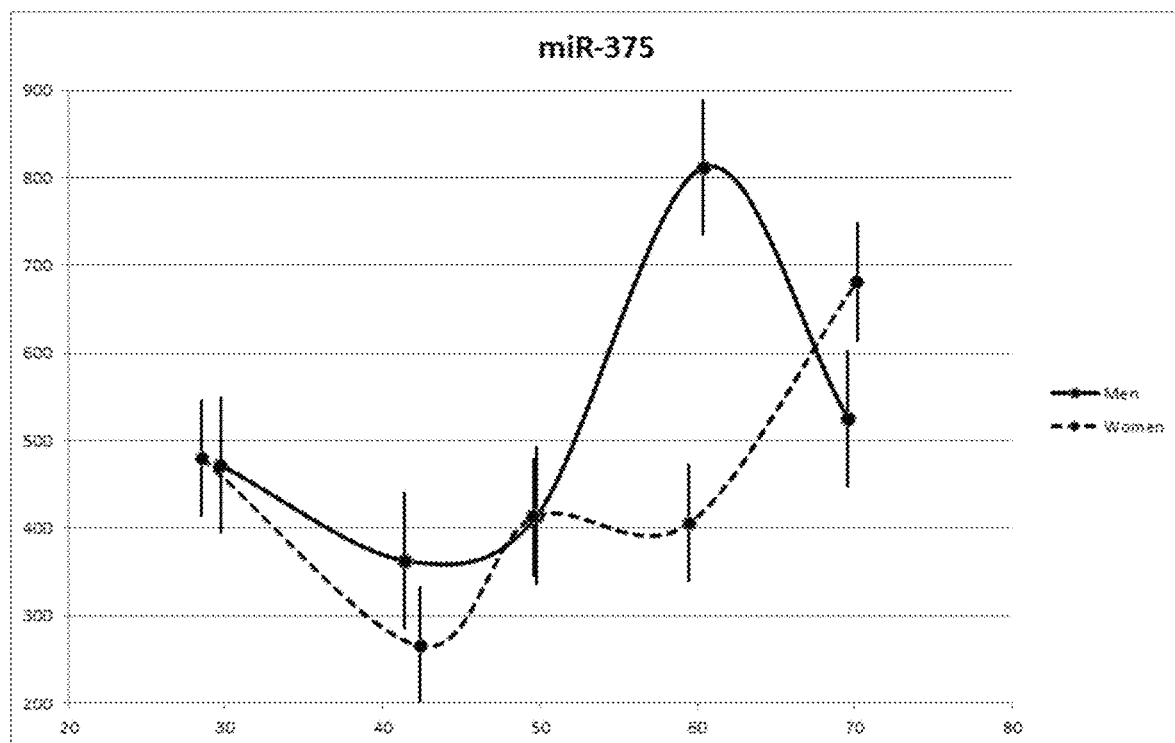
Figure 4E:
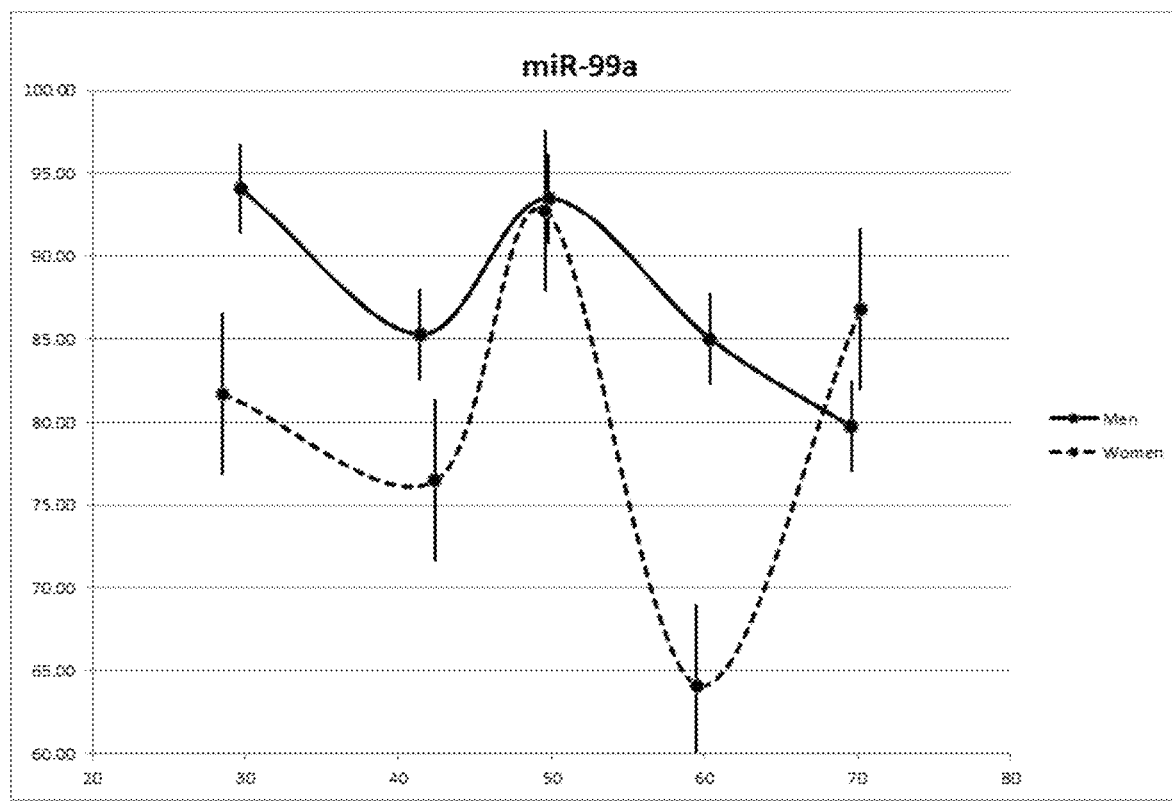

One of the major impediments to the development of pharmaceutical, genetic or nutritional interventions aimed at retarding the aging process is the lack of a molecular method for measuring the aging process in humans or experimental animals. A suitable biomarker of the aging process should reflect biological age (physiological condition) as opposed to chronological age. Additionally, the biomarker should be amenable to quantitation, and reflect aging-related alterations at the molecular level in the cells, tissues, organs and/or organ systems under study. Importantly, any such biomarker must be validated with the use of a model of retarded aging.

Aging is currently believed to be a result of cell autonomous processes, such as accumulation of DNA mutations and abnormal methylation, protein defects and shortening of telomeres, leading to inhibition of cellular proliferation and death of non-dividing terminally differentiated cells (e.g., neurons and cardiomyocytes) on the one hand and/or tumor development on the other. Numerous data support this concept.

One phenomenon, namely, cell death, clearly plays an important role in aging and aging-associated diseases. The idea of the existence of a genetic cell death program in multicellular eukaryotes, its evolutionary origin and its roles in morphogenesis and regular changes in the cellular populations in both embryogenesis and adult individuals was proposed more than 35 years ago [Umansky S R. The genetic program of cell death. Hypothesis and some applications: transformation, carcinogenesis, ageing. J Theor Biol. 1982; 97:591-602.]. Very soon after, this hypothesis was confirmed by the discovery of genes whose products were involved in the cell death program [Ellis H M, Horvitz H R. Genetic control of programmed cell death in the nematode C. elegans. Cell. 1986; 44:817-829; Korsmeyer S J, et al. Bcl-2: B cell life, death and neoplasia. Curr Top Microbiol Immunol. 1990; 166:203-207; Debatin K M, et al. Monoclonal-antibody-mediated apoptosis in adult T-cell leukaemia. Lancet. 1990; 335:497-500, Horvitz H R, Shaham S, Hengartner M O. The genetics of programmed cell death in the nematode *Caenorhabditis elegans*. Cold Spring Harb Symp Quant Biol. 1994; 59:377-385]. In addition, the roles of this program in carcinogenesis and aging were postulated. It was hypothesized that "one of the functions of the cell death program is to eliminate constantly appearing cells with oncogenic features. Hence, for the cell to become malignant two events are necessary, oncogenic mutation and change of the cell death program [Umansky S R. The genetic program of cell death. Hypothesis and some applications: transformation, carcinogenesis, ageing. J Theor Biol. 1982; 97:591-602; Eliyahu D, et al. Wild-type p53 can inhibit oncogene-mediated focus formation. Proc Natl Acad Sci USA. 1989; 86:8763-8767; Oren M. The involvement of oncogenes and tumor suppressor genes in the control of apoptosis. Cancer Metastasis Rev. 1992; 11:141-148].

Aging is also believed to be a result of a central program, which is switching on at specific stage of organism development. Parabiotic effects of blood or plasma transfusion from young to old animals and vice versa support this idea [Villeda S A, et al. Young blood reverses age-related impairments in cognitive function and synaptic plasticity in mice. Nat Med. 2014; 20:659-663; Middeldorp J, et al. Preclinical Assessment of Young Blood Plasma for Alzheimer Disease. JAMA Neurol. 2016; 73:1325-1333; Horowitz A M, Villeda S A. Therapeutic potential of systemic brain rejuvenation strategies for neurodegenerative disease. F1000Res. 2017; 6:1291; Rebo J, et al. A single heterochronic blood exchange reveals rapid inhibition of multiple tissues by old blood. Nat Commun. 2016; 7:13363-13373].

Another interesting aspect is inverse comorbidity of cancer and Alzheimer's disease (AD). Prospective and retrospective studies performed in different countries have convincingly demonstrated that the chances of developing cancer are significantly lower than average for patients with AD and other neurodegenerative diseases. Similarly, cancer survivors have lower chances of developing AD (Driver J A, et al. Inverse association between cancer and Alzheimer's disease: results from the Framingham Heart Study. BMJ 2012; 344:e1442-e1442; Ibáñez K, et al. Molecular evidence for the inverse comorbidity between central nervous system disorders and cancers detected by transcriptomic meta-analyses. PLoS Genet. 2014; 10:e1004173; Tabarés-Seisdedos R, Rubenstein J L. Inverse cancer comorbidity: a serendipitous opportunity to gain insight into CNS disorders. Nat Rev Neurosci. 2013; 14:293-304; Musicco M, Adorni F, et al. Inverse occurrence of cancer and Alzheimer disease: A population-based incidence study. Neurology 2013; 81:322-328; Papageorgakopoulos T N, et al. The association between Alzheimer's disease and cancer: Systematic review—Meta-analysis. Hell J Nucl Med. 2017: 20 Suppl: 45-57; Bajaj A, Driver J A, Schernhammer E S. Parkinson's disease and cancer risk: a systematic review and meta-analysis. Cancer causes & control: Cancer Causes Control. 2010; 21: 697-707;).

The present inventors have hypothesized that there are two miRNA-associated factors that can explain why subjects with a neurodegenerative disease such as AD have a lower chance of developing cancer, and subjects who survive cancer have a lower probability of developing a neurodegenerative disease such as AD. First, if the pituitary gland (PG) secretes more pro-apoptotic miRNAs (e.g., Bcl-2-inhibiting miRNAs), this can decrease the chance of developing cancer but increase the chances of developing neuro- and other degenerative diseases, and vice versa; higher levels of anti-apoptotic miRNAs stimulate cancer development but decrease the chance of developing AD. The present inventors have also hypothesized that many synapse/dendrite-enriched miRNAs that are released in the early stages of neurodegenerative diseases due to neurite dysfunction and destruction and then circulate in the bloodstream are pro-apoptotic, which decreases the chance of developing cancer. On the other hand, tumor cells may secrete anti-apoptotic miRNAs that can inhibit degenerative processes, although the ability of these miRNAs to reach the brain is questionable.

Another important aspect is higher AD morbidity and lower frequency of many common types of cancer for women vs. men (Cook M B, McGlynn K A, Devesa S S, Freedman N D, Anderson W F. Sex disparities in cancer mortality and survival. Cancer Epidemiol Biomarkers Prev. 2011; 20:1629-1637; Ronquillo J G, Baer M R, Lester W T. Sex-specific patterns and differences in dementia and Alzheimer's disease using informatics approaches. J Women Aging. 2016; 28:403-411; Snyder et al. Sex biology contributions to vulnerability to Alzheimer's disease: A think tank convened by the Women's Alzheimer's Research Initiative. Alzheimers Dement. 2016; 12:1186-1196; Xu J, et al. Mortality in the United States, 2015. NCHS Data Brief. 2016; 267:1-7). Two-thirds of Americans living with AD dementia are women, and neither their longer lifespans nor differences in lifestyle compared to men can explain these numbers. It has been suggested that the higher frequency of female AD morbidity is caused by increased chances of AD initiation earlier in life due to menopause, although the mechanisms underlying this phenomenon are not clear [Nemeth V L, et al. Gender-Specific Degeneration of Dementia-Related Subcortical Structures Throughout the Lifespan. J Alzheimers Dis. 2017; 55:865-880; Mosconi L, et al. Sex differences in Alzheimer risk: Brain imaging of endocrine vs chronologic aging. Neurology. 2017; 89:1382-1390;]. Without wishing to be bound by theory, the present inventors' data and hypothesis explains these sex (gender) differences by changes in the spectrum of secreted PG miRNA hormones from pro-developmental to anti-carcinogenic, changes that are associated with decreased levels of estrogen. These changes in the spectrum of miRNAs secreted from PG may decrease the chances of carcinogenesis and increase the chances of neurodegenerative processes. Due to menopause, all of these processes can start in females about 10 years earlier than in males.

Longer live expectancy for women vs. men [Yin S. Gender Disparities in Health and Mortality. Population Reference Bureau. 2007; World Health Statistics, WHO, 2016 http://www.who.int/gho/publications/world_health-_statistics/2016/en/) and much lower sex-dependent differences, if any, in other mammalian species can be also explained by the earlier switch in the spectrum of PG-secreted miRNA hormones in women than in men. which results in more effective elimination of cells with dangerous mutations and other abnormalities and decreased chances of cancer due to menopause.

Higher risk of AD and lower risk of cancer has been described for subjects with Down syndrome (Schupf N, et al. Onset of dementia is associated with age at menopause in women with Down's syndrome. Ann Neurol. 2003; 54:433-438; Tabarés-Seisdedos R, et al. No paradox, no progress: inverse cancer comorbidity in people with other complex diseases. Lancet Oncol. 2011; 12: 604-608; Forés-Martos J, et al. A genomic approach to study Down syndrome and cancer inverse comorbidity: untangling the chromosome 21.

Front Physiol. 2015; 6:10; Hartley D, et al. Down syndrome and Alzheimer's disease: Common pathways, common goals. Alzheimers Dement. 2015; 11:700-709). Without wishing to be bound by theory, the present inventors have hypothesized that since menopause in females and the decrease in sex hormone production in male subjects with Down syndrome occur much earlier than in healthy subjects, the switch in the spectrum of PG-secreted miRNAs described above decreases the chances of carcinogenesis and increases the chances of neurodegenerative processes.

The above hypothesis is further supported by a significantly increased life span after hypophysectomy (Everitt A V, Seedsman N J, Jones F. The effects of hypophysectomy and continuous food restriction, begun at ages 70 and 400 days, on collagen aging, proteinuria, incidence of pathology and longevity in the male rat. Mech Ageing Dev. 1980; 12:161-172; Powers R W 3rd, Harrison D E, Flurkey K. Pituitary removal in adult mice increases life span. Mech Ageing Dev. 2006; 127:658-659), and rejuvenation effect of blood or plasma transfusion from young donors to elderly recipients (Villeda et al. Nat. Med., Young blood reverses age-related impairments in cognitive function and synaptic plasticity in mice. Nat Med. 2014; 20:659-663; Middeldorp et al. Preclinical Assessment of Young Blood Plasma for Alzheimer Disease. JAMA Neurol. 2016; 73:1325-1333) and the opposite effect of blood/plasma transfusion from old to young subjects (Rebo et al. A single heterochronic blood exchange reveals rapid inhibition of multiple tissues by old blood. Nat Commun. 2016; 7:13363-13373) in animal models (parabiosis), etc. Without wishing to be bound by theory, it is quite possible that the effect of plasma transfusion is at least partially caused by circulating miRNAs. The inhibitory effect of plasma-heating does not exclude miRNA participation since after such treatment, the miRNAs may be degraded in the circulation by RNases.

A high interest to existence of central mechanisms regulating aging-related processes and longevity is explained by very important potential practical applications of modifying these mechanisms, which could lead to healthier old age and longer lifespan in general.

Critical for developing and testing approaches to sustaining healthy living and delaying aging is the development and validation of minimally invasive, cost-effective biomarkers of aging. In addition, quantitative definition of biomarker ranges that are characteristic of normal aging is also important for early detection of aging-related diseases. For example, synapse dysfunction and loss, ultimately followed by neuronal death, accompany normal aging. However, rapid progression of these processes in a particular brain region could be an early indication of a neurodegenerative disease affecting this region. The same is true for other organs and tissues.

The American Federation for Aging Research and the European MARK-AGE Consortium propose several criteria for a successful biomarker of aging: (1) it must predict the rate of aging and assess where a person is in his/her lifespan better than the person's chronological age; (2) an assay for measuring such a biomarker should be minimally invasive; and (3) the biomarker should be useful in animal models, as well as in humans, since preliminary testing of essentially all drug candidates and many therapeutic regimens is performed in non-human subjects. Traditional biomarkers of aging are based on evaluations of an individual's general physical status, function and health of various organ systems (cardiovascular, pulmonary), cognitive function, etc. The potentially promising biomarkers of aging, which are currently being investigated, can be divided into several general groups: (1) genetic biomarkers, including the length of telomeres in lymphocytes and other cells, age-related epigenetic changes mainly in DNA methylation, and changes in mitochondrial DNA; (2) protein-based biomarkers, including markers based on protein glycation and levels of metal-binding proteins; (3) metabolic parameters, such as hormones, lipids, and creatinine; (4) immunological and inflammatory markers, including concentrations of immunoglobulins, cytokines, and C-reactive protein in the bloodstream; (5) markers of oxidative stress; and (6) imaging biomarkers capable of registering aging-associated brain changes [Burkle A, et al. MARK-AGE biomarkers of ageing. Mech. Ageing Dev. 2015; 151:13-17; Ciccarone F, Tagliatesta S, Caiafa P, Zampieri M. DNA methylation dynamics in aging: how far are we from understanding the mechanisms? Mech Ageing Dev. 2017; pii: S0047-6374(17) 30267-1]. To date, there is no biomarker that satisfies the three criteria listed above; some biomarker candidates are not optimal for broad clinical use because they are highly variable, invasive, laborious and/or expensive or they cannot be used in animal models.

ADDITIONAL REFERENCES

1. *Inverse comorbidity of cancer and Alzheimer's and other neurodegenerative diseases* [Driver J A, Beiser A, Au R, Kreger B E, Splansky G L, Kurth T, Kiel D P, Lu K P, Seshadri S, Wolf P A. Inverse association between cancer and Alzheimer's disease: results from the Framingham Heart Study. BMJ 2012; 344:e1442-e1442; Ibáñez K, Boullosa C, Tabarés-Seisdedos R, Baudot A, Valencia A. Molecular evidence for the inverse comorbidity between central nervous system disorders and cancers detected by transcriptomic meta-analyses. PLoS Genet. 2014; 10:e1004173; Tabarés-Seisdedos R, Rubenstein J L. Inverse cancer comorbidity: a serendipitous opportunity to gain insight into CNS disorders. Nat Rev Neurosci. 2013; 14:293-304; Musicco M, Adorni F, Di Santo S, Prinelli F, Pettenati C, Caltagirone C, Palmer K, Russo A. Inverse occurrence of cancer and Alzheimer disease: A population-based incidence study. Neurology 2013; 81:322-328; Papageorgakopoulos T N, Moraitou D, Papanikolaou M, Tsolaki M. The association between Alzheimer's disease and cancer: Systematic review—Meta-analysis. Hell J Nucl Med. 2017: 20 Suppl: 45-57; Bajaj A, Driver J A, Schernhammer E S. Parkinson's disease and cancer risk: a systematic review and meta-analysis. Cancer causes & control: Cancer Causes Control. 2010; 21:697-707].

2. *Longer life expectancy for women vs. men and much lower gender-dependent differences, if any, in other mammals* [Smith D W. Is greater female longevity a general finding among animals? Biol Rev Camb Philos Soc. 1989; 64:1-12; Yin S. Gender Disparities in Health and Mortality. Population Reference Bureau. 2007; Austad S N, Bartke A. Sex Differences in Longevity and in Responses to Anti-Aging Interventions: A Mini-Review. Gerontology. 2015; 62:40-46; Austad S N, Fisher K E. Sex Differences in Lifespan. Cell Metab. 2016; 23:1022-1033; World Health Statistics. WHO 2016. http://www.who.int/gho/publications/world_health_statistics/2016/en/].

3. *Higher AD morbidity and lower frequency of many common types of cancer in women vs. men* [Xu J, Murphy S L, Kochanek K D, Arias E. Mortality in the United States, 2015. NCHS Data Brief. 2016; 267:1-7; Cook M B, McGlynn K A, Devesa S S, Freedman N D, Anderson W F. Sex disparities in cancer mortality and survival.

Cancer Epidemiol Biomarkers Prev. 2011; 20:1629-1637; Ronquillo J G, Baer M R, Lester W T. Sex-specific patterns and differences in dementia and Alzheimer's disease using informatics approaches. J Women Aging. 2016; 28:403-411]. Snyder et al. Sex biology contributions to vulnerability to Alzheimer's disease: A think tank convened by the Women's Alzheimer's Research Initiative. Alzheimers Dement. 2016; 12:1186-1196].

4. *Higher risk of AD and lower risk of cancer in subjects with Down syndrome* [Nixon D W. Down Syndrome, Obesity, Alzheimer's Disease, and Cancer: A Brief Review and Hypothesis. Brain Sci. 2018; 8 pii: E53; Schupf N, Pang D, Patel B N, Silverman W, Schubert R, Lai F, Kline J K, Stern Y, Ferin M, Tycko B, Mayeux R. Onset of dementia is associated with age at menopause in women with Down's syndrome. Ann Neurol. 2003; 54:433-438; Tabarés-Seisdedos R, Dumont N, Baudot A, Valderas J M, Climent J, Valencia A, Crespo-Facorro B, Vieta E, Gómez-Beneyto M, Martínez S, Rubenstein J L. No paradox, no progress: inverse cancer comorbidity in people with other complex diseases. Lancet Oncol. 2011; 12: 604-608; Forés-Martos J, Cervera-Vidal R, Chirivella E, Ramos-Jarero A, Climent J. A genomic approach to study Down syndrome and cancer inverse comorbidity: untangling the chromosome 21. Front Physiol. 2015; 6:10; Hartley D, Blumenthal T, Carrillo M, DiPaolo G, Esralew L, Gardiner K, Granholm A C, Iqbal K, Krams M, Lemere C, Lott I, Mobley W, Ness S, et al. Down syndrome and Alzheimer's disease: Common pathways, common goals. Alzheimers Dement. 2015; 11:700-709].

5. *Increased life span after hypophysectomy* [Everitt A V, Seedsman N J, Jones F. The effects of hypophysectomy and continuous food restriction, begun at ages 70 and 400 days, on collagen aging, proteinuria, incidence of pathology and longevity in the male rat. Mech Ageing Dev. 1980; 12:161-172; Powers R W 3rd, Harrison D E, Flurkey K. Pituitary removal in adult mice increases life span. Mech Ageing Dev. 2006; 127:658-659].

6. *Rejuvenative effect of blood or plasma transfusion from young donors to elderly recipients in animal models* [Villeda S A, Plambeck K E, Middeldorp J, Castellano J M, Mosher K I, Luo J, Smith L K, Bieri G, Lin K, Berdnik D, Wabl R, Udeochu J, Wheatley E G, et al. Young blood reverses age-related impairments in cognitive function and synaptic plasticity in mice. Nat Med. 2014; 20:659-663; Middeldorp J, Lehallier B, Villeda S A, Miedema S S, Evans E, Czirr E, Zhang H, Luo J, Stan T, Mosher K I, Masliah E, Wyss-Coray T, et al. Preclinical Assessment of Young Blood Plasma for Alzheimer Disease. JAMA Neurol. 2016; 73:1325-1333; Horowitz A M, Villeda S A. Therapeutic potential of systemic brain rejuvenation strategies for neurodegenerative disease. F1000Res. 2017; 6:1291].

7. Aramillo I P, Schäible S, Esser D, Groth M, Frahm C, Priebe S, Baumgart M, Hartmann N, Marthandan S, Menzel U, Müller J, Schmidt S, Ast V, et al. Transcriptomic alterations during ageing reflect the shift from cancer to degenerative diseases in the elderly. Nat Commun. 2018; 9:327.

Without wishing to be bound by theory, the present inventors have hypothesized that pituitary gland (PG), hypothalamus and, perhaps, other endocrine glands, in addition to producing known hormones, can also secrete miRNAs, which perform fine tuning of numerous processes, including apoptosis, autophagy, and insulin, mTOR, Wnt and other signaling pathways. Since the hypothalamus-pituitary gland (PG) axis is regulated by sex hormones, menopause in women and more stepwise changes in circulating sex hormones in men may cause sex-dependent changes in miRNA secretion via the PG. These aging-related changes in the spectrum of secreted miRNAs, e.g. increases in pro-apoptotic and decreases in anti-apoptotic miRNAs, although mild and slow, may lead to progressive switching from stimulation of developmental processes (proliferation, vascularization, etc.) to their inhibition, thus providing tumor-suppressive effects, and to activation of apoptosis and other degenerative processes. Altogether, when combined with age-related accumulation of various defects in terminally differentiated non-dividing cells, changes in the spectrum of secreted miRNAs can result in the manifestation of general aging symptoms, as well as creation of a basis for the initiation and development of various aging-associated diseases. Sex hormone dependent changes in the spectrum of PG/hypothalamus-secreted miRNA hormones may increase chances of apoptosis caused by age-related molecular defect accumulation, and thus, the inventors' hypothesis combines two major concepts of aging: the accumulation of molecular damages and central regulation. The methods described herein may have numerous practical applications, such as the following: (i) aging modification via application of sex hormones under the control of circulating miRNA hormones; (ii) aging modification via separate delivery of respective miRNA hormones (or antisense oligonucleotides to miRNAs) into the brain and/or body blood circulation; (iii) treatment of AD with delivery of anti-apoptotic miRNA hormones (or antisense oligonucleotides to pro-apoptotic miRNAs) to the brain with no cancer activation; and (iv) creation of better animal AD and other aging-associated disease models by introducing artificial menopause.

miRNAs are small molecules (~22 nt), which play important roles in the regulation of target genes by binding to complementary regions of messenger transcripts to repress their translation or regulate degradation (Griffiths-Jones S, et al. miRBase: microRNA sequences, targets and gene nomenclature. Nucleic Acids Res. 2006; 34, Database issue: D140-D144; Bartel D P. MicroRNAs: target recognition and regulatory functions. Cell. 2009; 136:215-233). Frequently, one miRNA can target multiple messenger RNAs (mRNAs) and one mRNA can be regulated by multiple miRNAs targeting different regions of the mRNA 3' UTR (untranslated region). Once bound to an mRNA, miRNA can modulate gene expression and protein production by affecting mRNA translation and stability (Baek et al. Nature. 2008; Selbach et al. Nature. 2008; Ambros. Nature. 2004; Bartel. Cell. 2004; Cullen. Virus Research. 2004; He et al. Nat. Rev. Genet. 2004; and Ying et al. Gene. 2004). Importantly, more than 2000 miRNAs have already been discovered in human cells to date and many of these miRNAs are enriched in particular organ systems, organs, tissues and cell types as summarized in Table 1 (Liang Y, Ridzon D, Wong L, Chen C. Characterization of microRNA expression profiles in normal human tissues. BMC Genomics. 2007; 8:166; Landgraf P, Rusu M, Sheridan R, Sewer A, Iovino N, Aravin A, Pfeffer S, Rice A, Kamphorst A O, Landthaler M, Lin C, Socci N D, Hermida L, et al. A mammalian microRNA expression atlas based on small RNA library sequencing. Cell. 2007; 129; 1401-1414; Lee E G. Baek M, Gusev Y, Brackett D J, Nuovo G J, Schmittgen T D. Systematic evaluation of microRNA processing patterns in tissues, cell lines, and tumors. RNA. 2008; 14:35-42; Liang, Y., Ridzon, D., Wong, L. & Chen, C. Characterization of microRNA expression profiles in normal human tissues. BMC Genomics 8, 166 (2007); Landgraf et al. A mammalian microRNA expression atlas based on small RNA library sequencing.

Cell 129, 1401-1414 (2007); Lee et al. Systematic evaluation of microRNA processing patterns in tissues, cell lines, and tumors. RNA 14, 35-42 (2008); Schratt G. microRNAs at the synapse. Nat. Rev. Neurosci. 2009; 10:842-849).

TABLE 1 miRNA enriched in various human organs and tissues.

| Organ/Tissue/Cell | Organ/tissue-enriched miRNA |
|---|---|
| Heart | 1, 22, 30a-3p, 30c, 30e-3p, 133a, 133b, 197, 208a, 208b, 210, 221, 222, 302a, 302c, 367, 378, 499-5p, 30e* |
| Musculoskeletal | 1, 22, 95, 133a, 133b, 140, 206, 208, 208b, 433 (osteoblasts), 486-5p, 499 |
| Lung | 15b, 18b, 21, 34b, 126, 135b, 138, 142-3p, 142-5p, 146, 146b-5p, 155, 181a, 199b-5p, 200c, 205, 211, 223, 224, 302b, 375, 449a, 449b, 450b-5p, 486-5p, 492, 522, 566, 574-3p, 620, 650, 766, 886-5p. |
| Trachea | 34b, 135b, 146, 146b, 147b, 155, 199b-5p, 200b, 200c, 205, 219-5p, 223, 302b, 375, 449b |
| Liver | 30e-3p, 122a, 130b, 136, 148a, 192, 194, 362-3p, 376c, 455-3p, 483-5p, 505, 518b, 571, 616, 622, 801, 885-5p, 17*, 30d*, 194* |
| Kidney | 10a, 10b, 30a-3p, 30c, 107, 135a, 135b, 138, 184, 187, 190, 192, 194, 196b, 200a, 204, 211, 324-5p, 373, 489, 500, 501-5p, 502-3p, 502-5p, 503, 506, 508-3p, 508-5p, 509-3p, 509-5p, 510, 532-5p, 708, 768-3p, 886-3p, 886-5p, 891a, 10b*, 30a*, 30c-2*, 30e*, 200a*, 200b*, 424*, 500* |
| Bladder | Let-7g, 18, 23b, 26a, 26b, 27b, 28, 106b, 125a, b, 143, 145, 152, 218, 221, 223, 296, 374, 422b, 451 |
| Adipose | 10b, 30, 99a, 139-3p, 139-5p, 154, 193a-5p, 196a, 224, 335, 365, 378/378*, 422b, 432, 452, 494, 518d-3p, 642a-3p, 708, 10b*, 335* |
| Breast | let-7a, 10b, 20ab, 26a, 29a, 30a-3p, 30a-5p, 125b, 126, 145, 146, 195, 196a-2, 199b, 205, 206, 335, 339-5p, 378, 451, 489, 516-5p, 517c, 519c, 520g, 520h, 525, 1246 |
| Ovary | Let-7a, let-7b, let-7c, 10b, 17-3p, 26a, 100, 125a, 125b, 127, 145, 182, 195, 199a-5p, 202, 205, 214, 298, 382, 503, 672, 741, 742, 883-3p, 199a*, 202* |
| Fallopian tubes | 10a, 10b, 31, 34b, 34c, 135a, 135b, 424, 449 |
| Uterus | Let-7c, 10b, 26a, 99a, 100, 125a-5p, 125b, 130a, 140, 143, 145, 195, 196b, 199b, 204, 214, 222, 939, 199* |
| Cervix | Let-7a, let-7c, let-7 g, 10b, 100, 101, 125a-5p, 125b, 130a, 134, 140, 143, 145, 186, 195, f223b, 197, 199a, 199b, 203, 204, 214, 218, 222, 320, 424, 497, 154*, 199a* |
| Prostate | Let-7c, 1, 21, 23b, 24, 27b, 28, 34a, 99a, 100, 125b, 130a, 143, 145, 147b, 183, 187, 188-3p, 199b-5p, 200b, 205, 214, 221, 222, 328, 373, 410, 455-5p, 490-3p |
| Testicle | 15b, 34a, 34b, 34c, 127, 134, 135a, 135b, 187, 202, 204, 370, 371, 372, 373, 376a, 382, 424, 449, 465a-5p, 465b-5p, 506, 508, 509, 510, 514, 517a, 517c, 871-5p, 871-3p, 888, 202*, 888* |
| Vascular system | Let-7 family, 10a, 16, 17-92 cluster (17, 18a, 19a, 19b, 20a, 92), 21, 22, 23a, 23b, 24, 25, 27a, 27b, 29a-c, 30b, 30c, 31, 34a, 93, 98, 100, 106a, b, 125a-5p, 125b, 126, 130a, 133a, 143, 145, 146a, 185, 199a-3p, 210, 221, 222, 320, 345, 361-5p, 365, 382, 409-3p, 431, 484, 495, 503, 532-5p, 939, 27a*, 30a*, 30e*, 93*, 126*, 130b*, 222* |
| Spleen | 15a, 15b, 126, 139, 142-3p, 142-5p, 146, 150, 155, 181a, 181b, 181d, 223, 302b, 342 |
| Thymus | 15a, 15b, 17-5p, 19b, 20b, 25, 93, 106a, 106b, 142-3p, 142-5p, 146, 149, 150, 155, 181a, 181b, 181c, 182, 183, 205, 213, 342 |
| Lymph nodes | Let-7g, 15a, 20b, 21, 106b, 140, 142-3p, 146, 146b, 150, 181b, 181d, 342, 431 |
| Peripheral lymphocytes | Let-7g, 9, 15a, 15b, 17, 19b, 20a, 31, 92a, 106a, 124a, 124b, 128a, 137, 142-3p, 146b-5p, 150, 186, 191, 197, 222, 223, 328, 342-3p, 423, 431, 454, 484, 766, 27*, 223* |
| T-cells | 142-3p, 146a, 155, 181a, 205, 223, 424 |
| B-cells | 142, 150, 342, 523 |
| Thyroid | Let-7i, 1, 7, 135a, 135b, 206, 345, 497 |
| Adrenal gland | Let-7g, 7, 15a, 26b, 27a, 99b, 124, 127, 132, 134, 137, 139, 152, 181a, 187, 192, 195, 202, 299, 302b, 323, 324-3p, 324-5p, 328, 330-3p, 331, 335, 340, 365, 369-3p, 375, 379, 382, 409-5p, 429, 431, 432, 455-5p, 483-5p, 514, 126*, 182*, 202* |
| Pancreas | 7, 18a, 21, 29a, 30a-5p, 34a, 103, 127-3p, 129-3p, 130b, 134, 135a, 135b, 136, 141, 148a, 182, 183, 184, 192, 193a-3p, 193a-5p, 195, 199a-3p, 199a-5p, 200b, 200c, 204, 216a, 216b, 217, 224, 335, 340, 365, 367, 374a, 374b, 375, 376a, 376c, 379, 382, 383, 429, 432, 451, 455-5p, 485-5p, 487b, 494, 497, 539, 543, 642, 758, 939, 130b*, 136*, 183*, 200b*, 493* |
| Pancreatic β-cells | 7, 9, 21, 127-3p, 130b, 184, 195, 216a, 216b, 217, 335, 376a, 376c, 497, 939, 493* |
| Large intestine (Colon) | 18, 19, 31, 141, 143, 145, 147b, 192, 194, 200a, 200b, 200bN, 200c, 200cN, 214, 215, 219-2-3p, 321, 338, 375, 378, 422a, 429, 450b-5p, 487a, 490-3p, 492, 504, 565, 574-3p, 622, 650, 801, 143*, 200b* |
| Small intestine | 31, 141, 143, 192, 194, 200a, 200b, 200bN, 200c, 200cN, 215, 321, 375, 429 |
| Esophagus | 31, 106a, 106b, 140, 143, 145, 148a, 203, 205, 210, 211, 214, 221 |
| Stomach | 7, 26a, 26b, 29c, 31, 106a, 106b, 124b, 130b, 141, 145, 148a, 182, 188, 192, 197, 200a, b, c, 203, 375, 650 |

TABLE 1-continued miRNA enriched in various human organs and tissues.

| Organ/Tissue/Cell | Organ/tissue-enriched miRNA |
|---|---|
| Brain | Let-7a, c, e, 7, 9, 19a, b, 92b, 96, 98, 99a, b 103, 105, 106a, 107, 124a, 125a, 125b, 126, 127, 128a, 129, 132, 134, 135a, 137, 138, 139, 149, 151, 153, 154, 181a, 181b, 181c, 182, 183, 184, 190, 195, 197, 204, 211, 212, 213, 218, 219(-3p)(-5p), 221, 222, 299-3p, 299-5p, 300, 323-3p, 324-5p, 326, 328, 329, 330, 331, 335, 337, 338-5p, 340, 342, 346, 361, 363, 369-3p, 369-5p, 370, 377, 379, 380, 381, 382, 383, 409-3p, 410, 411, 423-5p, 425, 432, 433-5p, 453, 485-3p, 485-5p, 487a, b, 488, 491-5p, 494, 495, 496, 497, 504, 522, 539, 541, 543, 544, 551b, 572, 577, 584, 592, 598, 625, 628, 652, 654, 655, 656, 668, 671, 672, 708, 744, 758, 769-3p, -5p, 770, 873, 874, 876-3p, 885-3p, -5p, 889, 935, 939, 941, 1193, 1197, 1224-3p, -5p, 1225-3p, 1237, let-7d*, 7*, 9*, 99b*, 125b-2*, 129*, 138-2*, 340*, 380*, 411*, 425*, 488*, 744* |
| Brain, enriched in synapses, axons, dendrites, spines | Let-7e, 7, 9, 98, 99a, 100, 124a, 125a, 125b, 128a, 129, 132, 134, 135a, 137, 138, 154, 181a, c, 182, 183, 204, 212, 213, 218, 323-3p, 329, 337, 342-3p, 369-3p, 369-5p, 370, 381, 382, 409-3p, 425, 433-5p, 483-3p, 485-5p, 487b, 491-5p, 494, 495, 496, 541, 543, 656, 668, 874, 889, 935, 939, 9*, 181a-1* |
| Cortex | 9, 29a (not brain-enriched), 98, 100, 103, 107, 124a, 125a, 125b, 126, 128a, 129, 132, 134, 137, 138, 149, 154, 181a, b, c, d, 183, 197, 212, 213, 222, 323, 330-3p, 338-3p, -5p, 342, 370, 381, 382, 411, 425, 433, 491-5p, 539, 885 |
| Hippocampus | 9, 29a (not brain-enriched), 96, 99a, 103, 107, 124a, 125b, 126, 128a, 132, 134, 137, 138, 153, 181a, 181b, c, 184, 197, 212, 218, 219, 221, 222, 324-5p, 328, 330, 331, 335-5p, 338, 369-3p, 379, 381, 382, 383, 411, 425, 433-5p, 485-5p, 488, 491-5p, 574, 874, 885 |
| Hypothalamus | Let-7a, b, c, 103, 124a, 125a, 128a, 132, 136, 138, 212, 338, 451 |
| Cerebellum | Let-7e, 9, 98, 103, 124a, 125b, 128, 132, 134, 137, 138, 181a, 181b, 181c, 204, 206, 212, 213, 218, 338, 381, 382, 425, 432, 489, 592, 874, 885 |
| Amygdala | 103, 134, 138, 182, 183, 222, 323-3p, 369, 381, 382, |
| Spinal cord | 218, 219, 338, 451, 486 |
| Pituitary gland | Let-7c, 7, 9, 22 (not brain-enriched), 23b (not brain-enriched), 24 (not brain-enriched), 26a, b (not brain-enriched), 27b (not brain-enriched), 29a, b, c (not brain-enriched), 30b, d (not brain-enriched), 92a, b, 96, 99a, b, 103, 107, 125a, b, 126(not brain-enriched), 127, 128, 132, 134, 135a, 136 (not brain-enriched), 141 (not brain-enriched), 148a (not brain-enriched), 154, 181a-c, 182, 183, 184, 195, 197, 199b (not brain-enriched), 200a, b, c, 204, 212, 213, 218, 322, 323, 324, 328, 329, 335, 339 (not brain-enriched), 361, (not brain-enriched), 369, 370, 375, 377, 379, 381, 410, 411, 424 (not brain-enriched), 429 (not brain-enriched), 432, 433, 451 (not brain-enriched), 487b, 491, 494, 508, 514, 539, 542, 574 (not brain-enriched), 603, 618, 628, 652, 660 (not brain-enriched), 663, 665, 885, 890 |
| Midbrain, Substantia nigra | Let-7a, b, c, d, e, 9, 29a (not brain-enriched), 98, 99a, b, 100, 107, 125a, b, 126, 127-3p, 129-3p, 134, 138, 149, 181a, 197, 204, 323, 329, 338, 340, 340*, 379, 383, 410, 424, 425, 432, 433, 487a, b, 539, 744, 760, 9*, 99b*, 129*; 133b |
| Medulla oblongata | 10a, b, 34a, 451 (all not brain-enriched), 219, 338 |
| Temporal lobe (hippocampus) | 129, 204, 218, 219-5p, 338-3p, 487a |
| Motor neuron | 9, 133b, 431, |
| Sympathetic neurons | Let-7c-a, 16, 23a, 25, 125b-1, 138-2, 185, 221, 433, 541 |

The term "not brain-enriched" refers to miRNA enriched in one or two brain areas only.

miRNAs play important roles in the regulation of target genes by binding to complementary regions of messenger transcripts and repressing their translation or by regulating degradation [Griffiths-Jones S, et al. miRBase: microRNA sequences, targets and gene nomenclature. Nucleic Acids Res. 2006; 34, Database issue: D140-D144; Bartel D P. MicroRNAs: target recognition and regulatory functions. Cell. 2009; 136:215-233]. Many miRNAs are specific to, or are over-expressed in brain, different brain areas (such as hippocampus, midbrain, frontal cortex, pituitary gland), and different cell types, such as neurons and glial cells (Sempere et al. Genome Biol. 2004; Deo et al. Dev. Din. 2006; Bak et al. RNA. 2008; Trivedi and Ramakrishna Int. J. Neurosci. 2009; Weng et al. Biomed. Res. 2011; He et al. Neuron. 2012; Ziats M N and Rennert O M. Mol Psychiatry. 2014; Hamilton D E et al. Physiol. Genomics. 2014). Some miRNAs, including those that are cell-specific, are enriched in certain cellular compartments, particularly in axons, dendrites and synapses (see, e.g., Schratt et al. A brain-specific microRNA regulates dendritic spine development. Nature. 2006; 439:283-289; Lugli et al. Expression of microRNAs and their precursors in synaptic fractions of adult mouse forebrain. J. Neurochem. 2008; 106:650-661; Schratt G. microRNAs at the synapse. Nat Rev Neurosci. 2009; 10(12): 842-849; Smalheiser and Lugli. Neuromolecular Med. 2009; Rajasethupathy. Neuron. 2009; Kye M J et al. Somatodendritic microRNAs identified by laser capture and multiplex RT-PCR. RNA 13, 1224-1234 (2007); Yu et al. Exp Cell Res. 2008; Cougot et al. Dendrites of Mammalian Neurons Contain Specialized P-Body-Like Structures That Respond to Neuronal Activation. J. Neuroscie. 28, 13793-13804 (2008); Kawahara. Brain Nerve. 2008; Schratt G. microR-NAs at the synapse. Nat. Rev. Neurosci. 10, 842-849 (2009); Pichardo-Casas et al. Brain Research. 2012). Many of the 2000 miRNAs that have been discovered in human cells to date are specific to or are overexpressed in certain organs/tissues/cells [20-23]. Intracellular concentrations and rates of secretion of miRNAs can be dramatically affected by physiological and pathological cellular processes [29-31].

miRNAs appear in extracellular space and subsequently in bodily fluids (e.g. plasma, serum, urine, saliva, and milk) via not fully understood mechanisms, such as active secretion in the form of exosomes and miRNA complexes with proteins (AGO2, NPM1 and others) and high density lipoproteins (HDL), blebbing of apoptotic bodies, budding and shedding of microvesicles, etc. (Turchinovich et al. Characterization of extracellular circulating microRNA. Nucleic Acids Res. 2011; 39:7223-7233; Vickers et al. MicroRNAs are transported in plasma and delivered to recipient cells by high-density lipoproteins. Nat Cell Biol. 2011; 13:423-433; Hoy A M, Buck A H. Extracellular small RNAs: what, where, why? Biochem Soc Trans. 2012; 40:886-890; Pigati L. et al. Selective release of microRNA species from normal and malignant mammary epithelial cells. PLoS One. 2010; 5:e13515; Bellingham S A, Coleman B M, Hill A F. Small RNA deep sequencing reveals a distinct miRNA signature released in exosomes from prion-infected neuronal cells. Nucleic Acids Res. 2012; 40:10937-10949. Due to protection against RNase activity these forms of cell-free miRNA are relatively stable in the bloodstream and other bodily fluids. It has also been shown that many circulating miRNAs do not come from cells of a bodily fluid under investigation, e.g. blood, or other cells in contact with the bodily fluid (Weber et al. Clin. Chem, 2010; Duttagupta et al. PLoS ONE, 2011), which means that they originated from various cells throughout the body. Intracellular concentrations and rates of secretion of miRNAs can be dramatically affected by physiological and pathological cellular processes (Bellingham S A, Coleman B M, Hill A F. Small RNA deep sequencing reveals a distinct miRNA signature released in exosomes from prion-infected neuronal cells. Nucleic Acids Res. 2012; 40:10937-10949; Palma et al. MicroRNAs are exported from malignant cells in customized particles. Nucleic Acids Res. 2012; 40:9125-9138; Pigati L. et al. Selective release of microRNA species from normal and malignant mammary epithelial cells. PLoS One. 2010; 5:e13515). It is also demonstrated in numerous systems that cell-free miRNAs originated from one cell type can be acquired by other cells, changing expression of proteins due to specific inhibition of mRNA targets (van der Vos et al. Neuro-Oncology, 2015; Melo et al. Cancer Cell, 2014).

Numerous data indicate that in cell culture any cell type produce extracellular miRNAs in the form of exosomes, other microvesicles, complexes with proteins and lipids. At least, in vitro secretion of miRNA is selective (Jovicic and Gitler, PLoS ONE, 2017) and there were several attempts to find the nature of this selectivity (Kosaka et al. J. Biol. Chem. 2013; Cha et al. eLIFE, 2015; lavello et al. Int. J. Mol. Med. 2016). Based on these data or a priori some authors suppose that any cell of a live organism can secrete miRNAs (Witwer Clin. Chem. 2015). However, a comparison of concentrations of individual miRNAs in plasma with their abundance in various tissue indicates that not all cells in the human body continuously secrete miRNAs. It is more likely that only some cells periodically secrete certain miRNAs, and such secretion is significantly affected by pathology. For example, in our studies control plasma concentration of miR-206, which is highly enriched in muscles and heart, was significantly lower than many brain-enriched miRNAs, but increased in subjects with amyotrophic lateral sclerosis about 8 times (see Int. Pat. Appl. No. PCT/US2017/023470). Keeping in mind that circulating miRNAs can affect metabolic processes in numerous cells/organ/tissues capable to acquire exosomes and other cell-free complexes of miRNAs, selective limited secretion is likely, otherwise circulating miRNAs could lead to dramatic disorganization of metabolism in an organism as a whole. The ability to secrete miRNAs in vivo has been demonstrated for stem cells, tumor cells (maybe, due to their origin from stem cells), some endothelial and blood cells (Eirin et al. Gene, 2014; Baglio et al. Stem Cell Res. Ther., 2015). Paracrine effects of these miRNAs have been also demonstrated (Chowdhury et al. Oncotarget, 2014; van der Vos et al. Neuro-Oncology, 2015; Shah et al. Cancer Biol. Therapy, 2015; Kohlhapp et al. Oncogene, 2015). Numerous data devoted to searching biomarkers of different diseases indirectly indicate that various pathologies induce the ability of affected cells to secrete/excrete miRNAs (Castoldi et al. Sci. Rep. 2016; Sheinerman and Umansky, Front. Cell. Neurosci. 2013; Sheinerman and Umansky, Exp. Rev. Mol. Diagn. 2015). In some situations, such as tumor growth, the amount of secreted miRNAs significantly increases, which can lead to more distant effects, e.g. metastatic processes.

The existing data indicate that various miRNAs are enriched in different fractions of plasma/serum (Arroyo et al. PNAS, 2011; Ji H. et al. PLoS ONE, 2014; Jovicic and Gitler, PLoS ONE, 2017; Ji H. et al. PLoS ONE, 2014). There are several publications devoted to fractionation of miRNAs circulating in plasma and serum (Coenen-Stass et al. Human Mol. Gen., 2016), which demonstrate that exosomes and other microvesicles contain only 10%-15% of all cell-free miRNAs in the bloodstream. In addition, it was found that the amount of individual miRNAs is less than 1 copy per exosome (Chevillet et al. PNAS 2014). The most of circulating miRNAs are found in smaller complexes of miRNAs with proteins and lipids/lipoproteins (Turchinovich et al. Nucl. Acid Res., 2011; Arroyo et al. PNAS, 2011). Studies demonstrate that exosomes can be absorbed by various cell types and their miRNAs affect functioning of respective targets (Rana et al. Neoplasia, 2013; Challagundla et al. JNCI, 2015; Guay et al. Cell Communication and Signalling, 2015. Most likely circulating complexes of miRNA with proteins and lipids/lipoproteins also are capable of changing metabolic processes in targeted cells (Vickers et al. MicroRNAs are transported in plasma and delivered to recipient cells by high-density lipoproteins. Nat Cell Biol. 2011; 13:423-433).

Each miRNA can potentially affect many mRNA targets. There are several programs for in silico analysis of complementarity between miRNA and mRNA; the lists of possible targets for a miRNA frequently include hundreds of genes. Hence, based on sequence analysis alone, a given miRNA can potentially be involved in numerous different pathologies. Same miRNA can function as a tumor suppressor in one cell type and as oncogene in other cells depending on spectrums of mRNA targets. Also one mRNA can be regulated by numerous miRNAs. Experimental data on miRNA roles in epigenetic regulation of numerous cellular processes are rapidly accumulating (McNeill and Van Vactor, 2012; Siegel et al., 2011). Detailed analysis of available data indicates that significant inhibition of individual miRNA functioning most likely should be caused by several miRNAs (Turchinovich et al. Extracellular miRNA: A Collision of Two Paradigms. Trends Biochem Sci. 2016; 41:883-892).

Thus, circulating miRNAs are good candidates for regulating metabolic processes in distant cells.

An assessment was undertaken as to whether aging-associated processes in various brain regions can be detected in vitro via quantitative analysis of circulating brain-enriched miRNAs detectable in the bloodstream. Also, an evaluation of age- and sex-dependence of plasma concentrations of miRNAs enriched in different brain regions was undertaken.

miRNAs appear in extracellular space and in bodily fluids due to a variety of mechanisms that remain not fully understood; these mechanisms include secretion, excretion, and blebbing [36-38]. Our studies that have been performed to date suggested that various processes, such as cell dysfunction and neurite/synapse loss, can lead to changes in miRNA concentrations in plasma, representing a rich source of potential biomarkers that detect pathology in the corresponding organ [Sheinerman K S, et al. Plasma microRNA biomarkers for detection of mild cognitive impairment. Aging (Albany N.Y.). 4, 590-605 (2012); Sheinerman K S, et al. Plasma microRNA biomarkers for detection of mild cognitive impairment: biomarker validation study. Aging (Albany N.Y.). 5, 925-938 (2013); Sheinerman K S, Umansky S R. Circulating cell-free microRNA as biomarkers for screening, diagnosis and monitoring of neurodegenerative diseases and other neurologic pathologies. Front Cell Neurosci. 7, 150 (2013); Sheinerman K S, Umansky S R. Universal Screening Test based on analysis of circulating organ-enriched microRNAs: a novel approach to diagnostic screening. Expert Rev. Mol. Diagn. 15, 329-338 (2015).]. In addition, many publications have demonstrated that miRNA secretion, circulation in bodily fluids, and uptake by other cells are relatively common mechanisms of cell-to-cell communication, particularly in carcinogenesis, metastasis formation and other processes [Guay C, et al. Horizontal transfer of exosomal microRNAs transduce apoptotic signals between pancreatic beta-cells. Cell Commun Signal. 13:17 (2015); Pigati L, et al. Selective release of microRNA species from normal and malignant mammary epithelial cells. PLoS One. 5, e13515 (2010); Hoy A M, Buck A H. Extracellular small RNAs: what, where, why? Biochem Soc Trans. 40, 886-890 (2012); Kosaka N, et al. Trash or Treasure: extracellular microRNAs and cell-to-cell communication. Front Genet. 4, 173 (2013); Singh R, et al. Exosome-mediated transfer of miR-10b promotes cell invasion in breast cancer. Mol Cancer. 13, 256 (2014); Silvaa M and Melo S A. Non-coding RNAs in Exosomes: New Players in Cancer Biology. Current Genomics. 16, 295-303 (2015). Zhang Y, et al. Hypothalamic stem cells control ageing speed partly through exosomal miRNAs. Nature. 2017 Jul. 26. [Epub ahead of print]]. Recently, it was also demonstrated that stem cells of the hypothalamus secrete miRNAs that are transported to the CSF and potentially reach the bloodstream [Zhang Y, et al. Hypothalamic stem cells control ageing speed partly through exosomal miRNAs. Nature. 2017 Jul. 26. [Epub ahead of print]]. These miRNAs play an important role in aging-related processes. In this study, the present inventors pursue a targeted approach based on quantitative RT-PCR (qRT-PCR) analysis of a relatively small number of pre-selected miRNAs that are (1) enriched in different brain regions and (2) present at detectable levels in plasma. In addition, the present inventors used an miRNA-pair approach [Sheinerman K S, et al. Plasma microRNA biomarkers for detection of mild cognitive impairment. Aging (Albany N.Y.). 4, 590-605 (2012); Sheinerman K S, et al. Plasma microRNA biomarkers for detection of mild cognitive impairment: biomarker validation study. Aging (Albany N.Y.). 5, 925-938 (2013); Sheinerman K S, Umansky S R. Circulating cell-free microRNA as biomarkers for screening, diagnosis and monitoring of neurodegenerative diseases and other neurologic pathologies. Front Cell Neurosci. 7, 150 (2013)]. The concentration ratios of all miRNA pairs from the same sample were calculated, and the most promising pairs for effective differentiation of two populations or correlation with the parameter of interest, e.g. age, were selected for further testing and validation. This approach has proven to be particularly effective in the analysis of plasma concentrations of brain-enriched miRNAs to compensate not only for technical variability but also for physiological variability, e.g. changes in blood supply or blood-brain barrier permeability. Subject-to-subject variability is further decreased if a miRNA biomarker pair is comprised of two miRNAs, the plasma concentrations of which are highly correlated [Sheinerman K S, et al. Plasma microRNA biomarkers for detection of mild cognitive impairment. Aging (Albany N.Y.). 4, 590-605 (2012); Sheinerman K S, Tsivinsky V G, Umansky S R. Methods of using miRNA from bodily fluids for early detection and monitoring of Mild Cognitive Impairment (MCI) and Alzheimer's Disease (AD). U.S. Pat. No. 9,556,487B2].

The present invention is based on the inventors' idea that the pituitary gland (PG) in addition to other hormones secretes miRNAs, which affect cells in various brain areas, appear in the bloodstream and perform fine-tuning of metabolic processes in cells throughout the body. Aging and manifestation of various age-related diseases may be caused at least in part by aging-associated changes in spectrum of these miRNAs ("miRNA hormones"). The inventors investigated potential use of cell-free miRNAs circulating in the bloodstream for early detection of AD. Since early stages of AD are characterized by dysfunction and destruction of synapses leading to neuronal death in hippocampus, the inventors hypothesized that this process should cause additional release of miRNAs enriched in neurites and synapses of the affected brain area. To compensate for disease unrelated processes (technical problems, such as isolation of plasma miRNAs or presence of PCR inhibitors, and biological issues, e.g. changes in blood supply and/or blood-brain barrier permeability) the present inventors also included in the study miRNAs enriched in brain areas, which are not affected by AD and several ubiquitous miRNAs. Two families of miRNAs capable of detecting MCI with 87%-96% accuracy were found. Since not all but about 50% of MCI patients progress to AD dementia, the present inventors also looked for biomarkers capable of specific detection of those patients. Four such miRNAs were found: miR-7, miR-125b, miR-16 and miR-451. Interestingly, all four miRNAs, being inhibitors of anti-apoptotic proteins Bcl-2 or Bcl-x, possess pro-apoptotic activity and the concentrations of these miRNAs in plasma is highly correlated, despite miR-7 and miR-125b being brain-enriched and miR-16 and miR-451 being ubiquitous miRNAs (U.S. Pat. No. 9,556,487, U.S. Patent Application Publication No. 2014/0256562 A1). Another common property that the present inventors found as common for these four miRNAs was that they are all highly expressed in pituitary gland. The inventors therefore hypothesized that miRNA secreted from the pituitary gland can stimulate MCI progression to AD dementia. Analysis of potential targets of these and other PG-enriched miRNAs supported this possibility since many apoptosis related genes are among their predicted targets (http://mirtarbase.mbc.nctu.edu.tw/). Besides, for some of them involvement in regulation of apoptosis was experimentally proved. In addition, among the potential targets of these miRNAs are genes involved in various pathways associated with age-related diseases, such as insulin, TOR, and Wnt signaling, autophagy and other pathways. It should be mentioned that these and many other PG-enriched miRNAs are also enriched in the adrenal gland. However, chances of adrenal miRNAs to reach hippocampus are much smaller due to the existence of the blood-brain barrier. Of course, it is possible that adrenal gland also secretes these miRNAs regulating extra-brain processes. Many miRNAs, the abnormally high concentrations of which in plasma predict MCI progression to AD dementia, serve as tumor suppressors for cancer of various organs. At least partially this can explain inverse comorbidity of cancer and AD. These properties of miRNAs secreted by pituitary gland also explain another phenomenon, higher predisposition to AD and lower risk of cancer for people with Down syndrome, since four of five miRNAs encoded by chromosome 21 are expressed in the pituitary gland. Another fact implicating PG as a source of such regulation is a well-known anti-aging effect and extension of the lifespan caused by hypophysectomy in adult animals. In addition, it was previously demonstrated that dwarf mice have longer lifespan and the df/df/APP/PS1 hybrid mice have reduced Aβ plaque deposition and Aβ 1-40 and Aβ 1-42 concentrations (Puig K L et al. The Ames dwarf mutation attenuates Alzheimer's disease phenotype of APP/PS1 mice. Neurobiol Aging. 2016; 40:22-40). Notably, age effect on plasma concentrations of PG-enriched miRNAs (e.g., miR-127-5p, miR-154, miR-369, miR-381, miR-410, and miR-411) is 10-20 times lower in dwarf mice compared to normal controls (Victoria et al. Circulating microRNA signature of genotype-by-age interactions in the long-lived Ames dwarf mouse. Aging Cell. 2015; 14:1055-1066). There are other observations supporting the above hypothesis: (i) androgen deprivation therapy in the treatment of prostate cancer is associated with increased risk of dementia (Nead K T et al. Influence of age on androgen deprivation therapy-associated Alzheimer's disease. Sci Rep. 2016; 6:35695); (ii) women with a surgical premature menopause have an increased risk of MCI and AD (Davey D. A. Alzheimer's disease, dementia, mild cognitive impairment and the menopause: a 'window of opportunity'? Womens Health (Lond). 2013; 9:279-290); (iii) injection of pituitary gland extract for growth hormone treatment led to Aβ deposit (Jaunmuktane et al. Evidence for human transmission of amyloid-β pathology and cerebral amyloid angiopathy. Nature. 2015; 525:247-250; Jucker M. and Walker L. C. Neurodegeneration: Amyloid-β pathology induced in humans. Nature. 2015; 525:193-194); (iv) attenuation of PG response to Gonadotropin-Releasing Hormone during aging (Shaw et al. J. Clin. Endocrinol. Metab. 2009).

As disclosed herein, the spectrum of miRNA hormones secreted by PG is changed during aging. Most likely, this phenomenon is similar to changes in secretion of other PG hormones due to decrease in concentrations of sex hormones by the end of evolutionary time-limited reproductive period, which is important to prevent reproduction of mutations accumulated in germ cells. Importantly, females in other mammalian species, including non-human primates, do not possess the menopause characteristic of a woman in mid-life (Alberts et al. PNAS, 2013). In addition, aged monkeys and apes (as well as dogs) can accumulate large quantities of Aβ but remain without a dementia-like disorder (Walker and Jucker, The Exceptional Vulnerability of Humans to Alzheimer's Disease. Trends Mol Med. 2017; 23:534-545).

Definitions

As used herein, the terms "biological age" and "physiological age" refer to the physiological state of an animal or tissue relative to the physiological changes that occur throughout the animal's lifespan. The biological age may be represented as a particular number of days, months, and/or years. The term "chronological age" refers to the age of an animal as measured by a time scale such as month or years. Biological age can be higher or lower than the chronological age of the animal, since aging is not only limited to time, but is, in fact, a complex process with multiple causes. Biological age can be modulated by internal as well as external factors: e.g., genetics, diet, environment, mental health, etc.

As used herein the terms "aging", "general a in symptoms", "general aging processes", "aging associated symptoms", "aging status", "aging associated processes", "aging related symptoms", and "aging related processes" refer to various changes on molecular, cellular, organ, tissue and/or organism level which correlate with aging. Some non-limiting examples of such processes/symptoms include, e.g.:
1. Molecular level—shortening of telomeres, accumulation of DNA mutations, abnormal proteins and other molecules, additional DNA methylation and other epigenetic changes (see, e.g., Burkle et al. MARK-AGE biomarkers of ageing. Mech Ageing Dev. 2015; 151:2-12.).
2. Cellular level—decrease of the number of potential divisions of somatic cells (Hayflick limit), stem cell exhaustion, neuronal death, chromosomal abnormalities, genome instability (see, e.g., Lopez-Otin et al. The Hall marks of Aging. Cell (2013) 153:1194-1217).
3. Organ/tissue level—changes in levels of secreted sex and other hormones, atherosclerosis, muscle strength, skin changes.
4. Organism level—gait speed, memory decrease, higher blood pressure (see, e.g., Sebastiani et al. Biomarker signatures of aging. Aging Cell (2017) pp. 1-10).

For additional non-limiting examples see, e.g., Burkle et al. MARK-AGE biomarkers of ageing. Mech Ageing Dev. 2015; 151:2-12.

As used herein, the term "organ-enriched" means that miRNA concentration in a given organ is at least 4-5 times higher than in other organs. For example, "brain-enriched" means that miRNA concentration in brain is at least 4-5 times higher than in other organs.

As used herein in connection with miRNA enrichment in a certain area of the brain, the term "enriched" means that miRNA concentration in said area of the brain is higher (preferably, at least 2-fold higher, more preferably at least 5-fold higher, most preferably at least 10-fold higher) than in brain in general. The term refers to the difference in concentrations within the brain areas (e.g., as measured using qRT-PCR).

Within the meaning of the present invention, the term "synapse and/or neurite miRNA" refers to miRNA which (i) is "brain-enriched" and (ii) is present in a synapse and/or neurite (i.e., axon and/or dendrite and/or spine). To be useful in the methods of the present invention, synapse and/or neurite miRNAs should be detectable in bodily fluids as a result of their release from neurons (e.g., due to secretion, neurite/synapse destruction or neuronal death).

The term "neurite" as used herein refers to any projection from the cell body of a neuron. This projection can be an axon, a dendrite, or a spine.

The term "axon" refers to a long, slender projection of a neuron that conducts electrical impulses away from the neuron's cell body or soma. Axons are distinguished from dendrites by several features, including shape (dendrites often taper while axons usually maintain a constant radius), length (dendrites are restricted to a small region around the cell body while axons can be much longer), and function (dendrites usually receive signals while axons usually transmit them). Axons and dendrites make contact with other cells (usually other neurons but sometimes muscle or gland cells) at junctions called synapses.

The term "dendrite" refers to a branched projection of a neuron that acts to conduct the electrochemical stimulation received from other neural cells to the cell body of the neuron from which the dendrites project.

The term "synapse" refers to specialized junctions, through which neurons signal to each other and to non-neuronal cells such as those in muscles or glands. A typical neuron gives rise to several thousand synapses. Most synapses connect axons to dendrites, but there are also other types of connections, including axon-to-cell-body, axon-to-axon, and dendrite-to-dendrite. In the brain, each neuron forms synapses with many others, and, likewise, each receives synaptic inputs from many others. As a result, the output of a neuron may depend on the input of many others, each of which may have a different degree of influence, depending on the strength of its synapse with that neuron. There are two major types of synapses, chemical synapses and electrical synapses. In electrical synapses, cells approach within about 3.5 nm of each other, rather than the 20 to 40 nm distance that separates cells at chemical synapses. In chemical synapses, the postsynaptic potential is caused by the opening of ion channels by chemical transmitters, while in electrical synapses it is caused by direct electrical coupling between both neurons. Electrical synapses are therefore faster than chemical synapses.

The term "associated with" is used to encompass any correlation, co-occurrence and any cause-and-effect relationship.

The terms "microRNA" or "miRNA" as used herein refer to a class of small approximately 22 nt long non-coding RNA molecules. They play important roles in the regulation of target genes by binding to complementary regions of messenger transcripts (mRNA) to repress their translation or regulate degradation (Griffiths-Jones Nucleic Acids Research, 2006, 34, Database issue: D140-D144). Frequently, one miRNA can target multiple mRNAs and one mRNA can be regulated by multiple miRNAs targeting different regions of the 3' UTR. Once bound to an mRNA, miRNA can modulate gene expression and protein production by affecting, e.g., mRNA translation and stability (Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research, 102, 3-9; He et al., 2004, Nat. Rev. Genet., 5, 522-531; and Ying et al., 2004, Gene, 342, 25-28). Unless otherwise noted, the name of a specific miRNA refers to a mature miRNA sequence. Under current nomenclature rules, human miRNAs are preceded with the prefix "hsa-" (i.e., an abbreviation for *Homo sapiens*). Throughout the specification and figures the hsa- prefix may be dropped for purposes of abbreviation, thus, for example, "hsa-miR-155" and "miR-155" would represent the same RNA sequence.

Information on most currently known miRNAs can be found in the miRNA database miRBase (available at the world wide web at mirbase.org). See also Burside et al., BMC Genomics 9:185 (2008); Williams et al., BMC Genomics 8:172 (2007); Landgraf et al., Cell 129:1401 (2007).

The term "miRNA array" refers to a multiplex technology used in molecular biology and in medicine. It consists of an arrayed series of multiple (e.g., thousands) microscopic spots of oligonucleotides, each containing a specific sequence (probe) complementary to a particular target miRNA. After probe-target hybridization under high-stringency conditions the resulting hybrids are usually detected and quantified by quantifying fluorophore-, silver-, or chemiluminescence-labeled targets to determine relative abundance of miRNA. In the methods of the present invention, both custom-made and commercially available miRNA arrays can be used. Examples of useful commercially available miRNA arrays (based on various methods of target labeling, hybrid detection and analysis) include arrays produced by Agilent, Illumina, Invitrogen, Febit, and LC Sciences.

The term "next generation sequencing technologies" broadly refers to sequencing methods which generate multiple sequencing reactions in parallel. This allows vastly increased throughput and yield of data. Non-limiting examples of commonly used next generation sequencing platforms include Helicos small RNA sequencing, miRNA BeadArray (Illumina), Roche 454 (FLX-Titanium), and ABI SOLiD.

An "individual" or "subject" or "animal", as used herein, refers to humans, veterinary animals (e.g., cats, dogs, cows, horses, sheep, pigs, etc.) and experimental animal models of diseases. In a preferred embodiment, the subject is a human.

The term "purified" as used herein refers to material that has been isolated under conditions that reduce or eliminate the presence of unrelated materials, i.e., contaminants, including native materials from which the material is obtained. For example, RNA purification includes elimination of proteins, lipids, salts and other unrelated compounds present in bodily fluids. Besides, for some methods of analysis a purified miRNA is preferably substantially free of other RNA oligonucleotides contained in bodily fluid samples (e.g., rRNA and mRNA fragments, ubiquitous miRNAs, which are expressed at high levels in almost all tissues [e.g., miR-16], etc.). As used herein, the term "substantially free" is used operationally, in the context of analytical testing of the material. Preferably, purified material substantially free of contaminants is at least 50% pure; more preferably, at least 90% pure, and still more preferably at least 99% pure. Purity can be evaluated by chromatography, gel electrophoresis, composition analysis, biological assay, and other methods known in the art.

As used herein, the term "similarly processed" refers to samples (e.g., bodily fluid samples or purified miRNAs) which have been obtained using the same protocol.

In the context of the present invention insofar as it relates to any of the disease conditions recited herein, the terms "treat", "treatment", and the like mean to relieve or alleviate at least one symptom associated with such condition, or to slow or reverse the progression of such condition, or to arrest, delay the onset (i.e., the period prior to clinical manifestation of a disease) and/or reduce the risk of developing or worsening a disease.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989")]; DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

Methods for Identification of Diagnostic miRNA Pairs

To identify the most promising biomarker pairs, the present inventors used the following approach: selection of a numerator and a denominator for each pair from those circulating miRNAs, which significantly correlate (Spearman's rank correlation coefficient $\rho > 0.8$) in a respective bodily fluid of different individuals, and whose plasma concentration is differently affected by aging. Concentrations of miRNAs in plasma depend on numerous factors, including (i) levels of miRNA expression in various organs and tissues; (ii) levels of miRNA secretion from different cell types; (iii) stability of miRNAs in extracellular space and their appearance in plasma in different forms, such as exosomes and other microvesicles, complexes with proteins, lipids and, possibly, other molecules; (iv) blood supply and blood-brain barrier permeability for brain-enriched miRNAs; and (v) other factors. A pathological process may affect some or all of these factors. The present inventors suggest that a nominator and a denominator of an effective biomarker miRNA pair should share some of these basic common factors (e.g., both are brain-enriched and secreted in exosomes) and would change differently in response to aging. This does not mean that any correlated miRNA will form a good biomarker pair, since if they are similarly changed by aging their ratio will mask those changes.

The present invention provides a method of "promising" miRNA pair selection, which method comprises the following steps:
1. Concentrations of miRNAs pre-selected on the basis of their enrichment in an organ of interest (e.g., brain) are measured in a bodily fluid (e.g., plasma, serum, cerebrospinal fluid (CSF), saliva, urine) of at least two comparative cohorts (e.g., a disease and control for a diagnostic test, two diseases for a test capable of differentiating two pathologies, a disease at different stages of pathologic process development, or a disease before and after treatment for monitoring tests).
2. Means of each miRNA concentrations are calculated for comparative cohorts.
3. The difference between the means for each miRNA from two comparative cohorts is calculated and miRNAs are divided in two groups: (i) with high difference values; and (ii) with low or with opposite sign difference values.
4. miRNAs from different groups are combined as potential biomarker pairs if parameters determined in step 3 differ at least 1.5 times. One miRNA is used as a numerator and another miRNA is used as a denominator in a potential "promising" miRNA pair.
5. To further reduce an impact of individual variations of each particular miRNA concentration in plasma or other bodily fluid, miRNA with high positive correlation (Spearman's rank correlation coefficient $\rho$ calculated for all samples in compared groups is $\geq 0.8$) are selected as a numerator and a denominator for the biomarker pair. This step significantly decreases the number of potential biomarker miRNA pairs, reduces variance of selected biomarkers caused by factors unrelated to processes differentiating two comparative cohorts and significantly increases test sensitivity and specificity.

The order of steps 3-4 and step 5 can be switched as follows:

After step 1, calculate Spearman's rank correlation coefficient (r) for all possible pairs of individual miRNA measured in step 1 in all bodily fluid samples. Then select as potential biomarker pairs of miRNA with a high positive correlation ($\rho \geq 0.8$), compare a ratio of miRNA concentrations in two subject cohorts for each selected miRNA pair and determine a miRNA pair as a suitable biomarker if this pair differentiates two subject cohorts with a statistically significant P-value.

Selection of miRNAs for biomarker pairs is an important step in developing screening, diagnostic and monitoring tests based on analysis of cell-free circulating miRNAs in bodily fluids. The present invention addresses this issue by providing the following methods for selection of effective biomarker pairs.

In one embodiment, the invention provides a method for selecting a biomarker miRNA pair for diagnosis and/or monitoring of aging, said method comprising the following steps:
(a) selecting at least four miRNAs known to be enriched in an organ or tissue affected by aging;
(b) measuring the level of each miRNA selected in step (a) in bodily fluid samples from two subject cohorts;
(c) calculating the mean level of each miRNA measured in step (b);
(d) calculating the difference between the mean miRNA levels calculated in step (c);
(e) comparing the differences between the mean miRNA levels calculated in step (d) between all studied miRNAs and selecting as potential biomarker pairs those miRNA pairs for which the difference calculated in step (d) for one miRNA is at least 1.5 times the difference calculated for the other miRNA;
(f) calculating Spearman's rank correlation coefficient ($\rho$) for each potential biomarker miRNA pair selected in step (e), and (g) identifying the miRNA pair as a suitable biomarker pair for assessing or monitoring the progression of aging, or the status of aging, if its ($\rho$) value calculated in step (f) is at least 0.8.

In another embodiment, the invention provides a method for selecting a biomarker miRNA pair for diagnosis and/or monitoring of aging, said method comprising the following steps:
(a) selecting at least four miRNAs known to be enriched in an organ affected by aging;
(b) measuring the level of each miRNA selected in step (a) in bodily fluid samples from two subject cohorts;
(c) calculating Spearman's rank correlation coefficient ($\rho$) for all possible pairs of individual miRNAs measured in step (b);
(d) selecting as potential biomarker pairs those miRNA pairs which have the ($\rho$) value calculated in step (c) of at least 0.8;
(e) calculating the mean level of each miRNA selected in step (d);
(f) calculating the difference between the mean miRNA levels calculated in step (e);
(g) identifying a miRNA pair as a suitable biomarker pair for diagnosis and/or monitoring of aging if the difference calculated in step (f) for one miRNA is at least 1.5 times the difference calculated for the other miRNA.

In a further embodiment, the invention provides a method for selecting a biomarker miRNA pair for diagnosis and/or monitoring of aging, said method comprising the following steps:
(a) selecting at least four miRNAs known to be enriched in an organ or tissue affected by aging;
(b) measuring the level of each miRNA selected in step (a) in bodily fluid samples from two subject cohorts;
(c) calculating Spearman's rank correlation coefficient ($\rho$) for all possible pairs of individual miRNAs measured in step (b);
(d) selecting as potential biomarker pairs those miRNA pairs which have the ($\rho$) value calculated in step (c) of at least 0.8;
(e) calculating P-value of two subject cohorts separation for each miRNA pair selected in step (d), and
(f) identifying a miRNA pair as a suitable biomarker pair for diagnosis and/or monitoring of aging if this pair differentiates two subject cohorts with a statistically significant P-value.

In another embodiment, the invention provides a computer-implemented method for selecting a biomarker miRNA pair for diagnosis and/or monitoring of aging, said method comprising the following steps:
(a) selecting a group of miRNAs known to be enriched in an organ or tissue affected by aging;
(b) measuring the level of each miRNA selected in step (a) in bodily fluid samples from two subject cohorts;
(c) electronically calculating the mean level of each miRNA measured in step (b);
(d) electronically calculating a difference between the mean miRNA levels calculated in step (c);
(e) selecting from the group of measured miRNAs a set of potential miRNA pairs each comprising a first miRNA and a second miRNA, wherein the calculated difference in the mean level in step (d) of the first miRNA is at least 1.5 times the calculated difference in the mean level of the second miRNA;
(f) electronically calculating the Spearman's rank correlation coefficient ($\rho$) for each potential miRNA pair selected in step (e);
(g) selecting from the set of potential miRNA pairs those miRNA pairs, which are suitable for the diagnosis and/or monitoring of aging, wherein the ($\rho$) value calculated in step (f) is at least 0.8, and
(h) displaying all or part of the miRNA pairs selected in step (g).

In yet another embodiment, the invention provides a computer-implemented method for selecting a biomarker miRNA pair for diagnosis and/or monitoring of aging, said method comprising the following steps:
(a) selecting a group of miRNAs known to be enriched in an organ affected by aging;
(b) measuring the level of each miRNA selected in step (a) in bodily fluid samples from two subject cohorts;
(c) electronically calculating the Spearman's rank correlation coefficient ($\rho$) for all possible pairs of individual miRNAs measured in step (b);
(d) selecting from the group of measured miRNAs a set of potential biomarker miRNA pairs, wherein the ($\rho$) value calculated in step (c) is at least 0.8;
(e) electronically calculating the mean level of each miRNA selected in step (d);
(f) electronically calculating the difference between the mean miRNA levels calculated in step (e);
(g) selecting from the group of measured miRNAs a set of suitable miRNA biomarker pairs each comprising a first miRNA and a second miRNA, wherein for each suitable biomarker miRNA pair, the calculated difference in the mean level in step (f) of the first miRNA is at least 1.5 times the calculated difference in the mean level of the second miRNA, and
(h) displaying all or part of the suitable biomarker miRNA pairs selected in step (g).

In a further embodiment, the invention provides a computer-implemented method for selecting a biomarker miRNA pair for diagnosis and/or monitoring of aging, said method comprising the following steps:
(a) selecting a group of miRNAs known to be enriched in an organ affected by aging;
(b) measuring the level of each miRNA selected in step (a) in bodily fluid samples from two subject cohorts;
(c) electronically calculating the Spearman's rank correlation coefficient ($\rho$) of the levels measured in step (b) for all possible pairs of individual miRNAs;
(d) selecting from the group of measured miRNAs a set of potential biomarker miRNA pairs, wherein the ($\rho$) value calculated in step (c) is at least 0.8;
(e) electronically calculating P-value of two subject cohorts separation for each miRNA pair selected in step (d);
(f) selecting a miRNA pair as a suitable biomarker pair for diagnosis and/or monitoring of aging if this miRNA pair differentiates two subject cohorts with a statistically significant P-value, and
(g) displaying all or part of the suitable biomarker miRNA pairs selected in step (f).

Non-limiting examples of the methods which can be used to measure miRNA level in any of the above methods of the invention include, e.g., RT-PCR-based methods, miRNA array-based methods, new generation sequencing, and hybridization.

Non-limiting examples of the bodily fluid samples which can be used in any of the above methods of the invention include, e.g., plasma, serum, cerebrospinal fluid (CSF), urine, and saliva.

In any of the above methods of the invention, the subjects can be, e.g., humans or experimental animals.

In any of the above methods of the invention, any two cohorts can be compared. Non-limiting examples of such cohorts include, e.g., aging versus control [e.g., age, gender and ethnicity-matched healthy subjects], two age groups, [e.g., 20-50 years old versus 60-80 years old], males versus females [e.g., age and ethnicity-matched], two different ethnic or racial groups [e.g., age and gender-matched], etc.).

Spearman's rank correlation coefficient ρ used in the methods of the invention defined as:

$$\rho = 1 - \frac{6\sum d_i^2}{n(n^2-1)},$$

wherein
$d_i$—difference between ranks for the sample i;
n—size of the cohort.

A minimal number of samples sufficient for obtaining a statistically significant difference between two cohorts in the above methods of the invention can be calculated by a standard formula for case-control study (see, e.g. Eng J. Radiology 2003, 227:309-313).

In the methods of the invention, a statistically significant P-value can be calculated using any method known in the art. Non-limiting examples of such methods are Student's t-test (for samples with normal distribution) and Mann-Whitney test (for samples with non-random distribution) (Mann and Whitney, Annals Math Stat. 1947, 18: 50-60). P-value ≥0.05 is usually accepted as statistically significant. If numerous potential biomarkers are tested Bonferroni correction can be applied.

Statistical calculations may be performed through the use of software methods, such as applications designed in .NET technology using a set of .NET statistical packages. Mann-Whitney U-tests may be used to evaluate the significance of the differences between the two groups of subjects in the various miRNA pairs. Receiver operating characteristic (ROC) curves can be constructed, and the area under the ROC curves (AUC), sensitivity, specificity, and accuracy of the miRNA pairs and their combinations can be calculated. To reduce instrumental errors, calibration curves for each miRNA may be generated using synthetic miRNAs. Average miRNA concentrations and correlations between individual miRNAs or miRNA pairs and age may be calculated using copy numbers. Effective pair combinations (miRNA classifiers) can be defined using logistic regression. The residual standard deviation (RSD) of the linear regression may be used to estimate age prediction power of the miRNA biomarker pairs. Effective pair combinations that correlated with age can be created using pair data averaging.

The data obtained in the Examples herein demonstrates the potential use of circulating brain-enriched miRNAs as biomarkers of brain aging. Even without finding a brain-enriched miRNA (or a miRNA pair) whose levels in plasma correlated with the wide age range of 26-75 years, the data show established miRNA pairs that correlate with age in sex-stratified groups covering 10-year spans. In a subject, various determinations may be made to assign the subject to a 10-year span. Additional statistical analysis can be performed to more precisely assign the subject to a 5-year span, a 3-year span, a 1-year span, or even a 6-month span. Larger studies can be undertaken to better define the exact age spans when the miRNA levels change.

Age-associated changes in plasma concentrations of the brain-enriched miRNAs tested in this study are likely reflective of molecular and physiological processes in the brain, such as the following: (i) miRNA expression; (ii) miRNA secretion/excretion; (iii) rate of synapse dysfunction and loss, especially in older subjects; (iv) neuronal death; (v) blood supply; and (vi) blood-brain barrier permeability.

Substantially identical and overlapping patterns of decreases and increases in plasma levels of multiple brain-enriched miRNAs indirectly indicate that these are centrally regulated phenomena. The different dynamics in the plasma concentrations of brain-enriched miRNAs in female and male subjects, which are particularly prominent in the 46-65-year-old group, coincide with the changes in sex hormone levels. Maximum levels of miR-134 family members and certain other miRNAs in the plasma of female subjects are reached in the 46-55-year-old group. Interestingly, this result corresponds to perimenopause and menopause in women, when a significant drop in circulating estradiol occurs.

In males, peaks in the miRNA concentrations are reached in the 56-65-year-old group, possibly reflecting slower changes in testosterone decreases. Thus, one can hypothesize that sex hormones modulate miRNA synthesis and/or secretion. This concept is in agreement with the recently reported inhibition of members of the miR-134 family (miR-127, miR-134, miR-370, miR-432) and other miRNAs by estradiol in the neonatal hypothalamus.

The various methods of assessing the progression of aging or even the aging status (i.e. assignment of a subject to a 10-year span, 5-year span, a 3-year span, a 1-year span, or even a 6-month span) may be coupled with further diagnostic testing of a disease or disorder, particularly if the subject's aging status exceeds the chronological age of the subject. The aging status may reflect that particular subject's cumulate decline of functional capacity and stress resistance that are associated with increased risk of morbidity and mortality.

For example, a male subject assigned to an aging status of a 55 year old male, but who has a chronological age of 47 years old, may have an underlying condition or disease that has accelerated aging in the subject or modulated the above-described regulatory systems. In some embodiments, if the subject's aging status exceeds chronological age by 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, etc. then the subject may be identified for further diagnostic tests.

The various methods described herein may be used to assess the effect of one or more lifestyle, treatment, and medication changes on the rate of aging. First, the subject is tested by any of the methods described in the application to determine aging status. Advanced statistical methods could be used to precisely assign a subject to an aging status in a one-month span. The subject may then undertake a lifestyle change, a therapy and/or a medication change to assess the effect on the rate of aging. The subject may then be retested after a set number of months from the initial test. If the aging status has increased by a fewer number of months than by the set number of months that occurred between the first test and the retest, then the lifestyle, treatment, and/or medication change may reduce the rate of aging in that subject. For example, a subject who adopts more exercise, more cognitive demanding work, ingests antioxidants, and/or obtains treatment for an underlying condition may benefit from knowing that the rate of aging is reduced. Such knowledge may motivate the subject to continue these pursuits.

The methods described herein provide a particular advantage in yielding gender-specific information on how to delay aging. For example, a particular lifestyle change may be more beneficial in women than in men for slowing aging. The gender-specific markers described in the application provide for a substantial benefit in assessing how a change in lifestyle, a therapy, a medication or other pharmaceutical substance, can slow the rate of aging.

For measuring lifestyle change, the subject may undertake a low-calorie diet that modulates one or more of the IGF, sirtuin, mTOR and other pathways. The subject may be able to significantly slow the rate of aging, as reflected in reduced advancement of the subject's aging status. Testing approaches may be undertaken to determine which lifestyle changes, treatment changes and substances are most effective in slowing the rate of aging.

Critical for developing and testing approaches to sustaining healthy living and delaying aging is the development and validation of minimally invasive, cost-effective biomarkers of aging. In addition, quantitative definition of biomarker ranges that are characteristic of normal aging is also important for early detection of aging-related diseases. For example, synapse dysfunction and loss, ultimately followed by neuronal death, accompany normal aging [Masliah E, et al. J. Alzheimer's Dis. 2006, 9 (3 Suppl):91-99; Dorszewska J. Aging Clin Exp Res. 2013 April; 25(1):25-34; 14. Bredesen D E. Aging Cell. 2004; 3:255-259]. However, rapid progression of these processes in a particular brain region could be an early indication of a neurodegenerative disease affecting this region. The same is true for other organs and tissues.

The methods described herein may be effective in one or more of the following: (1) predict the rate of aging and assess where a person is in his/her lifespan better than the person's chronological age; (2) be minimally invasive; and (3) useful in animal models, as well as in humans, since preliminary testing of essentially all drug candidates and many therapeutic regimens is performed in non-human subjects. These criteria have been proposed by the American Federation for Aging Research and the European MARK-AGE consortium. Various miRNA and combinations of miRNA markers disclosed herein can 1) predict the rate of aging and assess where a person is in his/her lifespan better than the person's chronological age; (2) be minimally invasive; and (3) useful in animal models, as well as in humans, since preliminary testing of essentially all drug candidates and many therapeutic regimens is performed in non-human subjects.

Any of the miRNA biomarkers described herein may be used in conjunction with other molecular biomarkers of aging, such as telomerase length shortening and DNA methylation. Larger studies, including longitudinal ones, may be undertaken for determining the use of miRNA biomarker classifiers for use in clinical research. Other circulating organ-enriched miRNAs can be tested as biomarkers of aging in respective organs in tissues, which in addition may indicate one or more other serious pathologic processes besides aging.

Kits of the Invention

In conjunction with the above diagnostic, monitoring and screening methods, the present invention provides various kits comprising one or more primer and/or probe sets specific for the detection of the biomarker miRNA pairs.

Such kits can further include primer and/or probe sets specific for the detection of additional normalizer miRNAs.

Such kits can be useful for direct miRNA detection in bodily fluid samples isolated from patients or can be used on purified total RNA or miRNA samples.

A kit of the invention can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs). Alternatively (or in addition), a kit can include reagents for performing a hybridization assay. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include miRNA isolation or purification means as well as positive and negative controls. A kit can also include a notice associated therewith in a form prescribed by a governmental agency regulating the manufacture, use or sale of diagnostic kits. Detailed instructions for use, storage and troubleshooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Any of the compositions or reagents described herein may be components in a kit.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1. Selection of miRNAs for Analysis of Sex- and Age-Dependent Changes of Circulating miRNAs In the first set of experiments 38 miRNAs were pre-selected (Table 2), many of which were enriched in PG and other brain areas. The pre-selected set of miRNAs included brain-enriched miRNAs additional miRNAs that are both (i) enriched in different brain regions, neurons and glial cells, and (ii) detectable in plasma. Plasma samples were collected at the New York Blood Center from donors who had no known diseases and were qualified as healthy donors. Blood was collected in 6-ml lavender-top $K_2$EDTA tubes and then centrifuged at 4° C. at 2,000×g. Plasma was aliquoted into RNase free 2 ml round bottom microcentrifuge tubes (Biotix, San Diego, Calif. and frozen at −80° C. within 2 hours of the blood collection.

Plasma samples were collected from four groups (10 subjects in each group): women and men 26-35 years old ("young males" and "young females") and 56-65 years old ("old males" and "old females").

miRNA isolation and qRT-PCR analysis were performed in accordance with the following protocol (Asuragen, Austin, Tex.). RNA was extracted from 1 ml of plasma using a TRIzol treatment and silica (Ambion Glass Fiber Microcolumn)-binding protocol (http://asuragen.com/wp-content/uploads/2016/05/biomarkers.pdf). Single-target qRT-PCR was performed using the TaqMan Reverse Transcription Kit and miRNA-specific stem-loop primers (Thermo Fisher). QC of miRNA preps was performed by testing two ubiquitous miRNAs in each plasma prep; all samples with values within two standard deviations of the average value qualified as acceptable for analysis. miRNAs with cycle thresholds (Ct) >37 were excluded from the analysis of each respective sample. The RT step for generation of cDNA from selected miRNAs was performed in triplicate using miRNA-specific primers, and 2-µl plasma equivalents were present in the final PCR. Calibration curves for each miRNA were generated to calculate the miRNA concentration in copy numbers.

Pre-selected miRNAs were measured by quantitative RT-qPCR. miR-149, miR-154, miR-184, miR-369-3p, miR-129-3p were found to be barely detectable in this experiment and were thus excluded from the analysis. Cts for miR-204, miR-212 and miR-96 in many samples were higher than 36 and, although the data were included in the analysis, these miRNAs were not selected for the Example 2 study.

Since two aspects (age-related changes and gender-dependent differences) are important in this project, the four pair-wise differences between the groups of research participants were taken into account in selection of miRNAs for the larger study, described in the Example 2: (1) young and old males; (2) young and old females; (3) young males and young females; and (4) old males and old females Age-related changes and sex-dependent differences in the concentrations of circulating brain-enriched miRNAs in plasma were compared as follows: (1) "young" vs. "old" males; (2) "young" vs. "old" females; (3) "young" males vs. "young" females; and (4) "old" males vs. "old" females (FIG. 1, Table 3).

Although the number of samples in each group was relatively small, FIGS. 6A-6F, Table 3 and Table 4 demonstrate that the groups were effectively distinguished from each other by the miRNA pairs and their combinations (classifiers). These data indicated that the plasma concentrations of certain brain-enriched miRNAs are sex- and age-dependent. miRNAs comprising the most effective pairs were chosen for more detailed analyses in the larger second stage of the study.

The rightmost column of Table 3 lists the following miRNAs that were selected for the experiments of Example 2: miR-7, let-7e, miR-127, miR-132, miR-135a, miR-181a, miR-182, miR-195, miR-323-3p, miR-370, miR-375, miR-382, miR-411, miR-433, miR-487b, miR-874, miR-9, miR-99a, miR-134, and miR-491.

FIG. 1 presents raw data for miRNAs of the miR-134 family. The data demonstrate that these miRNAs behave similarly in the four cohorts tested. the present inventors note that many miRNA pairs and their combinations effectively differentiated the four cohorts from each other with up to 100% accuracy.

TABLE 2 miRNAs analyzed in the Example 1.

|   | miRNA | Brain enrichment | Present in synapses | Family |
|---|---|---|---|---|
| 1 | Let-7e | Cer, MB, PG | + | miR-132 |
| 2 | miR-7 | PG, FC, Hip | + | |
| 3 | miR-9 | FC, MB, Hip, Cer | | miR-132 |
| 4 | miR-16 | Ubiquitous, PG | | |
| 5 | miR-96 | PG | | |
| 6 | miR-99a | PG, MB, FC | | |
| 7 | miR-107 | FC, PG, Hip, MB | | miR-132 |
| 8 | miR-127-3p | PG, MB, FC | + | miR-134 |
| 9 | miR-128a | FC, Hip, Cer, HPT | + | miR-132 |
| 10 | miR-129-3p | FC, MB | | |
| 11 | miR-132 | PG, Hip, FC, MB | + | miR-132 |
| 12 | miR-134 | MB, Hip, PG | + | miR-134 |
| 13 | miR-135a | PG, Hip | + | miR-132 |
| 14 | miR-149 | FC, MB | | |
| 15 | miR-153 | Hip, FC | | |
| 16 | miR-154 | PG, FC, MB | | |
| 17 | miR-181a | MB, FC | | miR-132 |
| 18 | miR-182 | PG | | |
| 19 | miR-184 | Hip, PG | | |
| 20 | miR-195 | PG, MB | | |
| 21 | miR-200a | PG | | |
| 22 | miR-204 | Cer, MB, PG | | |
| 23 | miR-323-3p | FC, Hip, MB | + | miR-134 |
| 24 | miR-335-5p | PG, Hip | | miR-132 |
| 25 | miR-338 | FC, Hip, MB, Cer | | |
| 26 | miR-370 | FC, PG | + | miR-134 |
| 27 | miR-369 | PG | | |
| 28 | miR-375 | PG | | |
| 29 | miR-382 | Hip, FC | + | miR-134 |
| 30 | miR-410 | PG, MB | | miR-134 |
| 31 | miR-411 | PG, Hip, FC | | miR-134 |
| 32 | miR-433 | PG, MB | + | miR-134 |
| 33 | miR-451 | Ubiquitous/PG, MB, | | |
| 34 | miR-485-5p | Hip | + | miR-134 |
| 35 | miR-487b | PG, FC, MB | | miR-134 |
| 36 | miR-488 | Hip, Cer | | |
| 37 | miR-491-5p | MB, FC | + | miR-132 |
| 38 | miR-874 | Cer, Hip | + | miR-132 |

Cer—Cerebellum;
FC—Frontal Cortex;
Hip—Hippocampus;
HPT—Hypothalamus;
MB—Midbrain;
PG—Pituitary Gland.

All statistical calculations were performed through the use of an application was designed in .NET technology using a set of .NET statistical packages. Mann-Whitney U-tests were used to evaluate the significance of the differences between the two groups of subjects in the various miRNA pairs. Receiver operating characteristic (ROC) curves were constructed, and the area under the ROC curves (AUC), sensitivity, specificity, and accuracy of the miRNA pairs and their combinations were calculated. To reduce instrumental errors, calibration curves for each miRNA were generated using synthetic miRNAs. Average miRNA concentrations and correlations between individual miRNAs or miRNA pairs and age were calculated using copy numbers. Effective pair combinations (miRNA classifiers) were defined using logistic regression. The residual standard deviation (RSD) of the linear regression was used to estimate age prediction power of the miRNA biomarker pairs. Effective pair combinations that correlated with age were created using pair data averaging.

TABLE 3

Table of Ct differences for various miRNAs tested in four groups of research participants (Example 1).

| | Young male - Young female | Young male - Old male | Young female - Old female | Old male - Old female | Selected for using in Example 2 |
|---|---|---|---|---|---|
| miR-7 | −0.33 | 0.57 | 0.23 | −0.66 | miR-7 |
| Let-7e | 0.25 | 0.7 | 0.2 | −0.26 | let-7e |
| miR-107 | 0.01 | 0.29 | 0.15 | −0.13 | |
| miR-127 | 0.09 | −0.04 | −0.97 | −0.83 | miR-127 |
| miR-128a | −0.06 | 0.19 | 0.25 | 0 | |
| miR-132 | 0.34 | 0.74 | 0.35 | −0.05 | miR-132 |
| miR-135a | 0.39 | 1.49 | 0.53 | −0.57 | miR-135a |
| miR-16 | −0.11 | 0.4 | 0.22 | −0.29 | |
| miR-181a | 0.49 | 0.97 | 0.81 | 0.32 | miR-181a |
| miR-182 | −0.13 | 0.72 | 0.85 | −0.01 | miR-182 |
| miR-195 | 0 | 0.61 | 0.61 | −0.01 | miR-195 |
| miR-200a | 0.1 | −0.24 | 0.48 | 0.82 | |
| miR-323-3p | 0.13 | 0.07 | −0.67 | −0.61 | miR-323-3p |
| miR-335-5p | 0.08 | 0.17 | 0.35 | 0.26 | |
| miR-338-3p | −0.15 | −0.24 | 0.15 | 0.24 | |
| miR-370 | 1.44 | 0.61 | −1.6 | −0.77 | miR-370 |
| miR-375 | −0.39 | −0.16 | 1.43 | 1.2 | miR-375 |
| miR-382 | 0.33 | 1.03 | 0.39 | −0.31 | miR-382 |
| miR-410 | 0.21 | 0.51 | −0.18 | −0.48 | |
| miR-411 | 0.71 | 0.65 | −0.36 | −0.3 | miR-411 |
| miR-433 | 0.24 | 0.05 | −0.91 | −0.73 | miR-433 |
| miR-485-5p | 0.48 | 0.33 | −0.3 | −0.15 | |
| miR-487b | 0.38 | 0.6 | −0.17 | −0.39 | miR-487b |
| miR-874 | 0.1 | 0.44 | 0.61 | 0.28 | miR-874 |
| miR-9 | 0.67 | 0.64 | 0.24 | 0.27 | miR-9 |
| miR-9* | 0.32 | −0.31 | −0.08 | 0.55 | |
| miR-99a | 0.38 | 0.98 | 0.82 | 0.23 | miR-99a |
| miR-134 | 0.25 | 0.49 | −0.81 | −1.05 | miR-134 |
| miR-451 | −0.17 | 0.27 | 0.23 | −0.21 | |
| miR-491 | −0.03 | 0.28 | 0.06 | −0.24 | miR-491 |

TABLE 4

The P-values for differentiation between old males and young males and AUC (Area under ROC curve) for the best miRNA pairs are presented in Table 4, below.

| Pairs | Sens | Spec | Accur | AUC | P-Value |
|---|---|---|---|---|---|
| miR-135a/miR-128a | 0.90 | 0.90 | 0.90 | 0.99 | 1.20E−04 |
| miR-382/miR-127 | 1.00 | 0.70 | 0.85 | 0.99 | 1.20E−04 |
| miR-212/miR-9* | 0.90 | 1.00 | 0.95 | 0.98 | 2.90E−04 |
| miR-181a/miR-9* | 1.00 | 0.90 | 0.95 | 0.98 | 2.20E−04 |
| miR-132/miR-9* | 0.90 | 0.90 | 0.90 | 0.98 | 2.20E−04 |
| miR-135a/miR-129-3p | 0.84 | 0.84 | 0.84 | 0.97 | 3.80E−04 |
| miR-135a/miR-107 | 0.86 | 0.86 | 0.86 | 0.97 | 3.80E−04 |
| miR-99a/miR-9* | 0.94 | 0.73 | 0.83 | 0.97 | 3.80E−04 |
| miR-212/miR-129-3p | 0.77 | 0.87 | 0.82 | 0.96 | 3.80E−04 |
| miR-181a/miR-107 | 0.78 | 0.78 | 0.78 | 0.96 | 8.50E−04 |
| miR-411/miR-127 | 0.88 | 0.69 | 0.79 | 0.96 | 6.60E−04 |
| miR-212/miR-128a | 0.86 | 0.77 | 0.81 | 0.95 | 6.60E−04 |

TABLE 4-continued

The P-values for differentiation between old males and young males and AUC (Area under ROC curve) for the best miRNA pairs are presented in Table 4, below.

| Pairs | Sens | Spec | Accur | AUC | P-Value |
|---|---|---|---|---|---|
| miR-382/miR-134 | 0.82 | 0.72 | 0.77 | 0.94 | 1.10E−03 |
| miR-135a/miR-107 + miR-382/miR-134 + miR-212/miR-128a | 1.00 | 1.00 | 1.00 | 1.00 | 6.70E−05 |

The P-values for differentiation between old females and young females and AUC (Area under ROC curve) for the best miRNA pairs are presented in Table 5, below.

TABLE 5

| Pairs | Sens | Spec | Accur | AUC | P-Value |
|---|---|---|---|---|---|
| miR-382/miR-323-3p | 0.60 | 1.00 | 0.80 | 0.99 | 1.20E−04 |
| miR-99a/miR-370 | 0.70 | 1.00 | 0.83 | 0.98 | 4.20E−04 |
| miR-195/miR-16 | 0.90 | 0.90 | 0.90 | 0.98 | 2.90E−04 |
| miR-135a/miR-370 | 0.70 | 1.00 | 0.83 | 0.98 | 4.20E−04 |
| miR-382/miR-127 | 0.90 | 0.90 | 0.90 | 0.98 | 2.20E−04 |
| miR-382/miR-433 | 0.90 | 0.80 | 0.85 | 0.98 | 2.20E−04 |
| miR-99a/miR-433 | 0.80 | 0.90 | 0.85 | 0.96 | 8.50E−04 |
| miR-99a/miR-154 | 0.62 | 0.90 | 0.74 | 0.96 | 1.10E−03 |
| miR-181a/miR-370 | 1.00 | 0.75 | 0.89 | 0.96 | 7.80E−04 |
| miR-181a/miR-9* | 0.86 | 0.86 | 0.86 | 0.96 | 5.00E−04 |
| miR-181a/miR-491 | 0.80 | 0.90 | 0.85 | 0.96 | 6.60E−04 |
| miR-382/miR-370 | 0.88 | 0.73 | 0.81 | 0.96 | 1.10E−03 |
| miR-375/miR-433 | 0.80 | 0.80 | 0.80 | 0.94 | 1.10E−03 |
| miR-375/miR-433 + miR-135a/miR-370 + miR-382/miR-323-3p | 1.00 | 1.00 | 1.00 | 1.00 | 6.70E−05 |

The P-values for differentiation between all old subjects (old males plus old females) and all young subjects (young males plus young females) and AUC (Area under ROC curve) for the best miRNA pairs are presented in Table 6, below.

TABLE 6

| Pairs | Sens | Spec | Accur | AUC | P-Value |
|---|---|---|---|---|---|
| miR-181a/miR-9* | 1.00 | 0.85 | 0.93 | 0.96 | 6.00E−07 |
| miR-135a/miR-9* | 0.85 | 1.00 | 0.93 | 0.95 | 2.30E−06 |
| miR-382/miR-127 | 0.88 | 0.83 | 0.86 | 0.95 | 1.30E−06 |
| miR-382/miR-134 | 0.86 | 0.81 | 0.84 | 0.95 | 1.70E−06 |
| miR-382/miR-323-3p | 0.82 | 0.82 | 0.82 | 0.94 | 2.90E−06 |
| miR-99a/miR-9* | 0.80 | 0.80 | 0.80 | 0.92 | 7.00E−06 |
| miR-204/miR-9* | 0.84 | 0.84 | 0.84 | 0.92 | 9.00E−06 |
| miR-181a/miR-107 | 0.75 | 0.80 | 0.78 | 0.91 | 1.60E−05 |
| miR-382/miR-433 | 0.84 | 0.69 | 0.76 | 0.91 | 7.00E−06 |
| miR-135a/miR-128a | 0.80 | 0.70 | 0.75 | 0.89 | 5.80E−05 |
| miR-487b/miR-127 | 0.75 | 0.75 | 0.75 | 0.88 | 4.60E−05 |
| miR-135a/miR-338-3p | 0.79 | 0.74 | 0.77 | 0.87 | 1.50E−04 |
| miR-99a/miR-338-3p | 0.80 | 0.65 | 0.73 | 0.87 | 1.40E−04 |
| miR-204/miR-9* + miR-382/miR-127 + miR-382/miR-323-3p | 1.00 | 1.00 | 1.00 | 1.00 | 2.90E−08 |

The P-values for differentiation between young females and young males and AUC (Area under ROC curve) for the best miRNA pairs are presented in Table 7, below.

TABLE 7

| Pairs/Combos | Sens | Spec | Accur | AUC | P-Value |
|---|---|---|---|---|---|
| miR-212/miR-874 | 0.86 | 0.86 | 0.86 | 0.97 | 2.90E−04 |
| miR-212/miR-7 | 0.82 | 0.93 | 0.88 | 0.95 | 8.50E−04 |
| miR-212/miR-195 | 0.83 | 0.73 | 0.78 | 0.94 | 1.40E−03 |
| miR-212/miR-128a | 0.79 | 0.69 | 0.74 | 0.93 | 2.30E−03 |

TABLE 7-continued

| Pairs/Combos | Sens | Spec | Accur | AUC | P-Value |
|---|---|---|---|---|---|
| miR-212/miR-375 | 0.80 | 0.70 | 0.75 | 0.92 | 1.80E−03 |
| miR-212/miR-16 | 0.77 | 0.68 | 0.73 | 0.90 | 2.90E−03 |
| miR-204/miR-128a | 0.78 | 0.78 | 0.78 | 0.90 | 2.90E−03 |
| miR-135a/miR-128a | 0.74 | 0.74 | 0.74 | 0.89 | 5.70E−03 |
| miR-212/miR-184 | 0.67 | 0.74 | 0.70 | 0.89 | 1.70E−02 |
| miR-411/miR-323-3p | 0.76 | 0.76 | 0.76 | 0.89 | 7.00E−03 |
| miR-181a/miR-107 | 0.62 | 0.73 | 0.68 | 0.88 | 7.00E−03 |
| miR-212/miR-182 | 0.80 | 0.70 | 0.75 | 0.88 | 5.70E−03 |
| miR-212/miR-491 | 0.80 | 0.60 | 0.70 | 0.88 | 4.60E−03 |
| miR-181a/miR-16 + miR-135a/miR-128a + miR-212/miR-375 | 1.00 | 1.00 | 1.00 | 1.00 | 6.70E−05 |

The P-values for differentiation between old females and old males and AUC (Area under ROC curve) for the best miRNA pairs are presented in Table 8, below.

TABLE 8

| Pairs/Combos | Sens | Spec | Accur | AUC | P-Value |
|---|---|---|---|---|---|
| miR-212/miR-132 | 0.90 | 1.00 | 0.95 | 0.98 | 2.20E−04 |
| miR-375/miR-7 | 0.90 | 0.80 | 0.85 | 0.97 | 3.80E−04 |
| miR-200a/miR-7 | 0.90 | 0.90 | 0.90 | 0.97 | 5.00E−04 |
| miR-204/miR-7 | 0.77 | 0.86 | 0.82 | 0.96 | 5.00E−04 |
| miR-204/let-7e | 0.84 | 0.73 | 0.79 | 0.95 | 6.60E−04 |
| miR-195/miR-7 | 0.74 | 0.84 | 0.79 | 0.95 | 8.50E−04 |
| miR-382/miR-134 | 0.85 | 0.75 | 0.80 | 0.95 | 8.50E−04 |
| miR-200a/let-7e | 0.71 | 0.80 | 0.76 | 0.94 | 1.80E−03 |
| miR-9*/miR-7 | 0.83 | 0.83 | 0.83 | 0.94 | 8.50E−04 |
| miR-9*/miR-135a | 0.80 | 0.70 | 0.75 | 0.94 | 1.40E−03 |
| miR-212/miR-7 | 0.80 | 0.80 | 0.80 | 0.94 | 8.50E−04 |
| miR-181a/miR-7 | 0.82 | 0.72 | 0.77 | 0.94 | 8.50E−04 |
| miR-874/miR-7 | 0.90 | 0.70 | 0.80 | 0.94 | 6.60E−04 |
| miR-212/miR-132 + miR-382/miR-134 | 1.00 | 1.00 | 1.00 | 1.00 | 6.70E−05 |

The P-values for differentiation between old females and old males and AUC (Area under ROC curve) for the best miRNA pairs are presented in Table 9, below.

TABLE 9

| Pairs/Combos | SENS | SPEC | ACCUR | AUC | P-Value |
|---|---|---|---|---|---|
| miR-212/miR-7 | 0.84 | 0.84 | 0.84 | 0.93 | 8.00E−06 |
| miR-212/miR-132 | 0.82 | 0.77 | 0.79 | 0.92 | 1.10E−05 |
| miR-212/miR-16 | 0.82 | 0.77 | 0.79 | 0.89 | 6.40E−05 |
| miR-204/miR-128a | 0.76 | 0.81 | 0.78 | 0.86 | 2.10E−04 |
| miR-874/miR-7 | 0.67 | 0.77 | 0.72 | 0.85 | 2.80E−04 |
| miR-212/miR-107 | 0.73 | 0.68 | 0.71 | 0.84 | 4.60E−04 |
| miR-212/miR-128a | 0.70 | 0.70 | 0.70 | 0.84 | 5.10E−04 |
| miR-212/miR-195 | 0.64 | 0.79 | 0.72 | 0.84 | 4.60E−04 |
| miR-204/miR-7 | 0.82 | 0.56 | 0.69 | 0.84 | 2.80E−04 |
| miR-9*/miR-7 | 0.75 | 0.75 | 0.75 | 0.84 | 3.80E−04 |
| miR-181a/miR-7 | 0.62 | 0.72 | 0.67 | 0.84 | 2.50E−04 |
| miR-212/miR-874 | 0.69 | 0.69 | 0.69 | 0.83 | 7.40E−04 |
| miR-204/miR-107 | 0.71 | 0.76 | 0.74 | 0.83 | 8.10E−04 |
| miR-212/miR-195 + miR-204/miR-128a + miR-9*/miR-7 | 0.85 | 0.95 | 0.90 | 0.97 | 5.20E−07 |

Example 2. Sex-Dependent Aging-Associated Changes of Plasma Concentrations of Brain-Enriched miRNAs 19 miRNAs selected for this study were measured in plasma samples from 100 participants (5 groups of 26-35, 36-45, 46-55, 56-65 and 66-75 year old subjects, with 10 males and 10 females in each group). Table 9A below shows the age cohorts of the tested normal subjects in Example 2 versus Example 1.

TABLE 9A

| | | Example | |
|---|---|---|---|
| Gender | Age (y.o.) | 1st | 2nd |
| Male | 26-35 | 10 | 10 |
| | 36-45 | — | 10 |
| | 46-55 | — | 10 |
| | 56-65 | 10 | 10 |
| | 66-75 | — | 10 |
| Female | 26-35 | 10 | 10 |
| | 36-45 | — | 10 |
| | 46-55 | — | 10 |
| | 56-65 | 10 | 10 |
| | 66-75 | — | 10 |

FIGS. 2-4 demonstrate age-dependent changes of plasma concentrations of various miRNAs in male and female participants, with an average of 10 subjects in each group. Several observations are of interest: (1) among the tested miRNAs, the concentration of no single miRNA correlates with age in all (male and female) participants; (2) age-dependent changes in miRNA concentrations are different in male and female participants; (3) age-dependent changes of concentrations of some miRNAs, e.g. members of the miR-134 family, are similar in gender-specific cohorts, which suggests that these are centrally regulated processes, as it is highly unlikely that synchronous changes in so many miR-NAs are independent; (4) there were peaks in the plasma concentrations of many miRNAs in the 46-55-year-old females and the 56-65-years-old males and (5) practically all miRNAs with a peak of expression in menopause period of females are enriched in PG.

Correlations of individual miRNAs were then analyzed with age in gender-specific cohorts (FIG. 5 and Table 10). These results demonstrate dramatic differences between males and females for family miR-134 and certain other miRNAs, enriched in PG (see above). Interestingly, the gender-specific differences are most significant in the 46-55 year-old cohorts (the rapid increase of miRNA concentrations in females compared with much slower increase in males), which would reflect the effect of menopause in female participants. This supposition is supported by significantly higher StD of plasma miRNA concentrations in the female 46-55 years old cohort (Table 11).

Figure 9:
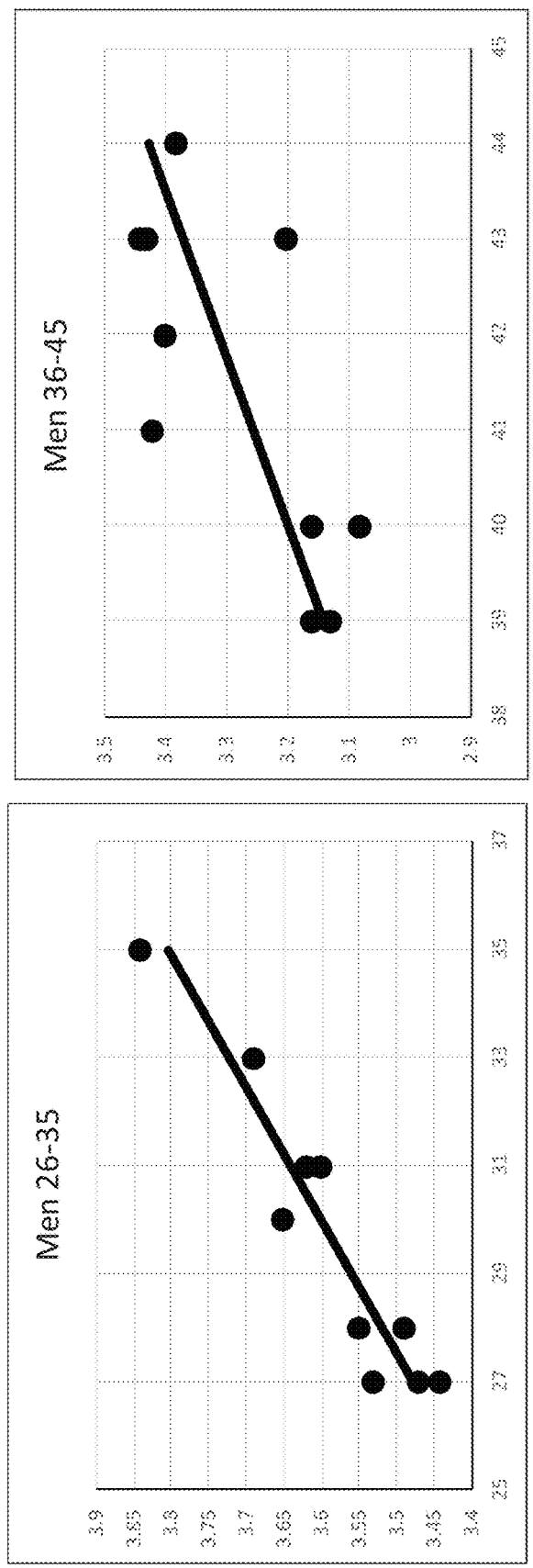
FIG. 9 shows plots of Spearman correlations of some miRNA pair combinations (from Table 14) with subject ages in each of the five male cohorts.
Figure 9:
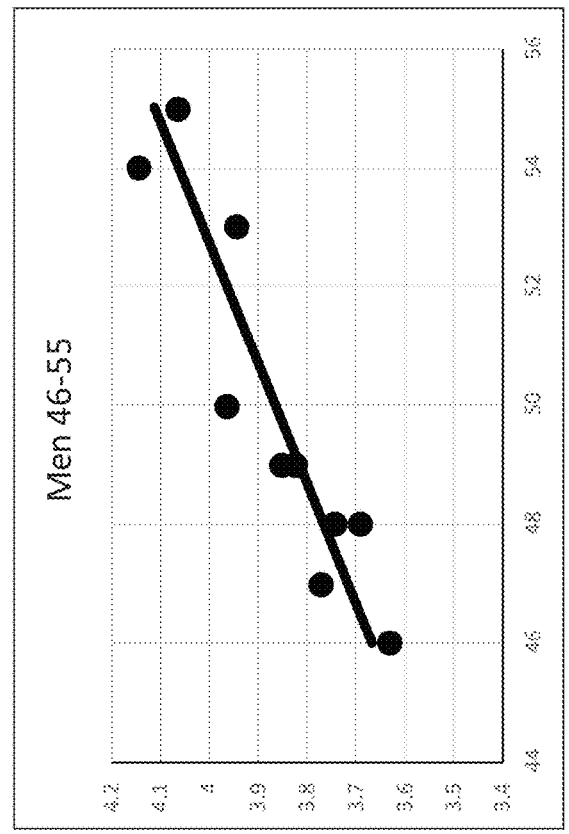
Figure 9:
Figure 9:
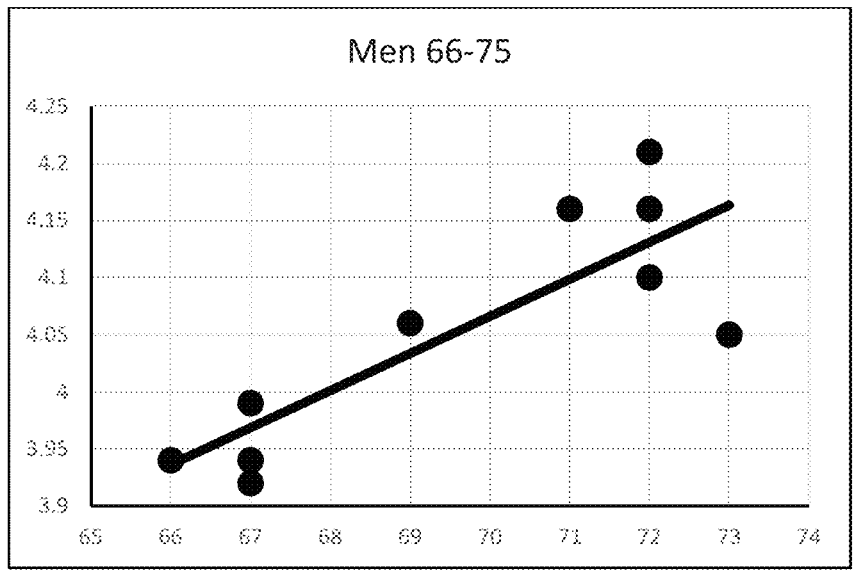
Figure 10:
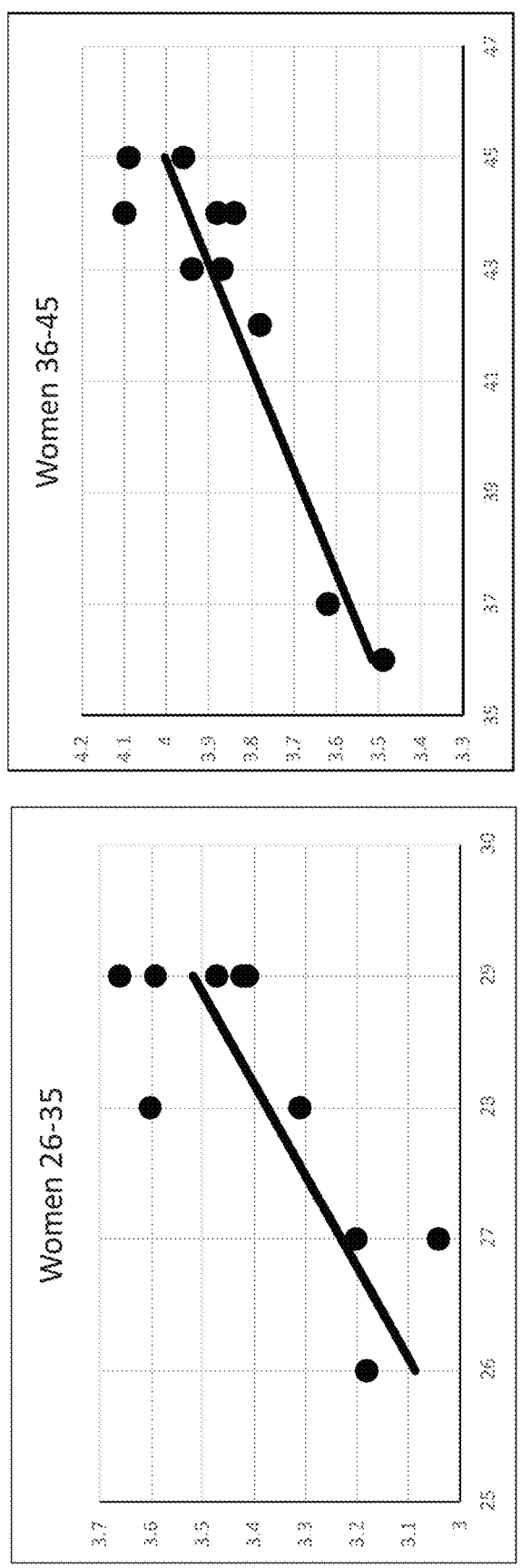
FIG. 10 shows Spearman correlations of some miRNA pair combinations (from Table 14) with subject ages in each of the five female cohorts.
Figure 10:
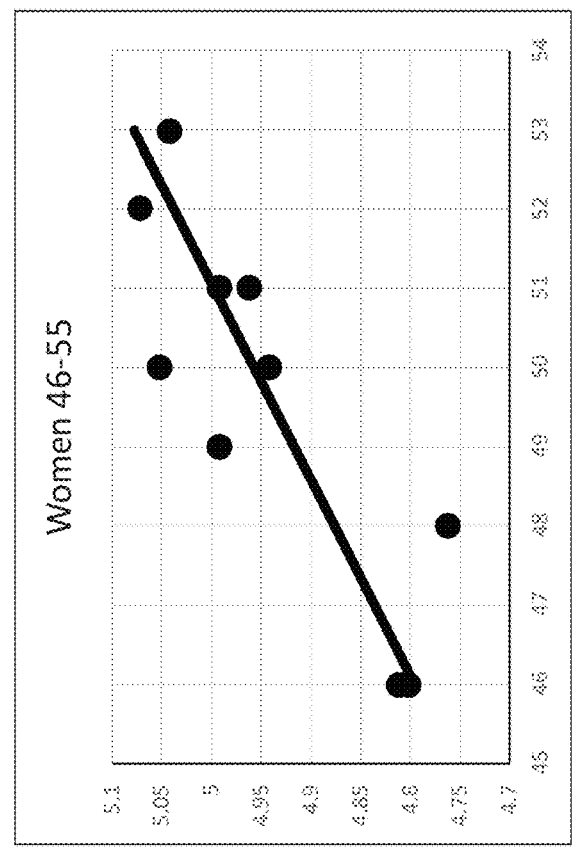
Figure 10:
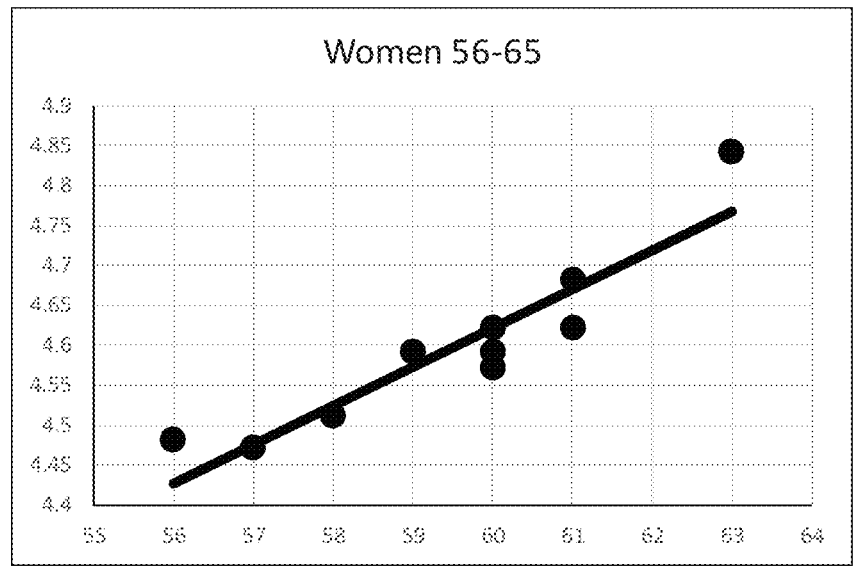
Figure 10:
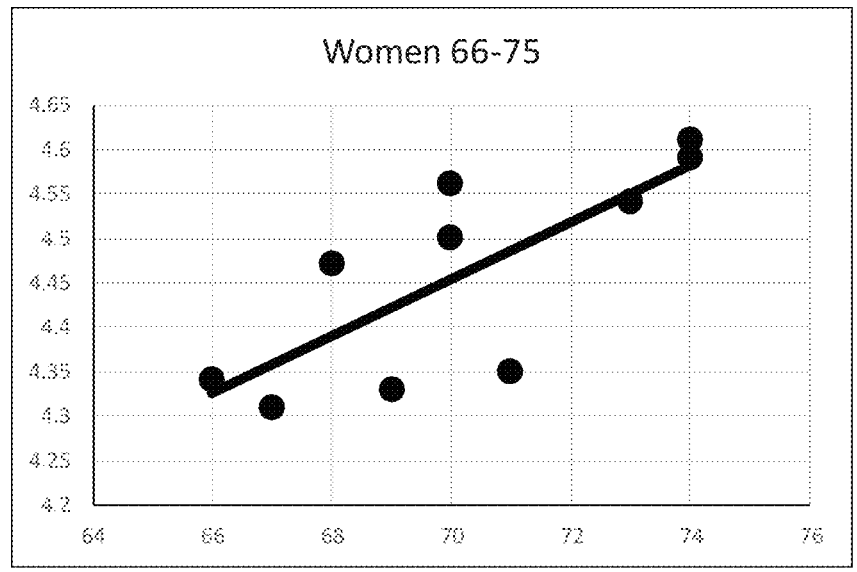

Among the tested miRNAs, no single one could be used as an age biomarker for the entire tested age continuum. More detailed analyses also revealed that there was no miRNA pair formed by the tested miRNAs that correlated with a subject's age over a prolonged time period. The correlations of individual miRNAs were further analyzed with age across 10-year spans in the sex-stratified groups (FIGS. 8, 9A, 9B and 10 and Table 10). From the dynamics of miRNA plasma concentrations (FIG. 7), the age spans, during which correlations between the levels of certain individual miRNAs and subject age are observed, were significantly different for female and male subjects. Further, although the division of age groups was done arbitrarily by 10-year spans, and additional studies are needed to assess the physiological relevance of the present findings, the age groups were effectively separated from each other by multiple miRNA pairs and their combinations (FIG. 10 and Table 4).

miRNA pairs whose correlations with age, particularly in the sex-stratified groups, that were found to be statistically significant are presented in FIG. 11 and Table 13.

These data demonstrated that miRNA pairs and classifiers of brain-enriched miRNAs circulating in plasma can be potentially used as aging biomarkers during specific age spans.

TABLE 10

Figure 5A:
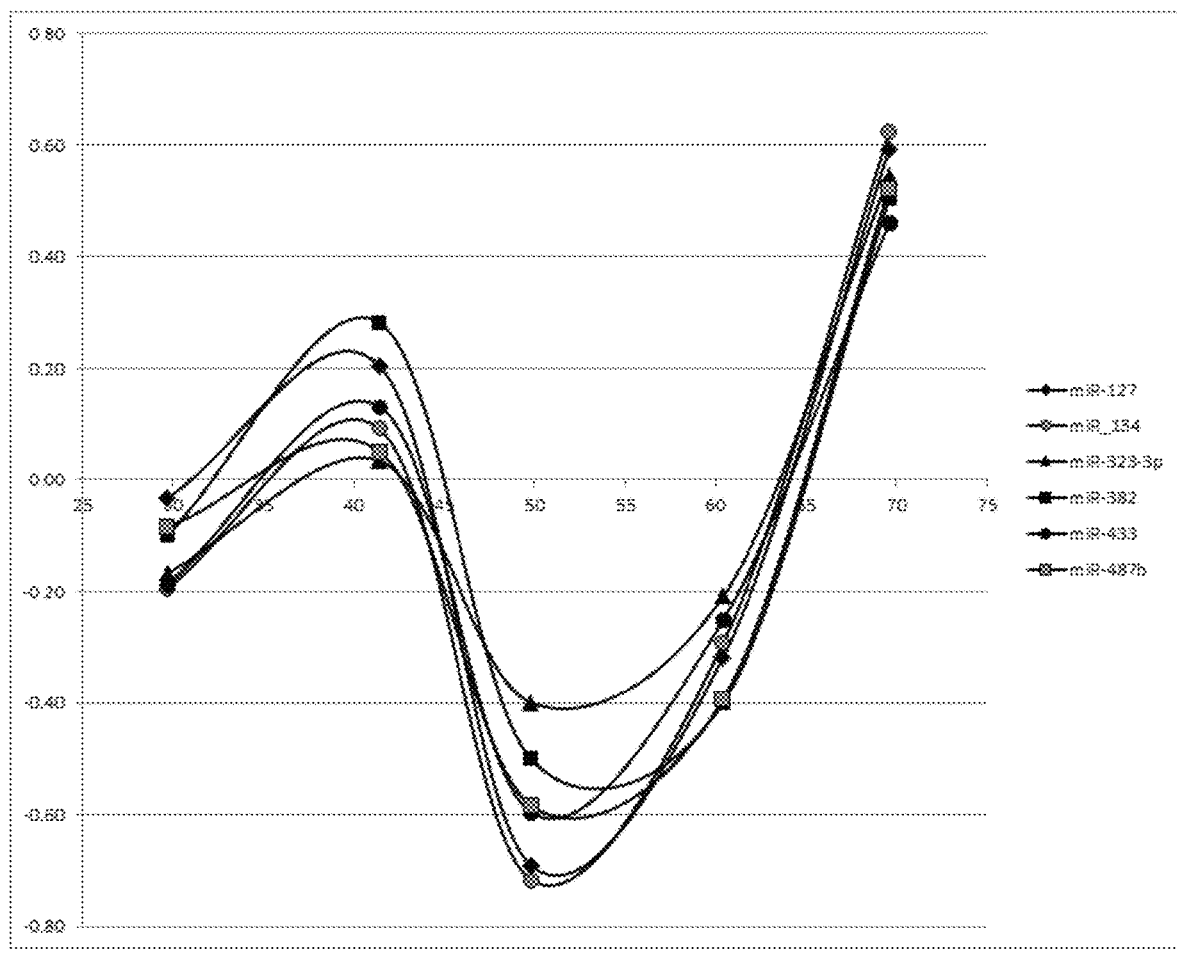
FIGS. 5A-B show correlation of miRNA plasma concentrations with age in male (A) and female (B) participants. Scatter and smooth line graphs are presented. x-axis: age, y axis: correlation of miRNA plasma concentration with age in each of five subject groups.
Figure 5B:
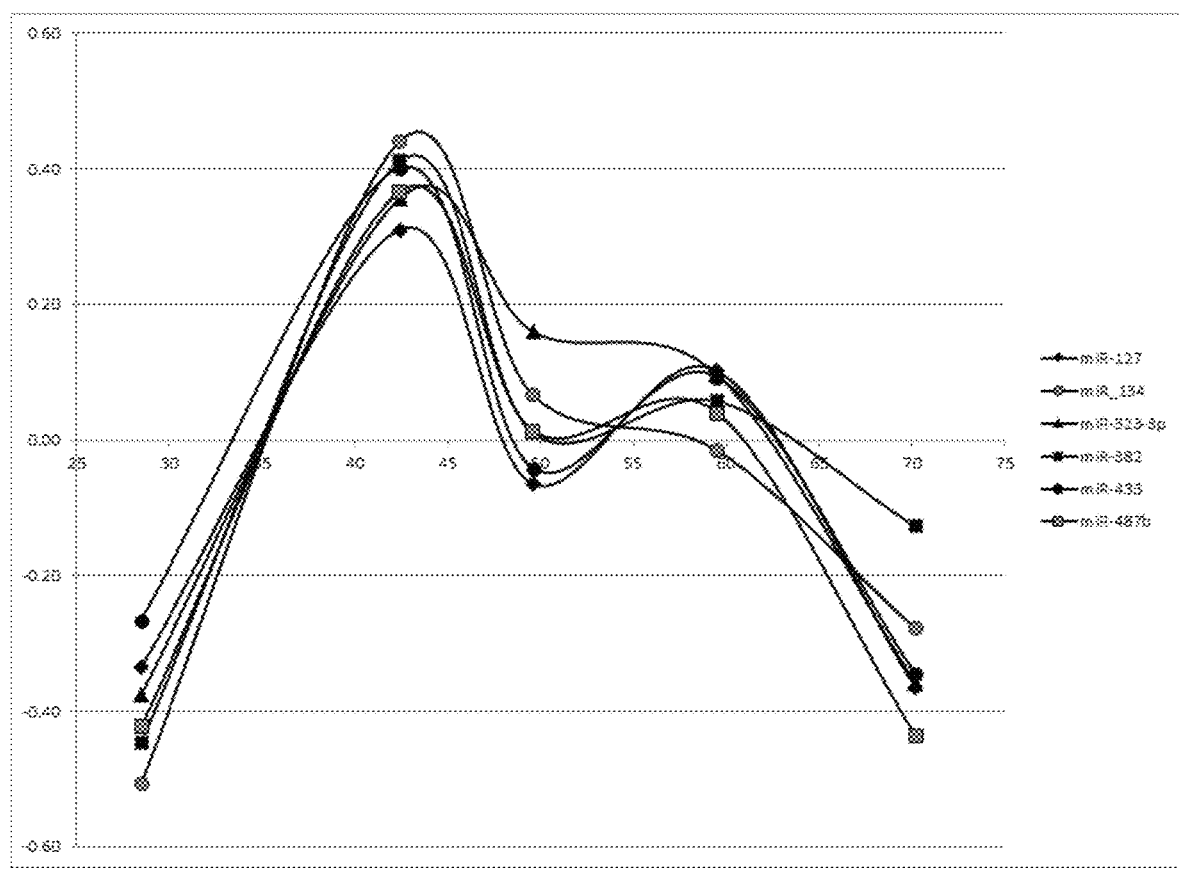
Figure 6A:
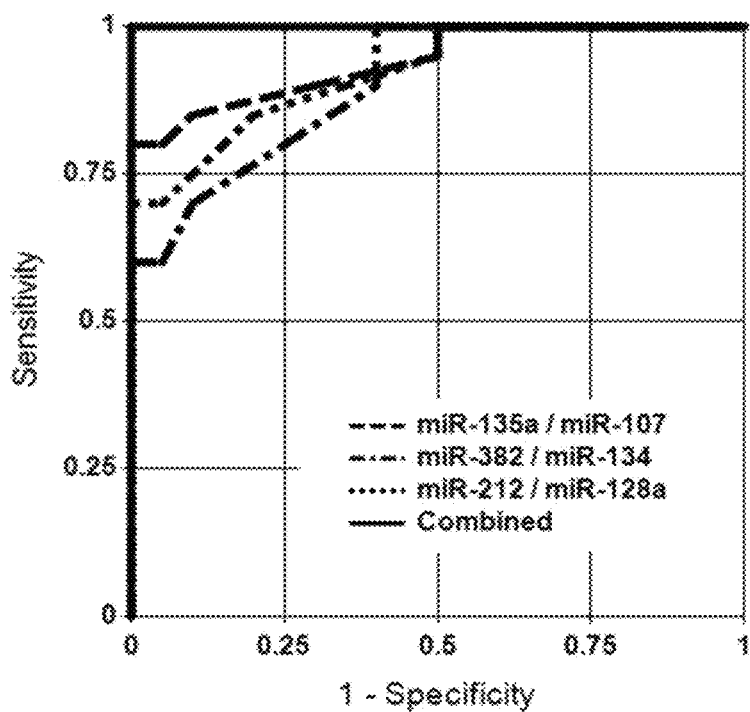
FIGS. 6A-6F present Receiver-Operating Characteristics (ROC) curve analysis of differentiation between various cohorts tested in Example 1.
Figure 6B:
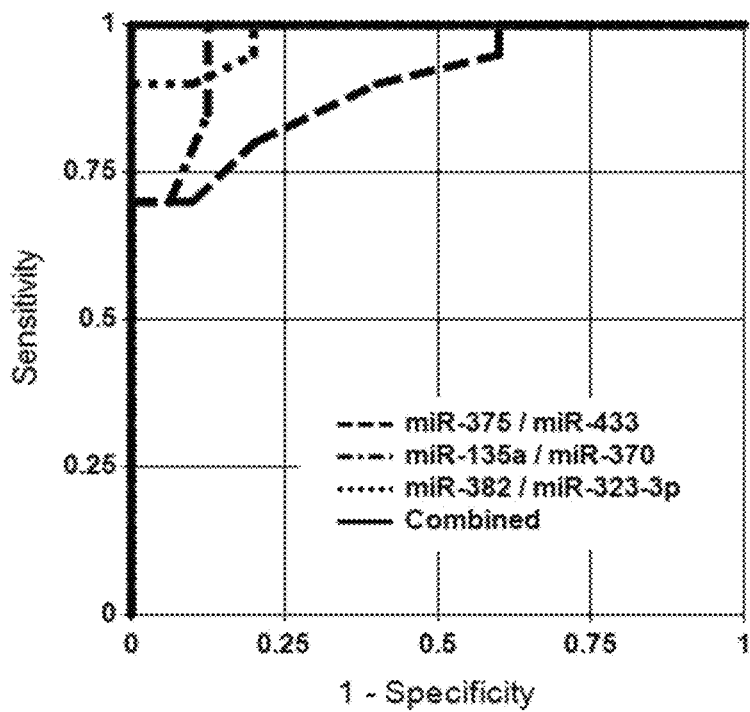
Figure 6C:
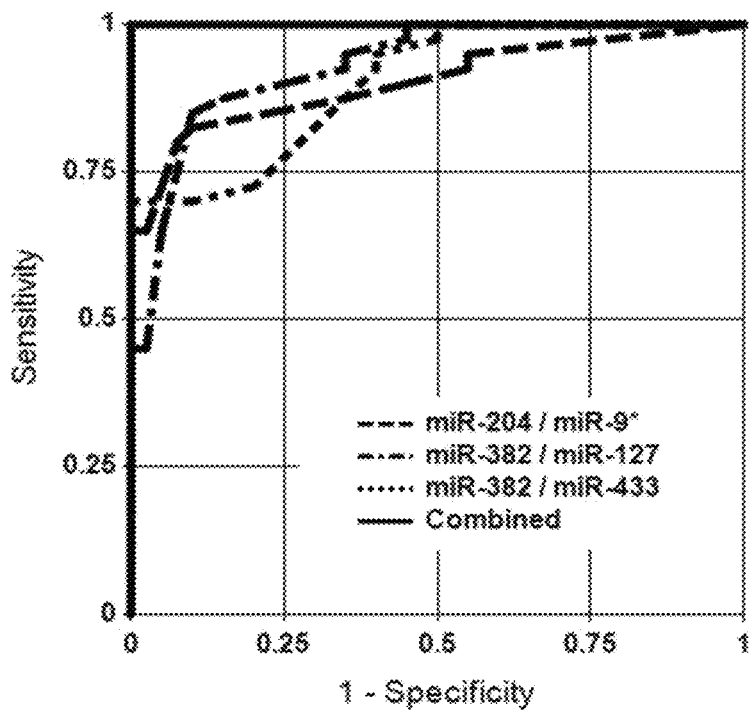
Figure 6D:
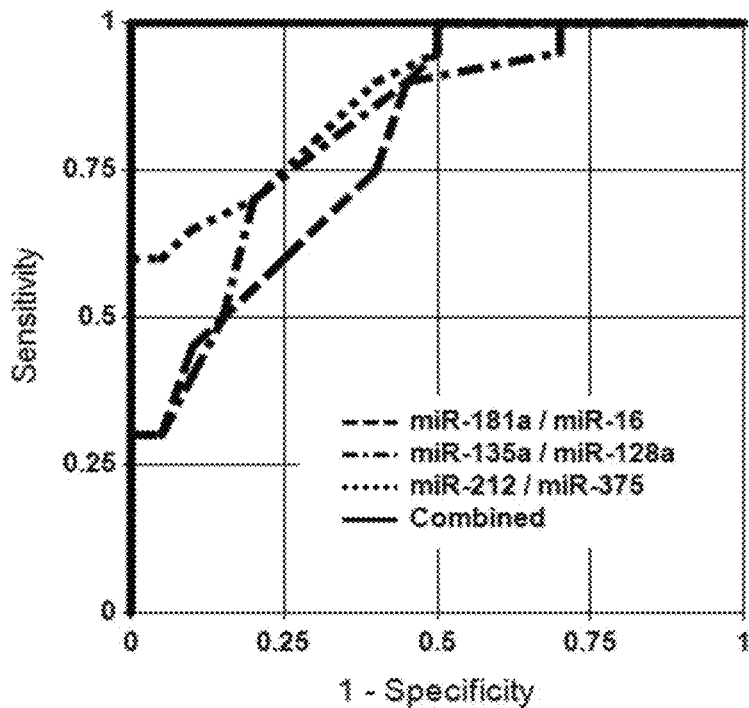
Figure 6E:
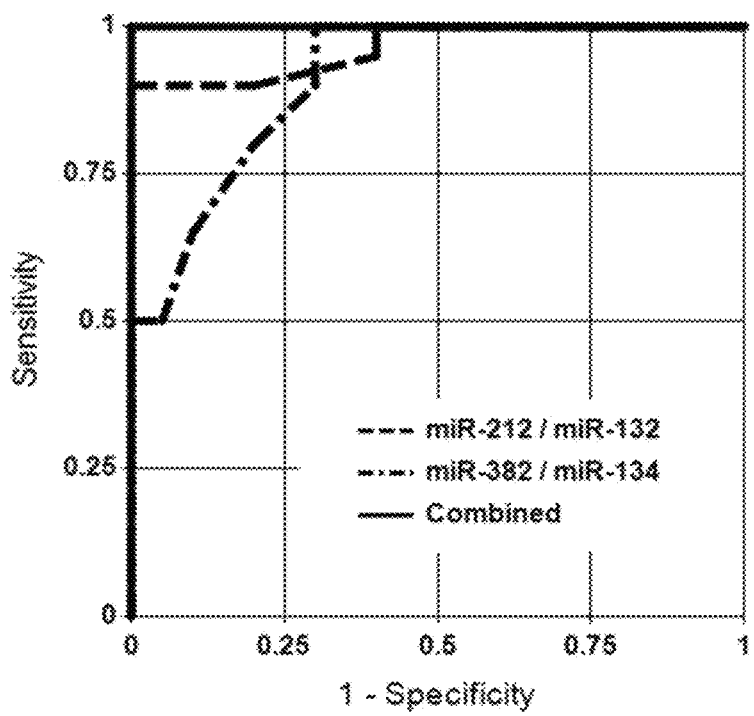
Figure 6F:
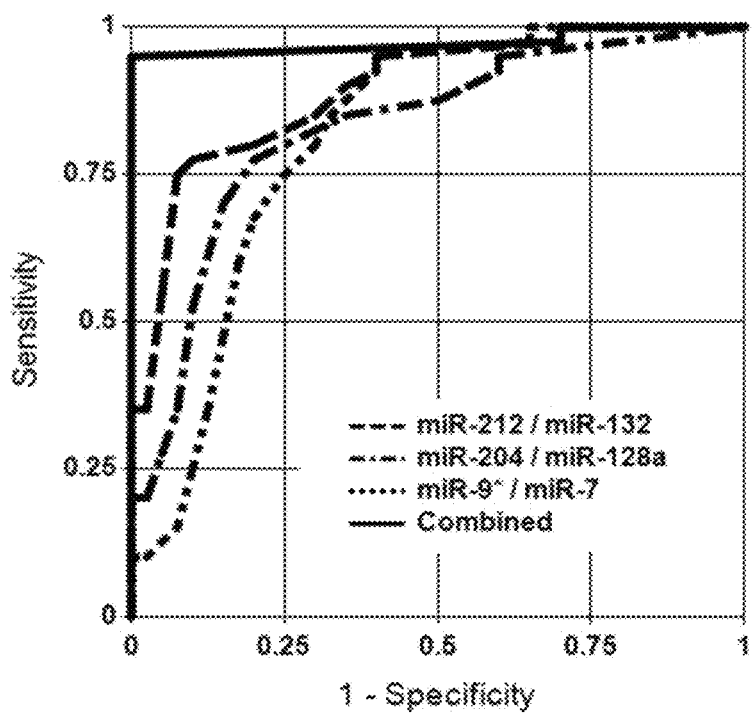

Table of the correlation data presented in FIGS. 5A-5B.

|  | Age | miR-127 | miR-134 | miR-323-3p | miR-370 | miR-382 | miR-411 | miR-433 | miR-487b |
|---|---|---|---|---|---|---|---|---|---|
| Male | 29.7 ± 2.79 | −0.03 | −0.19 | −0.17 | −0.37 | −0.10 | 0.12 | −0.19 | −0.09 |
|  | 41.4 ± 1.84 | 0.20 | 0.09 | 0.03 | −0.25 | 0.28 | 0.17 | 0.13 | 0.05 |
|  | 49.8 ± 3.22 | −0.69 | −0.72 | −0.40 | −0.63 | −0.50 | −0.61 | −0.60 | −0.58 |
|  | 60.4 ± 3.72 | −0.32 | −0.29 | −0.21 | −0.12 | −0.40 | −0.32 | −0.25 | −0.39 |
|  | 69.6 ± 2.67 | 0.59 | 0.62 | 0.54 | 0.48 | 0.50 | 0.29 | 0.46 | 0.52 |
| Female | 28.1 ± 1.1 | −0.34 | −0.51 | −0.38 | −0.43 | −0.45 | −0.05 | −0.27 | −0.42 |
|  | 42.4 ± 3.31 | 0.31 | 0.44 | 0.36 | 0.33 | 0.41 | 0.18 | 0.40 | 0.37 |
|  | 49.6 ± 2.37 | −0.06 | 0.07 | 0.16 | −0.44 | 0.01 | −0.30 | −0.04 | 0.01 |
|  | 59.6 ± 2.07 | 0.1 | −0.01 | 0.1 | −0.34 | 0.06 | 0.08 | 0.09 | 0.04 |
|  | 70.2 ± 2.82 | −0.37 | −0.28 | −0.36 | −0.31 | −0.13 | −0.55 | −0.35 | −0.44 |

TABLE 11

Standard Deviations presented as the ratio STD/Average for miRNA-134 family members. Cohorts with the highest StD/Average ratios are indicated in bold.

|  | Group | miR-127 | miR-134 | miR-323-3p | miR-370 | miR-382 | miR-411 | miR-433 | miR-487b | Aver |
|---|---|---|---|---|---|---|---|---|---|---|
| Male | 26-35 | 0.23 | 0.16 | 0.24 | 0.41 | 0.20 | 0.22 | 0.28 | 0.27 | 0.25 |
|  | 36-45 | 0.20 | 0.22 | 0.17 | 0.33 | 0.20 | 0.28 | 0.24 | 0.23 | 0.23 |
|  | 46-55 | 0.20 | 0.15 | 0.19 | 0.24 | 0.20 | 0.31 | 0.19 | 0.25 | 0.22 |
|  | 56-65 | 0.34 | 0.29 | 0.36 | 0.37 | 0.42 | 0.26 | 0.36 | 0.34 | 0.34 |
|  | 66-73 | 0.19 | 0.15 | 0.14 | 0.17 | 0.20 | 0.15 | 0.14 | 0.19 | 0.17 |
| Female | 26-35 | 0.23 | 0.20 | 0.20 | 0.20 | 0.16 | 0.24 | 0.24 | 0.23 | 0.21 |
|  | 36-45 | 0.21 | 0.20 | 0.14 | 0.15 | 0.30 | 0.23 | 0.17 | 0.22 | 0.20 |
|  | 46-55 | 0.45 | 0.31 | 0.42 | 0.48 | 0.37 | 0.61 | 0.41 | 0.37 | 0.43 |
|  | 56-65 | 0.38 | 0.45 | 0.42 | 0.48 | 0.43 | 0.28 | 0.36 | 0.44 | 0.41 |
|  | 66-73 | 0.28 | 0.30 | 0.25 | 0.37 | 0.32 | 0.27 | 0.31 | 0.32 | 0.30 |

Example 3. Correlation of miRNA Pairs with Age of Men and Women Cohorts

Figure 7:
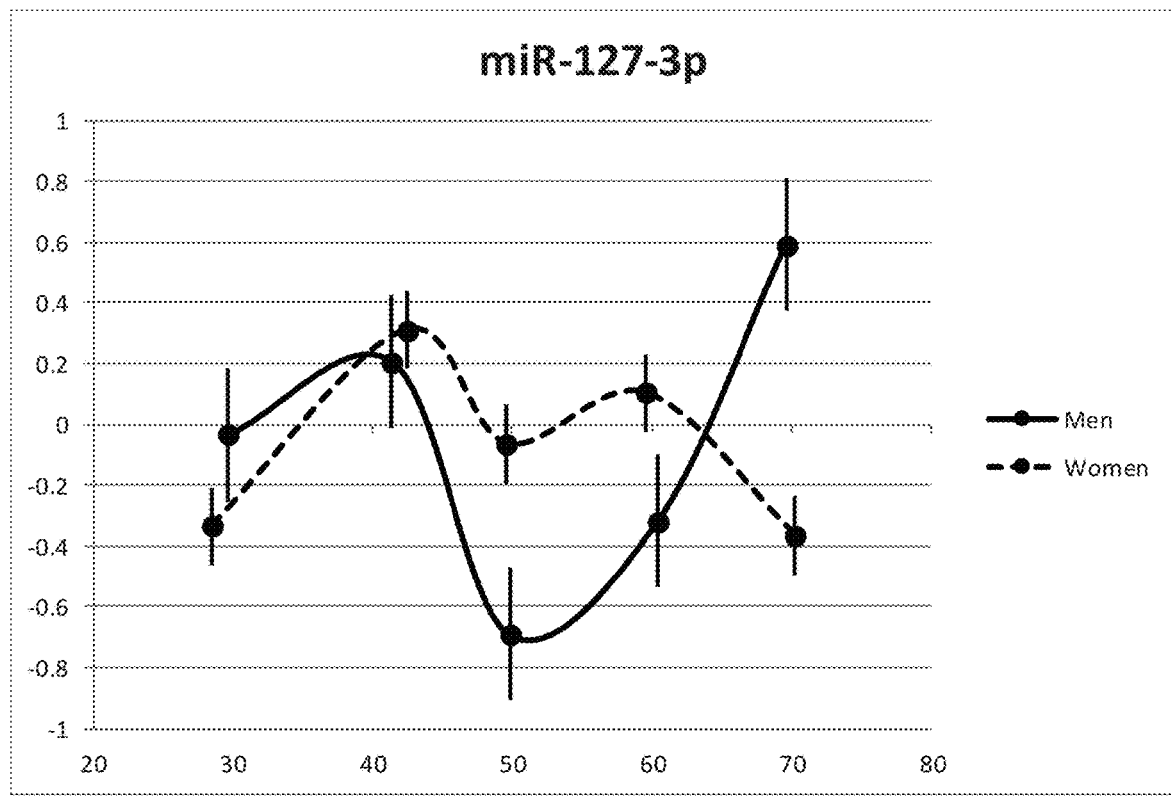
FIG. 7 shows a correlation of miRNA plasma concentrations with age in male and female participants tested in Example 1. Data are presented as average and standard deviation for each age cohort. X axis: age; Y axis: correlation of miRNA plasma concentrations with subject age in the various cohorts (r).
Figure 7:
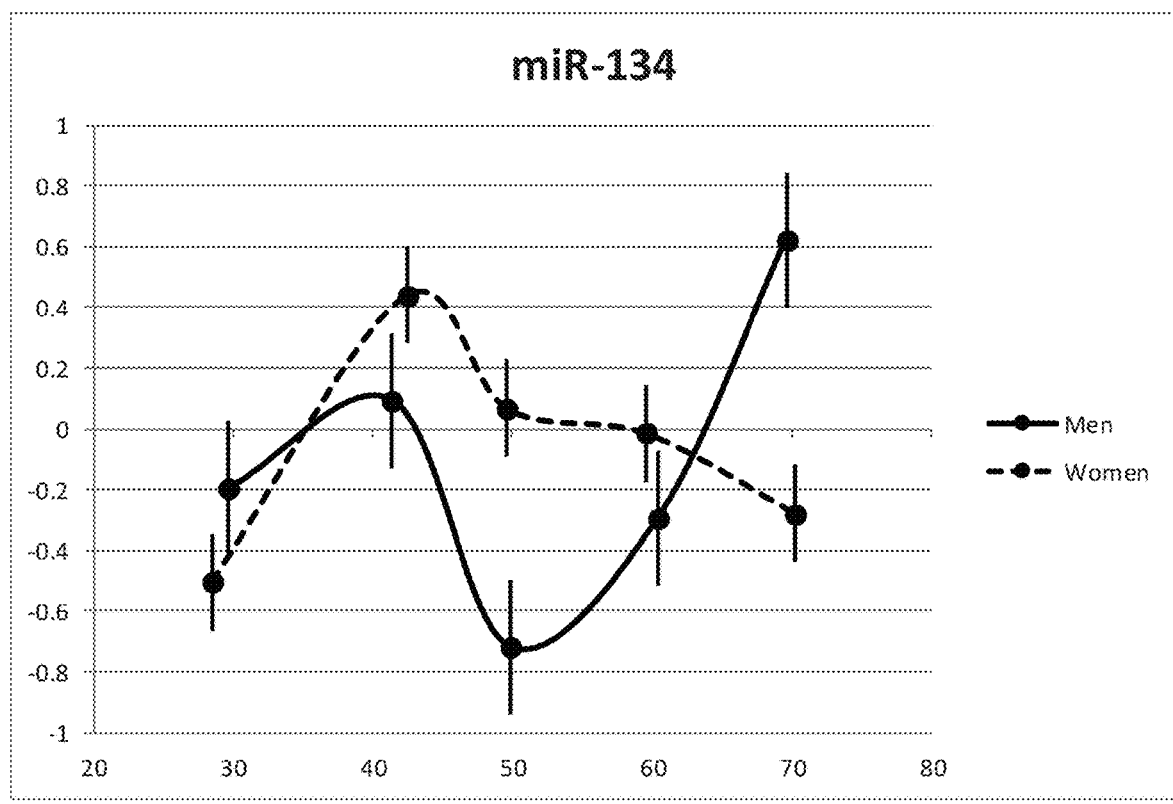
Figure 7:
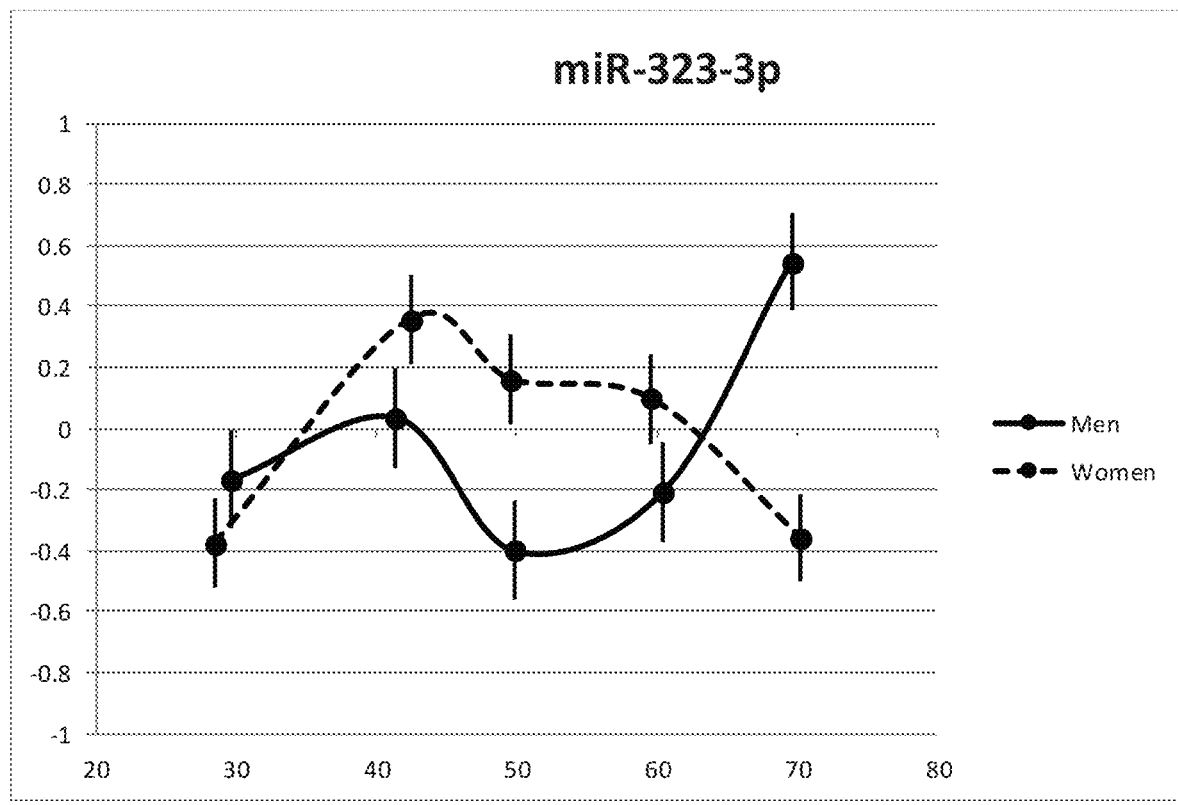
Figure 7:
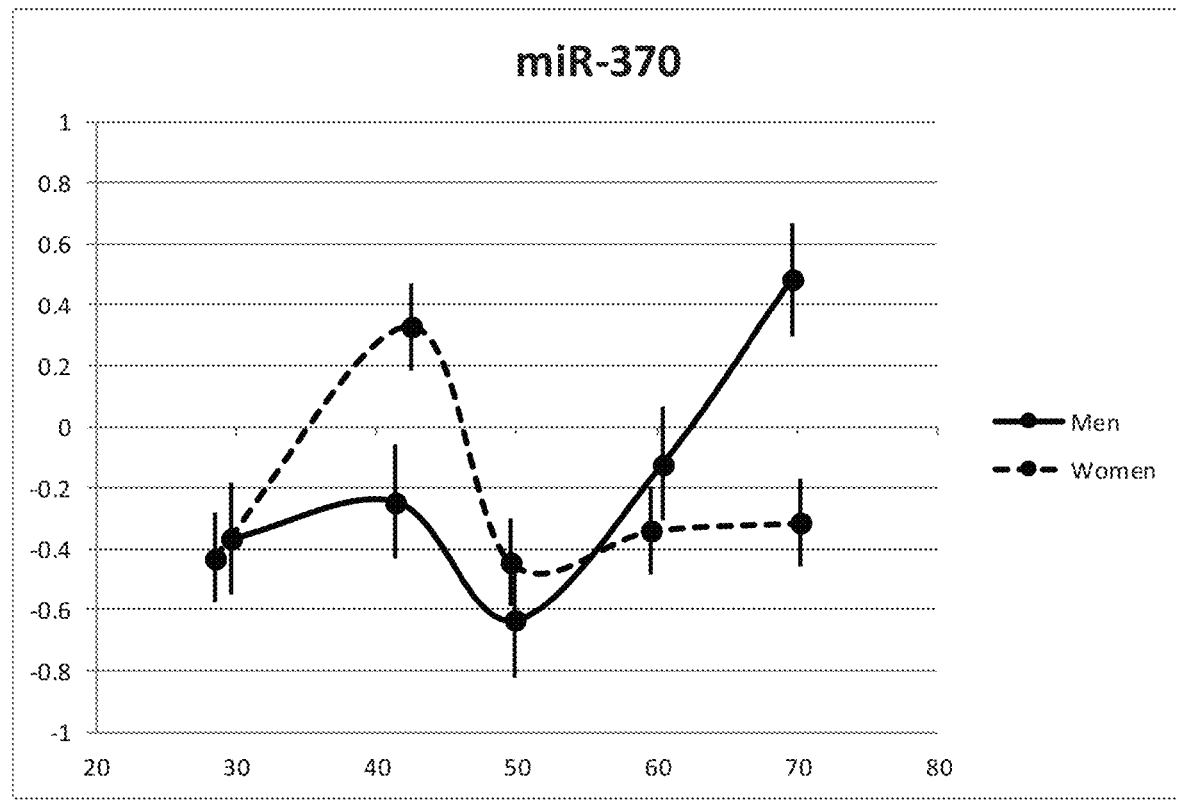
Figure 7:
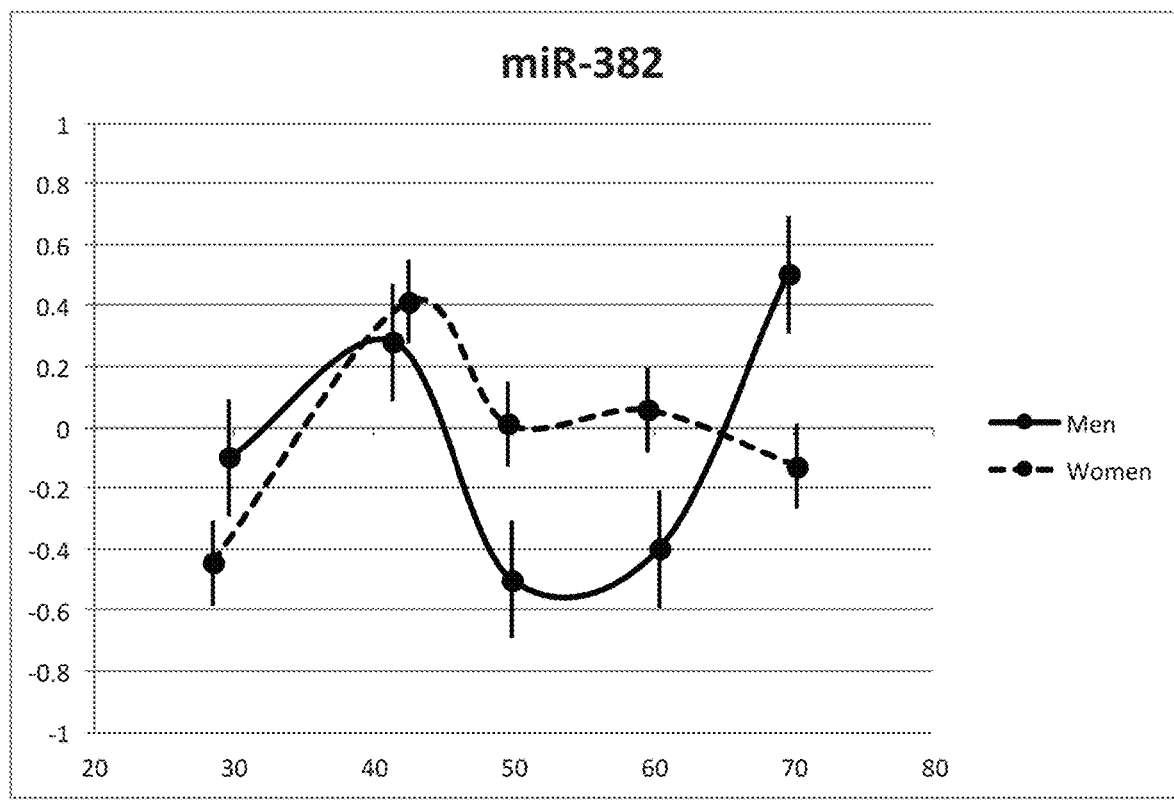
Figure 7:
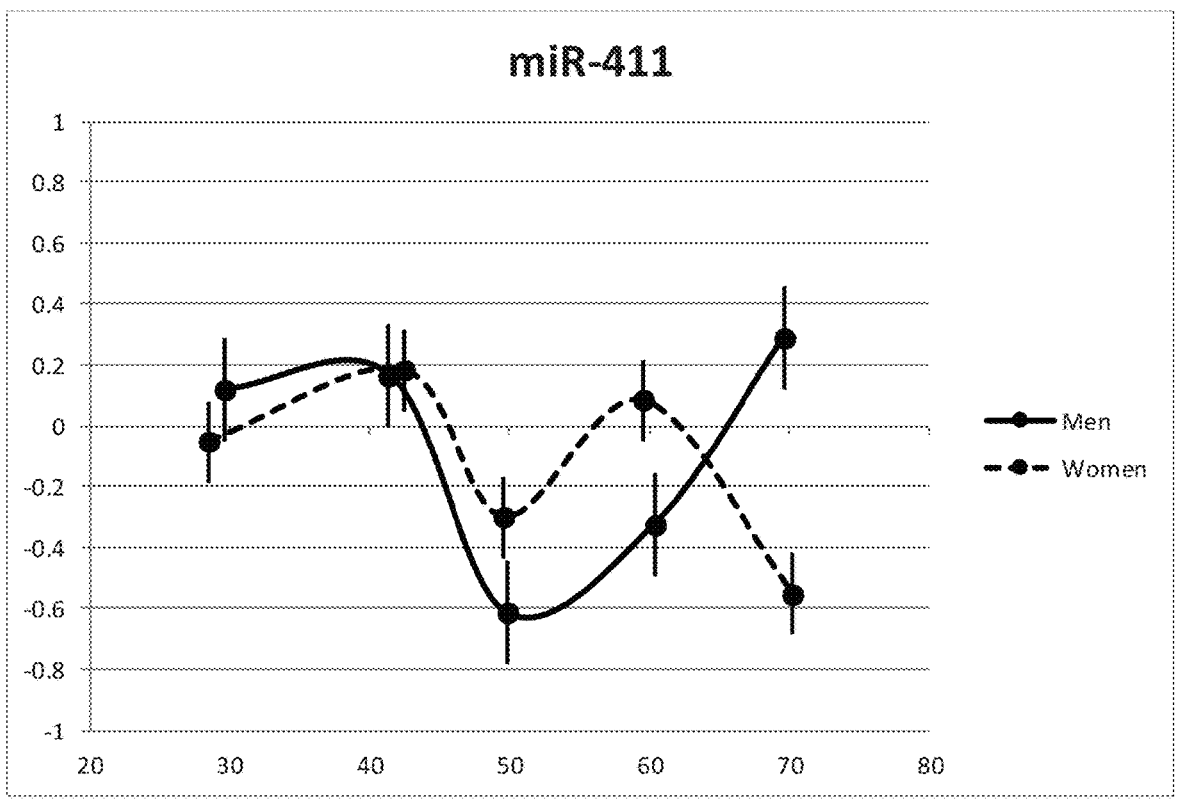
Figure 7:
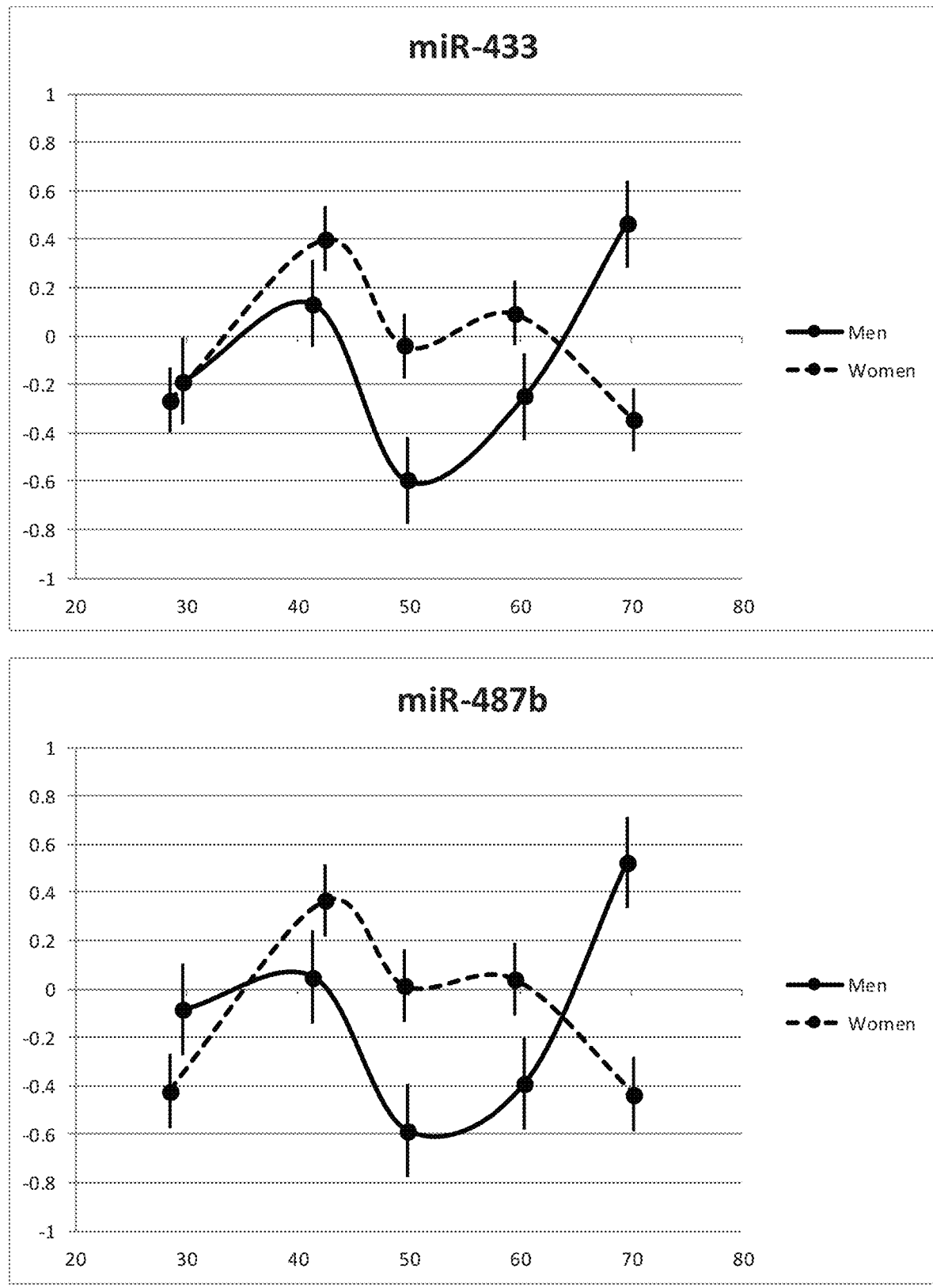
Figure 7:
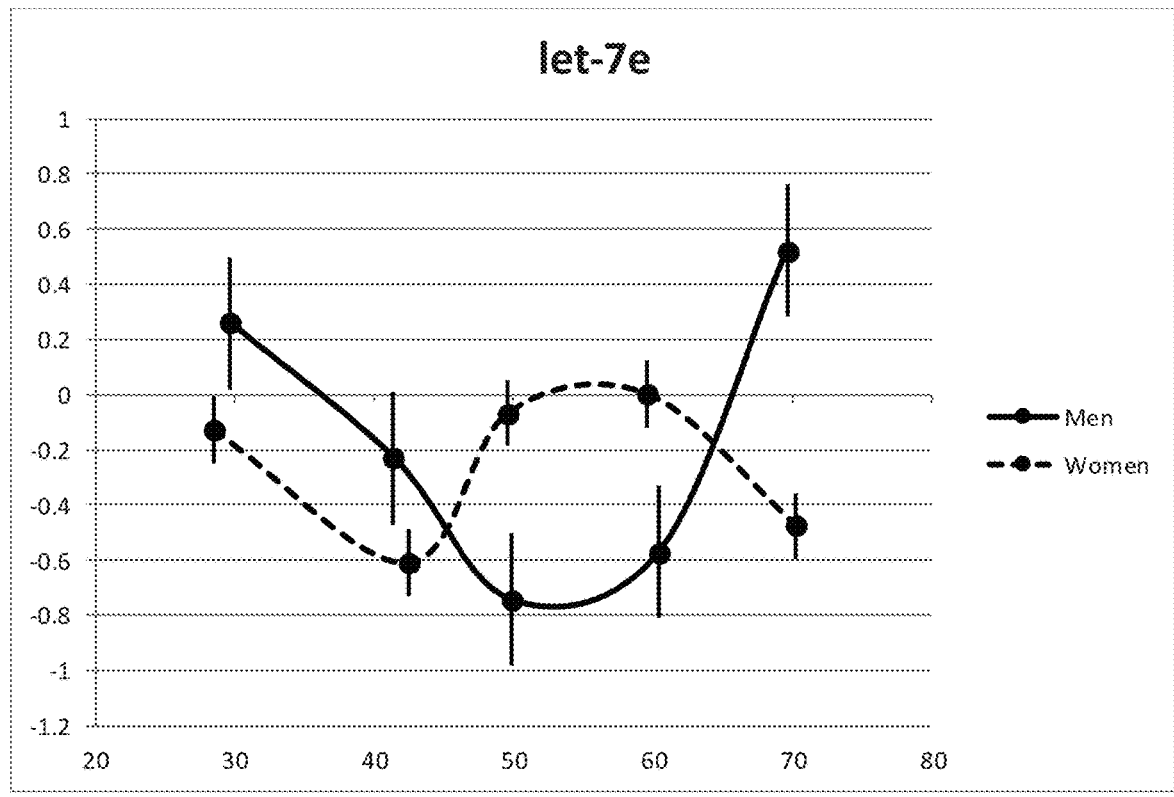
Figure 7:
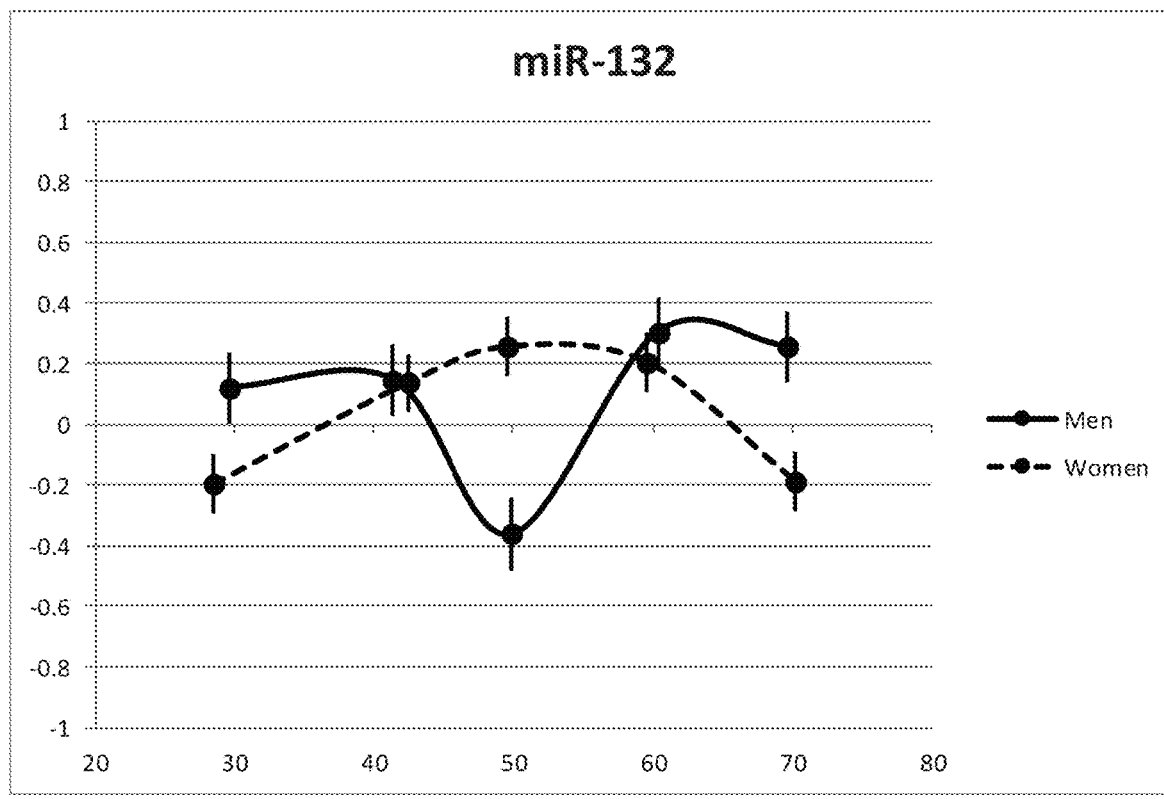
Figure 7:
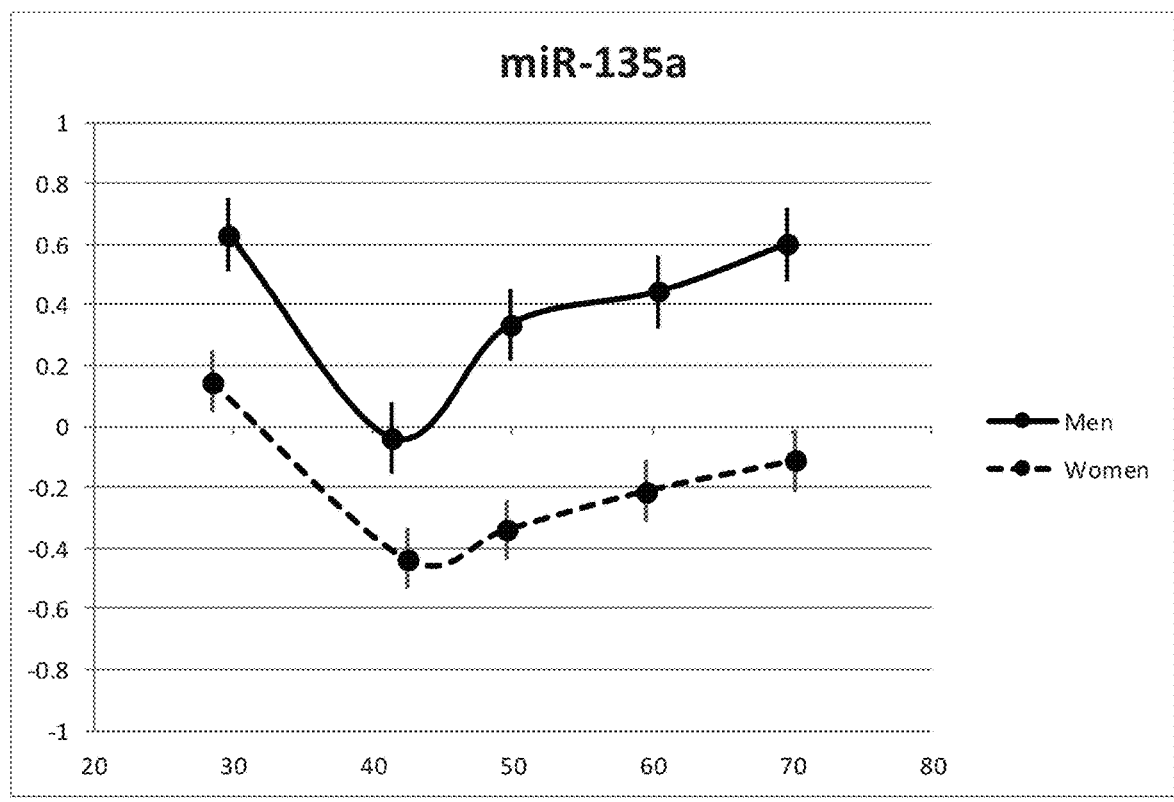
Figure 7:
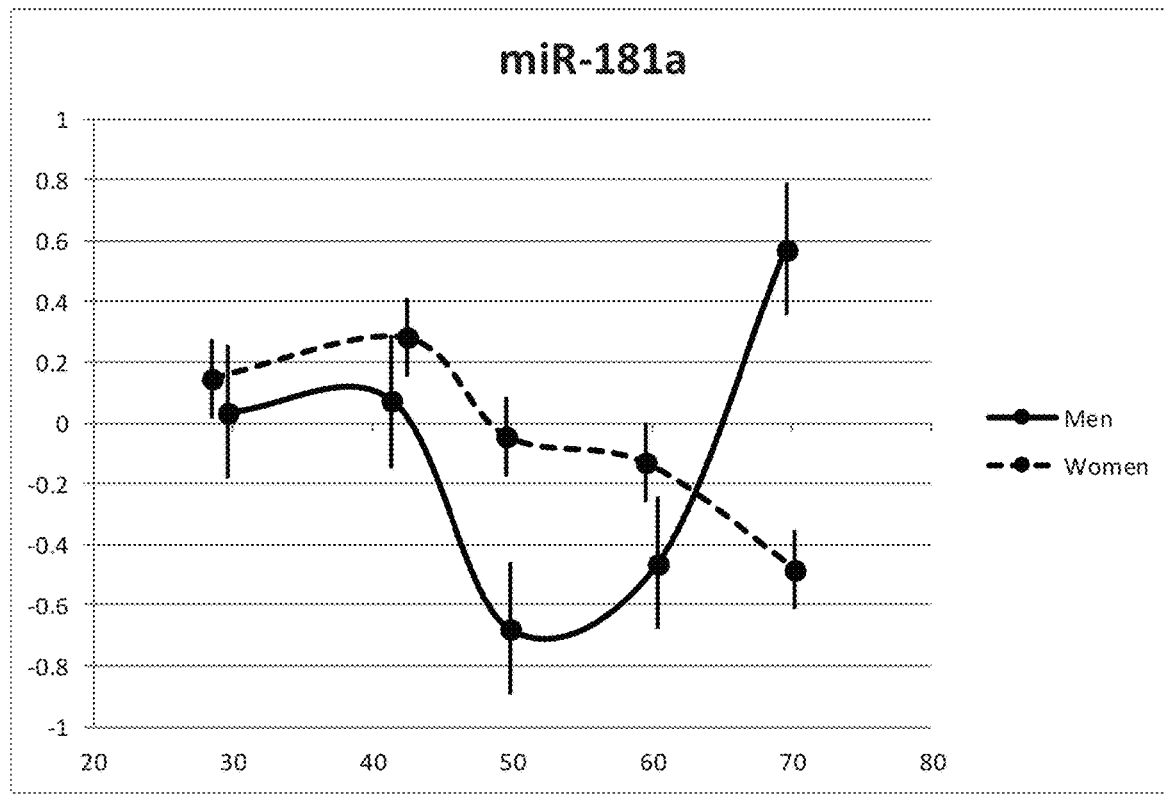
Figure 7:
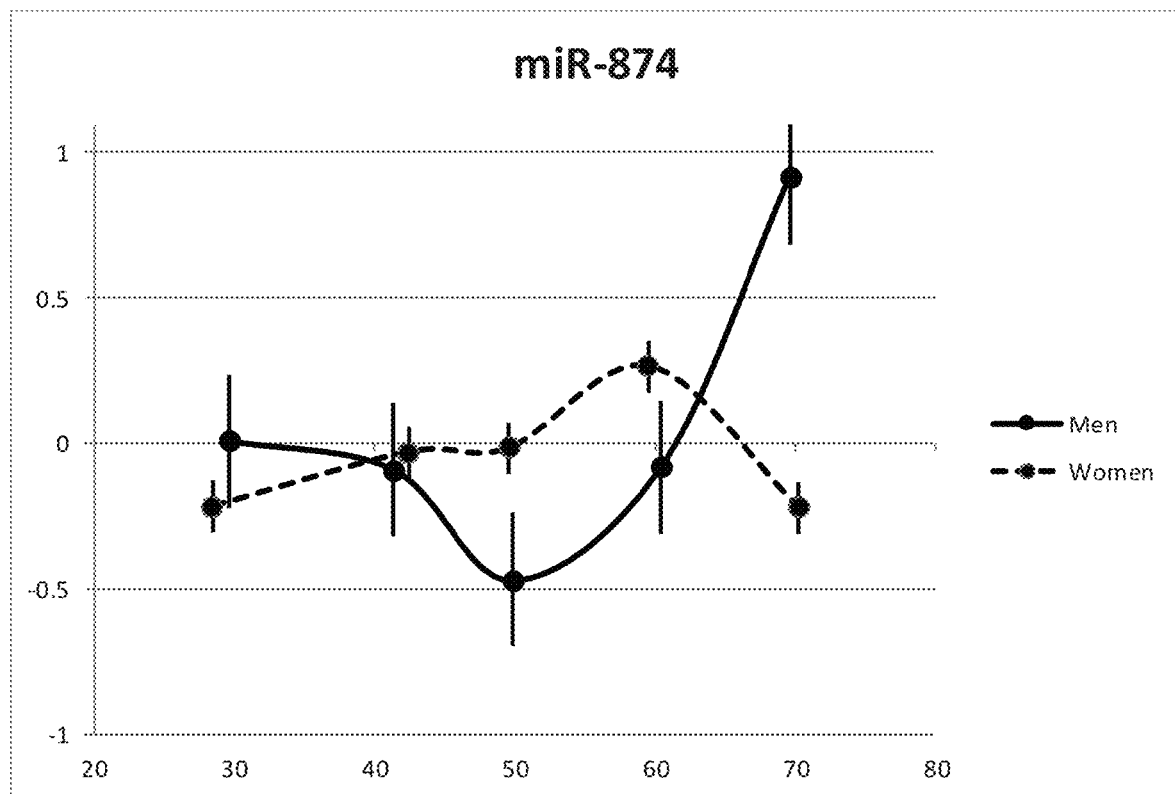
Figure 7:
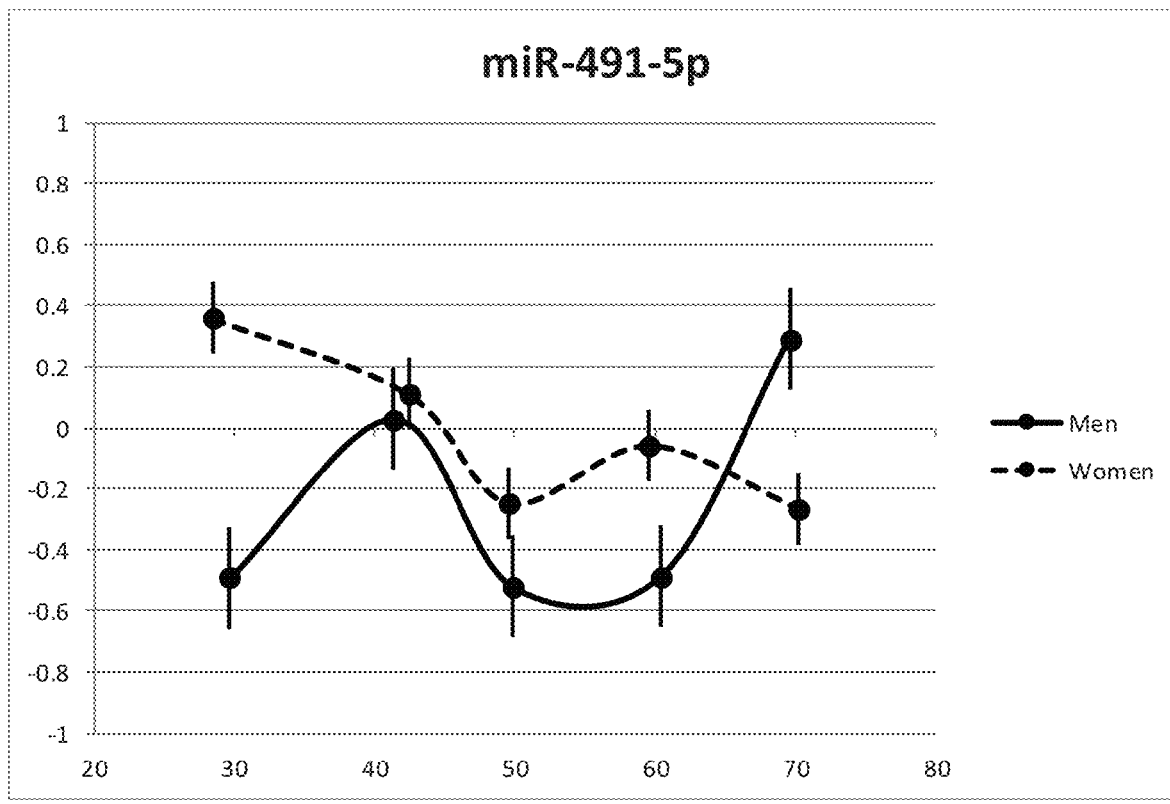
Figure 7:
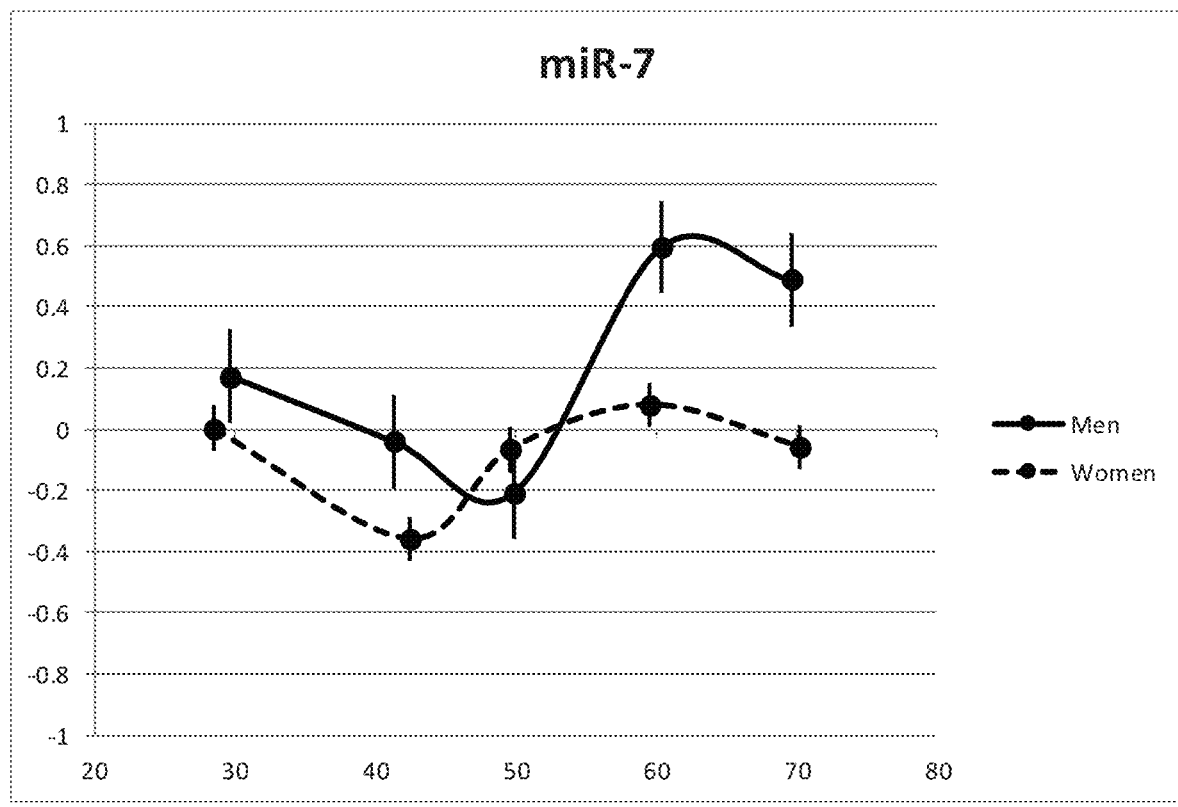
Figure 7:
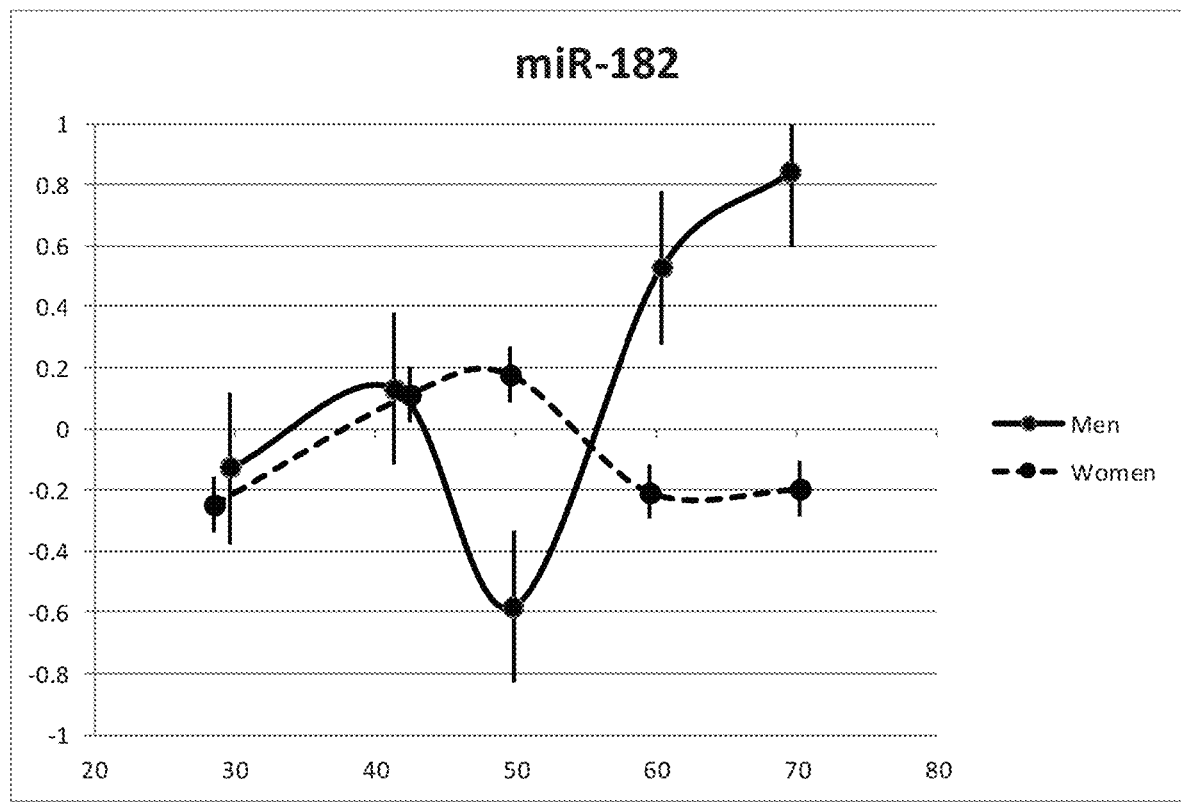
Figure 7:
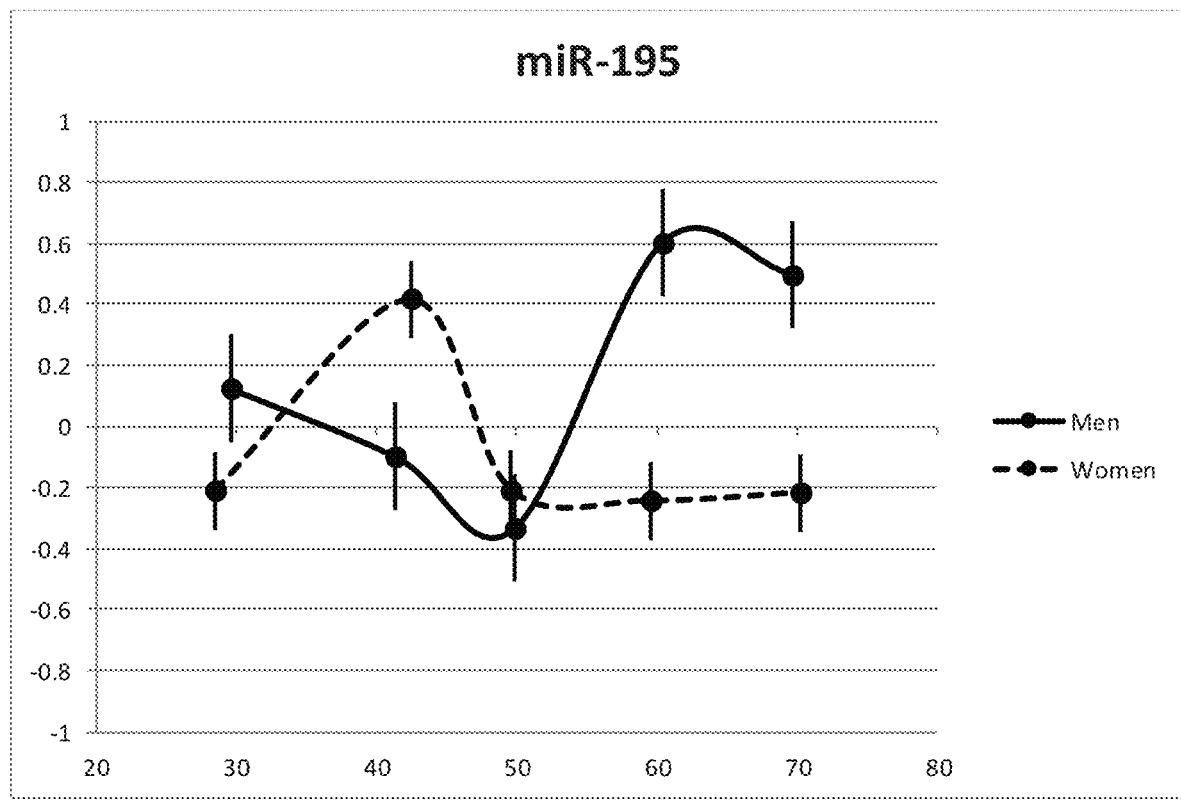
Figure 7:
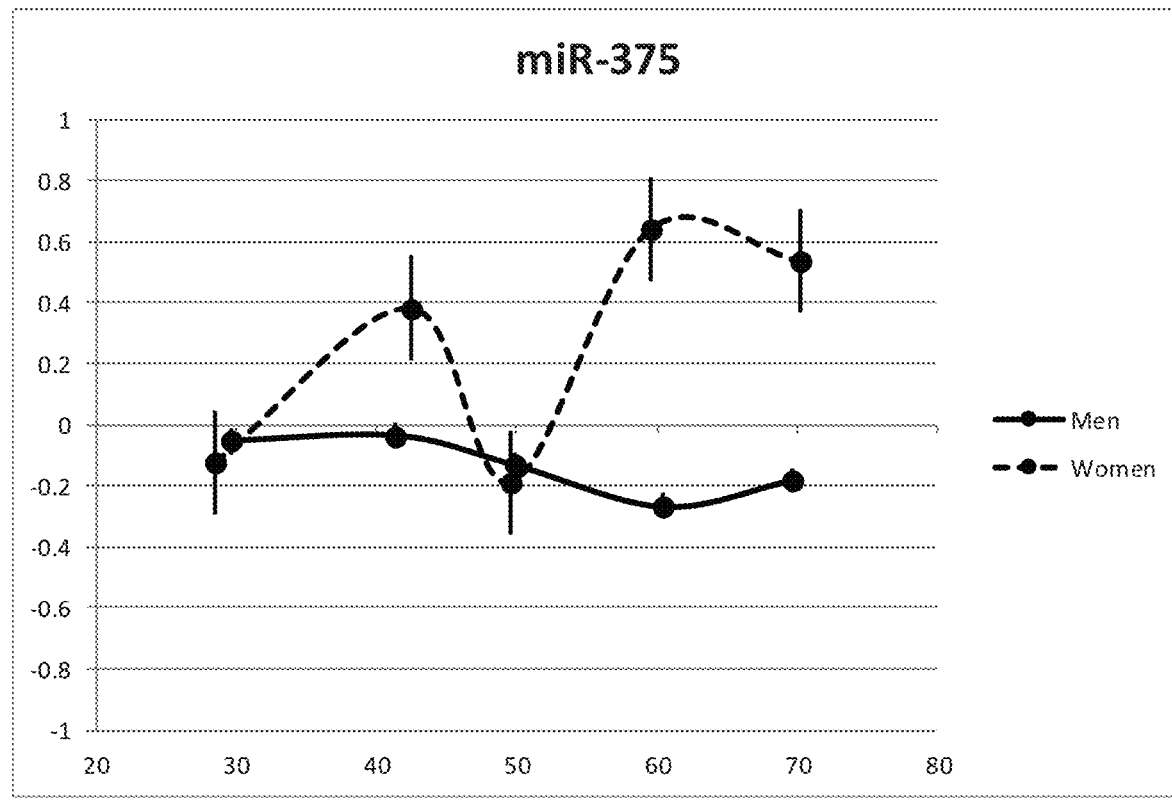
Figure 7:
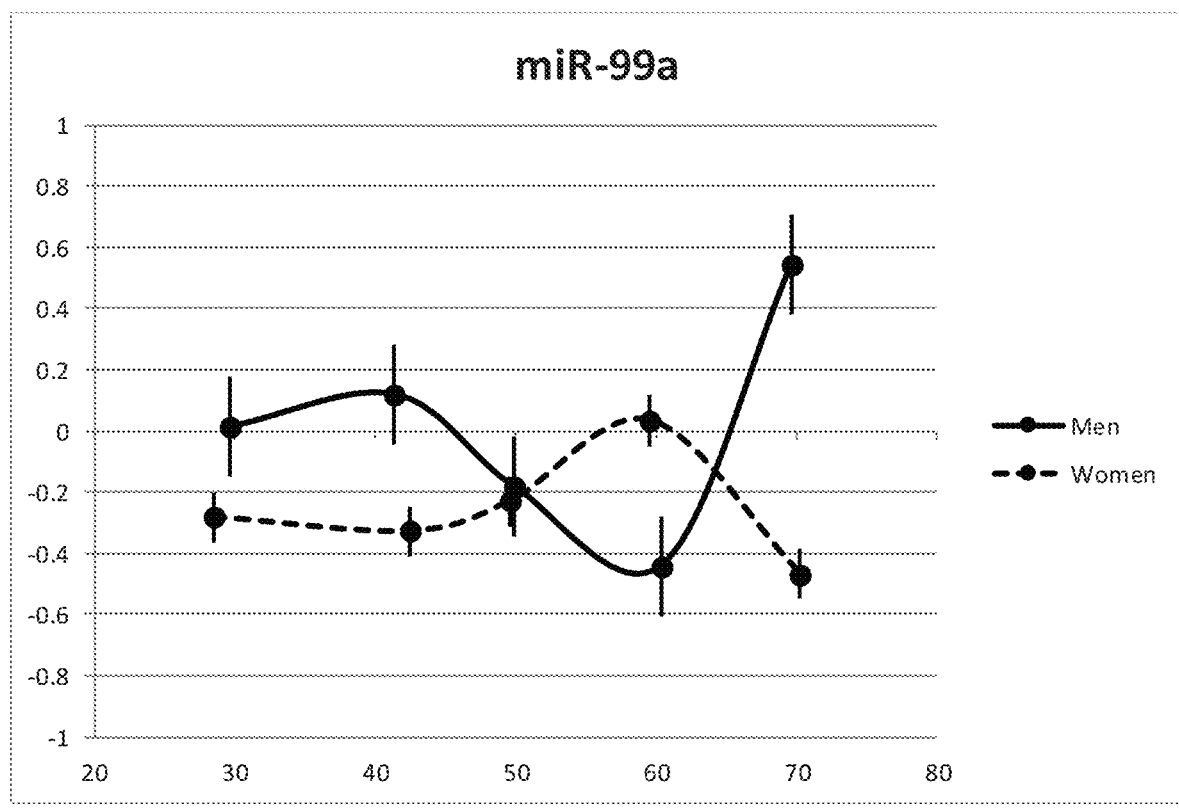
Figure 8:
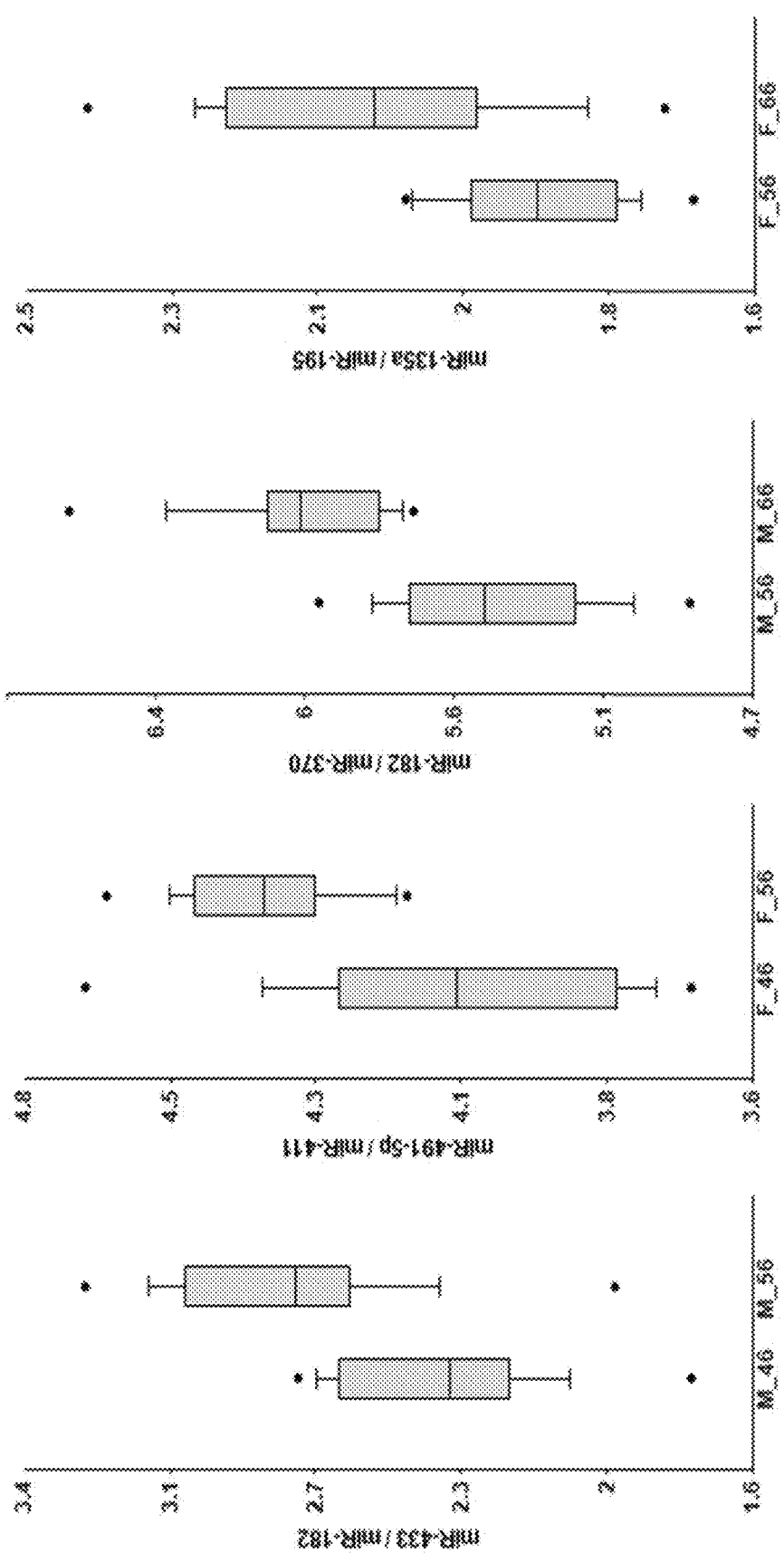
FIG. 8 shows differentiation of consecutively aged male or female cohorts from each other by select microRNA pairs. M: male cohorts; F: female cohorts. Numbers indicate the youngest age of each respective cohort (e.g. M_26 is the male 26-35-year-old cohort). For the box-and-whisker plots, the ratios were calculated as $2-\Delta Ct \times 100$, and the results are presented on a log 10 scale. The upper and lower limits of the boxes and the lines inside the boxes indicate the 75th and 25th percentiles and the average, respectively. The upper and lower horizontal bars denote the 90th and 10th percentiles, respectively. The points indicate assay values located outside 80% of the data.
Figure 8:
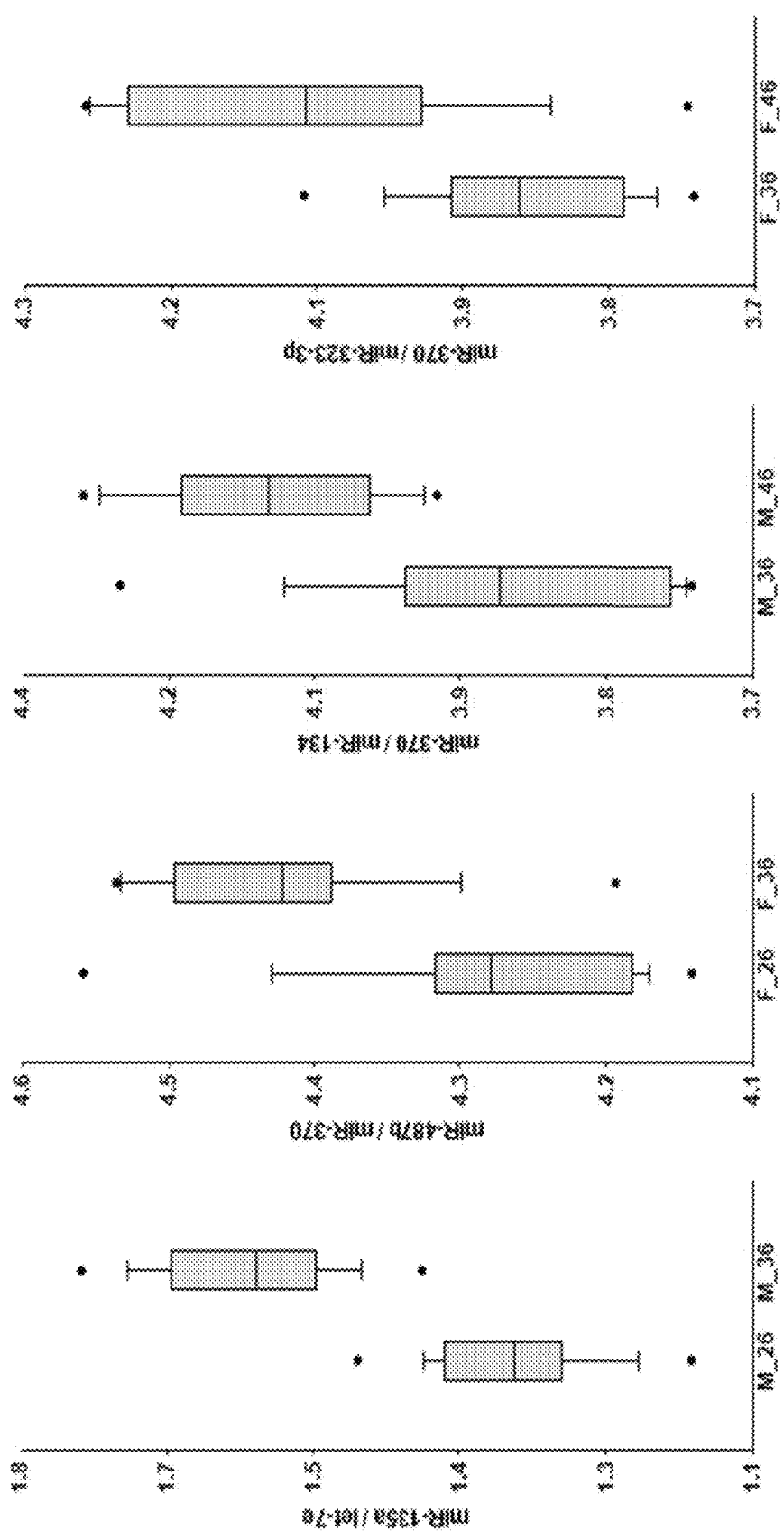

As mentioned above, biomarkers, which can be used for aging and its modification monitoring are highly needed for developing treatments capable of delaying normal aging and respectively preventing aging-associated diseases. Obviously, such biomarkers should correlate with the age at least in some periods of human life. FIG. 2-4 demonstrate that changes of miRNA concentrations in plasma are different in various period of male and female life. FIG. 7 provides correlation between individual miRNAs and subjects age, one again demonstrating the difference between male and females. Thus, first the present inventors tried to find biomarker miRNA pairs capable of differentiating consequent age groups in male and female cohorts. FIG. 8 and Tables 12 and 13 present such miRNA pairs for men and women, respectively. Since neighboring 10 years age group could be effectively separated by many miRNA pairs, the present inventors then checked if there are miRNA pairs correlating with age in each of these cohorts. FIGS. 9, 10 and Table 14 demonstrates that there are miRNA pairs which effectively correlate with the age in each of those groups and thus reflect aging processes in those periods.

TABLE 12 miRNA pairs differentiating consequent age groups in male cohorts

| Age Groups | miRNA pairs | Sens | Spec | Accuracy | AUC | P-value |
|---|---|---|---|---|---|---|
| 26-35 vs 36-45 | miR-135a/let-7e | 0.77 | 0.86 | 0.82 | 0.94 | 1.40E−03 |
|  | miR-135a/miR-487b | 0.86 | 0.76 | 0.81 | 0.90 | 4.60E−03 |
|  | miR-132/miR-411 | 0.67 | 0.9 | 0.79 | 0.89 | 1.00E−02 |
|  | miR-132/miR-127 | 0.76 | 0.76 | 0.76 | 0.83 | 1.90E−02 |
|  | miR-382/miR-487b | 0.76 | 0.76 | 0.76 | 0.87 | 1.60E−02 |
|  | miR-135a/miR-411 | 0.78 | 0.70 | 0.74 | 0.87 | 1.20E−02 |
|  | miR-135a/miR-127 | 0.82 | 0.64 | 0.73 | 0.86 | 8.60E−03 |
|  | miR-132/miR-487b | 0.77 | 0.68 | 0.73 | 0.82 | 1.90E−02 |
|  | miR-134/miR-127 | 0.77 | 0.68 | 0.73 | 0.83 | 2.30E−02 |
|  | miR-135a/miR-134 | 0.72 | 0.72 | 0.72 | 0.86 | 1.60E−02 |
|  | miR-135a/miR-181a | 0.80 | 0.60 | 0.70 | 0.84 | 1.90E−02 |
|  | miR-99a/miR-487b | 0.58 | 0.78 | 0.68 | 0.81 | 2.70E−02 |
|  | miR-99a/miR-127 | 0.58 | 0.77 | 0.68 | 0.81 | 2.70E−02 |
|  | miR-135a/miR-382 | 0.67 | 0.67 | 0.67 | 0.82 | 1.90E−02 |
|  | miR-135a/miR-7 | 0.77 | 0.58 | 0.67 | 0.82 | 4.40E−02 |
|  | miR-134/miR-487b | 0.57 | 0.76 | 0.66 | 0.80 | 2.70E−02 |
|  | miR-135a/miR-370 | 0.88 | 0.44 | 0.65 | 0.81 | 3.80E−02 |

TABLE 12-continued miRNA pairs differentiating consequent age groups in male cohorts

| Age Groups | miRNA pairs | Sens | Spec | Accuracy | AUC | P-value |
|---|---|---|---|---|---|---|
| | miR-491-5p/miR-411 | 0.74 | 0.57 | 0.65 | 0.80 | 4.70E−02 |
| | miR-874/miR-487b | 0.60 | 0.70 | 0.65 | 0.81 | 4.40E−02 |
| | miR-135a/miR-433 | 0.67 | 0.60 | 0.63 | 0.80 | 4.00E−02 |
| | miR-135a/let-7e + miR-132/miR-411 | 0.90 | 0.80 | 0.85 | 0.95 | 8.50E−04 |
| 36-45 vs 46-55 | miR-370/miR-134 | 0.78 | 0.78 | 0.78 | 0.91 | 6.60E−03 |
| | miR-127/miR-135a | 0.77 | 0.67 | 0.72 | 0.83 | 2.30E−02 |
| | miR-127/miR-134 | 0.66 | 0.76 | 0.71 | 0.80 | 2.70E−02 |
| | miR-134/miR-135a | 0.62 | 0.73 | 0.68 | 0.83 | 4.40E−02 |
| | miR-323-3p/miR-135a | 0.80 | 0.50 | 0.65 | 0.82 | 3.20E−02 |
| | miR-7/miR-135a | 0.63 | 0.63 | 0.63 | 0.78 | 1.10E−02 |
| | miR-487b/miR-134 | 0.66 | 0.56 | 0.61 | 0.78 | 8.10E−02 |
| | miR-7/miR-135a + miR-127/miR-134 + miR-487b/ miR-134 | 0.90 | 0.80 | 0.85 | 0.92 | 3.60E−03 |
| 46-55 vs 56-65 | miR-433/miR-182 | 0.88 | 0.70 | 0.78 | 0.84 | 1.80E−02 |
| | miR-433/miR-411 | 0.75 | 0.80 | 0.78 | 0.91 | 4.30E−03 |
| | miR-433/miR-132 | 0.78 | 0.73 | 0.75 | 0.81 | 5.00E−02 |
| | miR-382/miR-411 | 0.72 | 0.76 | 0.74 | 0.86 | 1.50E−02 |
| | miR-433/miR-195 | 0.63 | 0.80 | 0.72 | 0.86 | 3.40E−02 |
| | miR-491-5p/-181a | 0.70 | 0.70 | 0.70 | 0.81 | 3.20E−02 |
| | miR-135a/miR-182 | 0.59 | 0.79 | 0.69 | 0.84 | 1.60E−02 |
| | miR-491-5p/let-7e | 0.74 | 0.63 | 0.69 | 0.81 | 3.20E−02 |
| | miR-433/miR-181a | 0.71 | 0.66 | 0.68 | 0.83 | 2.80E−02 |
| | miR-135a/miR-181a | 0.62 | 0.73 | 0.68 | 0.82 | 2.70E−02 |
| | miR-370/miR-182 | 0.48 | 0.83 | 0.67 | 0.85 | 2.80E−02 |
| | miR-487b/miR-411 | 0.59 | 0.73 | 0.67 | 0.89 | 2.30E−02 |
| | miR-135a/miR-7 | 0.49 | 0.78 | 0.64 | 0.81 | 2.70E−02 |
| | miR-433/miR-370 | 0.47 | 0.68 | 0.58 | 0.80 | 4.60E−02 |
| | miR-433/miR-411 + miR-433/miR-370 + miR-370/miR-182 | 0.88 | 0.90 | 0.89 | 0.96 | 6.60E−04 |
| 56-65 vs 66-75 | miR-182/miR-370 | 0.69 | 0.83 | 0.76 | 0.93 | 7.50E−03 |
| | miR-134/miR-382 | 0.80 | 0.67 | 0.74 | 0.84 | 1.50E−02 |
| | miR-7/miR-370 | 0.71 | 0.71 | 0.71 | 0.87 | 2.00E−02 |
| | miR-195/miR-370 | 0.78 | 0.65 | 0.71 | 0.87 | 2.00E−02 |
| | miR-411/miR-382 | 0.67 | 0.75 | 0.71 | 0.84 | 2.40E−02 |
| | miR-182/miR-433 | 0.58 | 0.85 | 0.70 | 0.90 | 7.10E−03 |
| | miR-195/miR-433 | 0.63 | 0.79 | 0.70 | 0.84 | 3.40E−02 |
| | miR-874/miR-433 | 0.84 | 0.53 | 0.70 | 0.84 | 2.80E−02 |
| | miR-181a/miR-370 | 0.63 | 0.76 | 0.69 | 0.88 | 2.70E−02 |
| | miR-874/miR-370 | 0.77 | 0.62 | 0.69 | 0.82 | 4.80E−02 |
| | miR-132/miR-433 | 0.56 | 0.82 | 0.68 | 0.86 | 1.50E−02 |
| | miR-127/miR-370 | 0.60 | 0.75 | 0.68 | 0.82 | 4.80E−02 |
| | miR-181a/miR-433 | 0.60 | 0.75 | 0.67 | 0.83 | 2.80E−02 |
| | miR-7/miR-433 | 0.60 | 0.75 | 0.67 | 0.83 | 2.30E−02 |
| | miR-134/miR-370 | 0.60 | 0.74 | 0.67 | 0.85 | 3.70E−02 |
| | miR-99a/miR-382 | 0.66 | 0.66 | 0.66 | 0.83 | 1.90E−02 |
| | miR-181a/miR-874 | 0.66 | 0.66 | 0.66 | 0.80 | 3.80E−02 |
| | miR-182/miR-411 | 0.52 | 0.82 | 0.66 | 0.86 | 1.90E−02 |
| | miR-127/miR-382 | 0.51 | 0.81 | 0.66 | 0.85 | 1.10E−02 |
| | miR-181a/let-7e | 0.70 | 0.60 | 0.65 | 0.81 | 3.20E−02 |
| | miR-132/miR-370 | 0.57 | 0.71 | 0.64 | 0.87 | 2.70E−02 |
| | miR-182/miR-433 + miR-127/miR-382 + miR-134/miR-370 | 0.90 | 1.00 | 0.95 | 0.98 | 2.20E−04 |

TABLE 13 miRNA pairs differentiating consequent age groups in female cohorts

| Age Groups | miRNA pairs | Sens | Spec | Accuracy | AUC | P-value |
|---|---|---|---|---|---|---|
| 26-35 vs 36-45 | miR-182/miR-375 | 0.76 | 0.76 | 0.76 | 0.83 | 2.30E−02 |
| | miR-487b/miR-370 | 0.80 | 0.73 | 0.76 | 0.87 | 2.20E−02 |
| | miR-134/miR-370 | 0.68 | 0.76 | 0.73 | 0.83 | 2.90E−02 |
| | miR-132/miR-375 | 0.67 | 0.77 | 0.72 | 0.83 | 2.30E−02 |
| | miR-874/miR-375 | 0.72 | 0.72 | 0.72 | 0.85 | 2.30E−02 |
| | miR-99a/miR-375 | 0.67 | 0.75 | 0.71 | 0.92 | 4.60E−03 |
| | let-7e/miR-375 | 0.71 | 0.71 | 0.71 | 0.85 | 2.30E−02 |
| | miR-134/miR-127 | 0.70 | 0.70 | 0.70 | 0.81 | 2.70E−02 |
| | miR-433/miR-370 | 0.52 | 0.80 | 0.69 | 0.87 | 2.00E−02 |
| | miR-182/miR-382 | 0.54 | 0.78 | 0.67 | 0.82 | 3.30E−02 |

TABLE 13-continued miRNA pairs differentiating consequent age groups in female cohorts

| Age Groups | miRNA pairs | Sens | Spec | Accuracy | AUC | P-value |
|---|---|---|---|---|---|---|
| | miR-874/miR-7 | 0.54 | 0.64 | 0.59 | 0.80 | 2.30E−02 |
| | miR-135a/miR-7 | 0.42 | 0.74 | 0.58 | 0.80 | 3.80E−02 |
| | let-7e/miR-375 + miR-134/miR-127 + miR-487b/miR-370 | 0.90 | 0.80 | 0.85 | 0.96 | 6.60E−04 |
| 36-45 vs 46-55 | miR-370/miR-323-3p | 0.68 | 0.82 | 0.75 | 0.87 | 2.00E−02 |
| | miR-491-5p/miR-182 | 0.73 | 0.73 | 0.73 | 0.86 | 8.60E−03 |
| | miR-375/miR-99a | 0.83 | 0.62 | 0.73 | 0.82 | 3.20E−02 |
| | miR-411/miR-182 | 0.80 | 0.63 | 0.72 | 0.86 | 9.10E−03 |
| | miR-370/miR-382 | 0.66 | 0.77 | 0.71 | 0.89 | 1.90E−02 |
| | miR-370/miR-134 | 0.71 | 0.71 | 0.71 | 0.87 | 2.00E−02 |
| | miR-370/miR-127 | 0.71 | 0.71 | 0.71 | 0.92 | 1.50E−02 |
| | miR-135a/miR-182 | 0.71 | 0.71 | 0.71 | 0.83 | 2.30E−02 |
| | miR-491-5p/miR-874 | 0.81 | 0.61 | 0.71 | 0.86 | 1.60E−02 |
| | miR-375/miR-182 | 0.66 | 0.76 | 0.71 | 0.83 | 1.60E−02 |
| | miR-370/miR-487b | 0.64 | 0.77 | 0.70 | 0.85 | 3.70E−02 |
| | miR-132/miR-874 | 0.54 | 0.86 | 0.70 | 0.87 | 7.00E−03 |
| | miR-370/miR-182 | 0.62 | 0.77 | 0.69 | 0.83 | 3.70E−02 |
| | miR-127/miR-182 | 0.68 | 0.68 | 0.68 | 0.81 | 2.30E−02 |
| | miR-135a/miR-874 | 0.53 | 0.84 | 0.68 | 0.85 | 1.10E−02 |
| | miR-195/miR-182 | 0.67 | 0.67 | 0.67 | 0.83 | 1.90E−02 |
| | miR-370/miR-874 | 0.66 | 0.66 | 0.66 | 0.84 | 4.80E−02 |
| | miR-433/miR-182 | 0.57 | 0.76 | 0.66 | 0.82 | 4.00E−02 |
| | miR-411/miR-134 | 0.86 | 0.40 | 0.65 | 0.81 | 3.40E−02 |
| | miR-375/miR-874 | 0.50 | 0.80 | 0.65 | 0.86 | 1.30E−02 |
| | miR-411/miR-182 + miR-135a/miR-874 + miR-375/miR-99a | 0.90 | 0.90 | 0.90 | 0.99 | 1.60E−04 |
| 46-55 vs 56-65 | miR-491-5p/miR-411 | 0.73 | 0.73 | 0.73 | 0.82 | 3.20E−02 |
| | miR-195/miR-135a | 0.80 | 0.60 | 0.70 | 0.86 | 8.60E−03 |
| | miR-195/miR-99a | 0.74 | 0.63 | 0.69 | 0.86 | 8.60E−03 |
| | miR-182/miR-135a | 0.63 | 0.74 | 0.69 | 0.83 | 1.90E−02 |
| | miR-323-3p/miR-411 | 0.74 | 0.63 | 0.68 | 0.82 | 1.90E−02 |
| | miR-382/miR-411 | 0.74 | 0.63 | 0.68 | 0.82 | 2.70E−02 |
| | miR-132/miR-135a | 0.67 | 0.67 | 0.67 | 0.87 | 2.30E−02 |
| | miR-132/let-7e | 0.66 | 0.66 | 0.66 | 0.81 | 4.40E−02 |
| | miR-195/miR-411 | 0.80 | 0.50 | 0.65 | 0.83 | 2.30E−02 |
| | miR-132/miR-411 | 0.79 | 0.49 | 0.64 | 0.84 | 3.20E−02 |
| | miR-323-3p/miR-370 | 0.57 | 0.71 | 0.64 | 0.83 | 4.80E−02 |
| | miR-195/miR-135a + miR-195/miR-99a + miR-382/miR-411 | 1.00 | 0.90 | 0.95 | 0.99 | 1.60E−04 |
| 56-65 vs 66-75 | miR-135a/miR-195 | 0.70 | 0.70 | 0.70 | 0.83 | 1.30E−02 |
| | miR-181a/miR-195 | 0.69 | 0.69 | 0.69 | 0.84 | 1.90E−02 |
| | miR-134/miR-323-3p | 0.69 | 0.62 | 0.66 | 0.80 | 3.30E−02 |
| | miR-874/miR-195 | 0.66 | 0.66 | 0.66 | 0.82 | 3.20E−02 |
| | miR-134/miR-382 | 0.77 | 0.54 | 0.63 | 0.80 | 4.40E−02 |
| | miR-134/miR-323-3p + miR-135a/miR-195 + miR-874/miR-195 | 0.80 | 0.80 | 0.80 | 0.92 | 1.80E−03 |

TABLE 14 miRNA pairs correlating with age in various male and female cohorts

| Gender | Age Groups | miRNA Pairs | Correlation | RSD | P-values |
|---|---|---|---|---|---|
| Male | 26-35 | miR-135a/miR-491-5p | 0.77 | 1.90 | <0.01 |
| | | miR-135a/miR-195 | 0.64 | 2.27 | 0.02 |
| | | miR-411/miR-323-3p | 0.70 | 2.10 | 0.01 |
| | | miR-127/miR-323-3p | 0.71 | 2.08 | 0.01 |
| | | miR-135a/miR-491-5p + miR-135a/miR-195 + miR-411/miR-323-3p + miR-127/miR-323-3p | 0.95 | 0.96 | <0.01 |
| | | miR-127/miR-134 | 0.53 | 1.66 | 0.06 |
| | | miR-382/let-7e | 0.59 | 1.57 | 0.04 |
| | | miR-132/let-7e | 0.53 | 1.65 | 0.06 |
| | | miR-127/miR-134 + miR-382/let-7e + miR-132/let-7e | 0.73 | 1.34 | <0.01 |
| | 46-55 | miR-135a/miR-99a | 0.73 | 2.23 | 0.01 |
| | | miR-323-3p/miR-127 | 0.78 | 2.05 | <0.01 |
| | | miR-181a/miR-411 | 0.73 | 2.24 | <0.01 |
| | | miR-135a/miR-99a + miR-323-3p/miR-127 + miR-181a/miR-411 | 0.93 | 1.24 | <0.01 |
| | 56-65 | miR-182/miR-491-5p | 0.70 | 2.82 | 0.01 |
| | | miR-135a/miR-99a | 0.74 | 2.65 | <0.01 |
| | | miR-182/miR-491-5p + miR-135a/miR-99a | 0.73 | 1.95 | <0.01 |
| | 66-75 | miR-874/miR-491-5p | 0.68 | 2.08 | 0.02 |
| | | miR-874/miR-132 | 0.92 | 1.57 | <0.01 |
| | | miR-127/miR-433 | 0.67 | 2.11 | 0.02 |

TABLE 14-continued miRNA pairs correlating with age in various male and female cohorts

| Gender | Age Groups | miRNA Pairs | Correlation | RSD | P-values |
|---|---|---|---|---|---|
| | | miR-874/miR-132 + miR-874/miR-491-5p + miR-127/miR-433 | 0.84 | 1.53 | <0.01 |
| Female | 26-35 | miR-135a/miR-323-3p | 0.57 | 0.96 | 0.04 |
| | | miR-411/miR-370 | 0.65 | 0.88 | 0.02 |
| | | miR-411/miR-127 | 0.58 | 0.95 | 0.04 |
| | | miR-135a/miR-323-3p + miR-411/miR-370 + miR-411/miR-127 | 0.77 | 0.74 | <0.01 |
| | 36-45 | miR-134/miR-135a | 0.59 | 2.73 | 0.04 |
| | | miR-375/let-7e | 0.61 | 2.70 | 0.03 |
| | | miR-375/miR-135a | 0.60 | 2.70 | 0.03 |
| | | miR-134/miR-135a + miR-375/let-7e + miR-375/miR-135a | 0.91 | 1.42 | <0.01 |
| | 46-55 | miR-182/miR-195 | 0.58 | 2.04 | 0.04 |
| | | miR-433/miR-411 | 0.74 | 1.68 | <0.01 |
| | | let-7e/miR-135a | 0.53 | 2.13 | 0.06 |
| | | miR-182/miR-195 + miR-433/miR-411 + let-7e/miR-135a | 0.85 | 1.34 | <0.01 |
| | 56-65 | miR-323-3p/miR-433 | 0.64 | 1.69 | 0.02 |
| | | miR-382/miR-134 | 0.65 | 1.68 | 0.02 |
| | | miR-132/miR-135a | 0.70 | 1.58 | 0.01 |
| | | miR-323-3p/miR-433 + miR-382/miR-134 + miR-132/miR-135a | 0.93 | 0.79 | <0.01 |
| | 66-75 | miR-132/miR-181a | 0.69 | 2.16 | 0.01 |
| | | miR-127/miR-487b | 0.70 | 2.14 | 0.01 |
| | | miR-132/miR-181a + miR-127/miR-487b | 0.76 | 1.94 | <0.01 |

Conclusions

Experimental data provided herein demonstrate significant sex-dependent differences in plasma concentrations of PG-enriched miRNAs during human life and aging. Changes in plasma concentrations of many PG-enriched miRNAs are more dramatic during menopause in women, which can explain many phenomena described above. For example, pro-apoptotic activity of those miRNAs makes chances of cancer development lower for female compared to male due to more effective elimination of cells with oncogenic mutations. The same miRNAs in brain, where they are secreted, increase chances of AD development for women more significantly than for men because they happen about 10 years earlier. Although plasma concentrations of these PG secreted miRNAs is lower than in brain, their cumulative pro-apoptotic effect increases chances of such aging-related diseases as diabetes 2, sarcopenia, cardiovascular pathologies, etc. Earlier decrease in circulating sex hormones in subjects with Down syndrome explains, at least partially, early development of AD and other apoptosis-associated pathologies but much lower chances of cancer development in those subjects (Nizetic and Groet. Nat. Rev. Cancer, 2012; Castro et al. J. Neurol. 2016; Hithersay et al. Curr. Opin. Psychiatry, 2017). Chr21 location of several miRNA genes expressed in PG is another reason of those effects. Parabiotic effects (rejuvenation due transfer of blood or plasma from young to old animals and aging symptoms after transfusion in opposite direction) can also be explained by effects of circulating miRNAs secreted by PG.

Keeping all these effects in mind the present inventors propose prevention and treatment of aging and aging-associated diseases by regulation of plasma concentrations of circulating miRNAs secreted by PG. Since changes in plasma miRNA concentrations have opposite effects on various organs and organ systems, such treatment should avoid negative consequences of changing circulating miRNA concentrations. To increase concentration of circulating miRNA respective miRNA can be introduced, e.g., in exosomes, other vesicles, complexes with different proteins, nanoparticles, etc. (see, e.g., Nafee and Gouda. Curr. Gene. Ther. 2017). To decrease miRNA concentrations different forms of complementary molecules, such as, e.g., complementary small RNAs, analogues of long non-coding RNA, circular RNAs and peptide bond based ones can be used (see, e.g., Thomson and Dinger, Nat. Rev. Genetics, 2016; Memczak S. Nature, 2013; Ma et al. Bioconjug. Chem. 2014). Due to existence of blood-brain barrier, different miRNAs can be delivered to brain, for example, as a nasal spray (Haney et al. J. Control Release, 2015; Patel and Patel, CNS Drug, 2017) and to circulation (as described above) to avoid negative consequences. Another approach is cell/tissue/organ addressed delivery of miRNAs by, e.g., viral or other vectors for local expression of respective miRNAs. The present analysis of circulating brain-enriched miRNAs clearly demonstrates that in many cases treatment should be not only age- but also sex-specific. It is also important to understand that circulating PG-secreted and other miRNAs do not initiate pathologic processes but increase chances of one or another scenario, e.g., cell survival or apoptotic cell death. Of course, circulating miRNAs affect many other processes increasing or decreasing chances of a pathology.

Other applications of the data described above include: (i) aging and/or treatment monitoring using miRNA pairs correlating with age in various male and female age cohorts; (ii) prediction and/or monitoring of menopause in women; (iii) detection of physiological age versus chronological age based on longitudinal studies of miRNA pairs presented in Table 14, and (iv) improving transgenic animal ND models and/or modeling the menopause by castration or injection of anti-testosterone and/or anti-estradiol compounds.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for monitoring the rate of progression of brain aging in a subject, which method comprises:
   a) measuring the level of two or more numerator miRNAs in two or more bodily fluid samples collected from the subject, wherein the samples have been collected at spaced apart time points;
   b) measuring the level of two or more denominator miRNAs in the same bodily fluids samples as in step (a);
   c) calculating the ratio of the levels of the miRNAs measured in steps (a) and (b) for each bodily fluid sample to produce two or more numerator/denominator miRNA pairs;
   d) calculating a difference in the ratio of the levels of the miRNAs calculated in step (c) between an earlier collected and a later collected bodily fluid samples by subtracting the ratio of the levels of the miRNAs calculated in step (c) for the earlier collected bodily fluid sample from the ratio of the levels of the miRNAs calculated in step (c) for the later collected bodily fluid sample, and e) comparing the difference calculated in step (d) with a corresponding control range of differences for a given sex and age group, wherein
(i) the subject is a 26-35 year old female and miRNA pairs comprise miR-135a/miR-323-3p, miR-411/miR-370, and miR-411/miR-127;
(ii) the subject is a 36-45 year old female and miRNA pairs comprise miR-134/miR-135a, miR-375/let-7e, and miR-375/miR-135a;
(iii) the subject is a 46-55 year old female and miRNA pairs comprise miR-182/miR-195, miR-433/miR-411, and let-7e/miR-135a;
(iv) the subject is a 56-65 year old female and miRNA pairs comprise miR-323-3p/miR-433, miR-382/miR-134, and miR-132/miR-135a;
(v) the subject is a 66-75 year old female and miRNA pairs comprise miR-132/miR-181a; and miR-127/miR-487b;
(vi) the subject is a 26-35 year old male and miRNA pairs comprise miR-135a/miR-491-5p, miR-135a/miR-195, miR-411/miR-323-3p, and miR-127/miR-323-3p;
(vii) the subject is a 36-45 year old male and miRNA pairs comprise miR-127/miR-134, miR-382/let-7e, and miR-132/let-7e;
(viii) the subject is a 46-55 year old male and miRNA pairs comprise miR-135a/miR-99a, miR-323-3p/miR-127, and miR-181a/miR-411;
(ix) the subject is a 56-65 year old male and miRNA pairs comprise miR-182/miR-491-5p and miR-135a/miR-99a;
(x) the subject is a 66-75 year old male and miRNA pairs comprise miR-874/miR-491-5p, miR-874/miR-132, and miR-127/miR-433.

2. The method of claim 1, wherein the subject is a female subject during perimenopause or menopause, or after oophorectomy, or undergoing a sex hormone therapy or anti sex hormone therapy, and wherein miRNA pairs are selected from miR-182/miR-195, miR-433/miR-411, let-7e/miR-135a, miR-323-3p/miR-433, miR-382/miR-134, miR-132/miR-135a, and any combinations thereof.

3. The method of claim 1, wherein the subject is a male subject undergoing a sex hormone therapy or anti sex hormone therapy, and wherein miRNA pairs are selected from miR-182/miR-491-5p, miR-135a/miR-99a, miR-874/miR-491-5p, miR-874/miR-132, miR-127/miR-433, and any combinations thereof.

4. The method of claim 1, wherein the control range of differences for a given sex and age group is a range of values established by determining the ratios of the same miRNAs in a similarly processed bodily fluid in healthy subjects.

5. The method of claim 1, further comprising administering an anti-aging treatment to the subject.

6. The method of claim 5, wherein the anti-aging treatment is selected from diets, exercise regimens, cognitive work, antioxidants, anti-aging drugs, miRNAs, oligonucleotides targeting miRNAs, and any combinations thereof.

7. A method for monitoring the effect of a treatment on progression of brain aging in a subject, which method comprises:
a) measuring the level of two or more numerator miRNAs in a bodily fluid sample collected from the subject prior to initiation of the treatment;
b) measuring the level of two or more denominator miRNAs in the same bodily fluid sample as in step (a);
c) calculating the ratio of the levels of the miRNAs measured in steps (a) and (b) to produce two or more numerator/denominator miRNA pairs;
d) measuring the level of the same numerator miRNAs as in step (a) in one or more bodily fluid sample(s) collected from the subject in the course of or following the treatment;
e) measuring the level of the same denominator miRNAs as in step (b) in the same bodily fluid sample(s) as in step (d);
f) calculating the ratio of the levels of the miRNAs measured in steps (d) and (e) for each bodily fluid sample to produce the same numerator/denominator miRNA pairs as in step (c);
g) calculating a difference in the ratios of the levels of the miRNAs calculated in steps (c) and (f) by subtracting the ratio of the levels of the miRNAs calculated in step (f) from the ratio of the levels of the miRNAs calculated in step (c), and optionally comparing the ratios of the levels of the miRNA calculated in step (f) between different samples in step (d), and
h) comparing the difference(s) calculated in step (g) with a corresponding control range of differences for a given sex and age group, and
i) (i) determining that the treatment is effective for slowing brain aging if the difference calculated in step (g) is smaller than or falls within the corresponding control range of differences, or (ii) determining that the treatment is not effective for slowing brain aging if the difference calculated in step (g) is larger than the corresponding control range of differences, wherein
(i) the subject is a 26-35 year old female and miRNA pairs comprise miR-135a/miR-323-3p, miR-411/miR-370, and miR-411/miR-127;
(ii) the subject is a 36-45 year old female and miRNA pairs comprise miR-134/miR-135a, miR-375/let-7e, and miR-375/miR-135a;
(iii) the subject is a 46-55 year old female and miRNA pairs comprise miR-182/miR-195, miR-433/miR-411, and let-7e/miR-135a;
(iv) the subject is a 56-65 year old female and miRNA pairs comprise miR-323-3p/miR-433, miR-382/miR-134, and miR-132/miR-135a;
(v) the subject is a 66-75 year old female and miRNA pairs comprise miR-132/miR-181a; and miR-127/miR-487b;
(vi) the subject is a 26-35 year old male and miRNA pairs comprise miR-135a/miR-491-5p, miR-135a/miR-195, miR-411/miR-323-3p, and miR-127/miR-323-3p;
(vii) the subject is a 36-45 year old male and miRNA pairs comprise miR-127/miR-134, miR-382/let-7e, and miR-132/let-7e;
(viii) the subject is a 46-55 year old male and miRNA pairs comprise miR-135a/miR-99a, miR-323-3p/miR-127, and miR-181a/miR-411;
(ix) the subject is a 56-65 year old male and miRNA pairs comprise miR-182/miR-491-5p and miR-135a/miR-99a;
(x) the subject is a 66-75 year old male and miRNA pairs comprise miR-874/miR-491-5p, miR-874/miR-132, and miR-127/miR-433.

8. The method of claim 7, wherein the subject is a female subject during perimenopause or menopause, or after oophorectomy.

9. The method of claim 7, wherein the subject is a female or male subject undergoing a sex hormone therapy or anti sex hormone therapy.

10. The method of claim 7, wherein the control range of differences for a given sex and age group is a range of values established by determining the ratios of the same miRNAs in a similarly processed bodily fluid in healthy subjects.

11. The method of claim 7, wherein the method comprises administering the treatment to the subject.

12. The method of claim 1, wherein the bodily fluid is selected from the group consisting of blood plasma, serum, urine, and saliva.

13. The method of claim 1, wherein the method further comprises the step of collecting the bodily fluid sample(s) from the subject.

14. The method of claim 1, wherein the level of the miRNAs is determined using a method selected from the group consisting of hybridization, polymerase chain reaction (PCR)-based detection, sequencing, and microfluidic technologies.

15. The method of claim 1, wherein prior to measuring miRNA level, the miRNA is isolated and purified from the bodily fluid sample.

16. The method of claim 1, wherein the method further comprises reducing or eliminating degradation of the miRNAs.

17. The method of claim 1, further comprising:
f) (i) determining that the brain aging in the subject has progressed at a higher than normal rate if the difference calculated in step (d) is larger than the corresponding control range of differences, or (ii) determining that the brain aging in the subject has progressed at a normal rate if the difference calculated in step (d) falls within the corresponding control range of differences, or (iii) determining that the brain aging in the subject has progressed at a lower than normal rate if the difference calculated in step (d) is smaller than the corresponding control range of differences.

18. A method for monitoring the effect of a treatment on progression of brain aging in a subject, which method comprises conducting steps (a)-(e) of the method of claim 1, wherein the earlier collected bodily fluid samples are collected from the subject prior to initiation of the treatment and the later collected bodily fluid samples are collected from the subject in the course of or following the treatment, said method further comprising:
f) comparing the difference(s) calculated in step (d) with a corresponding control range of differences for a given sex and age group, and
g) (i) determining that the treatment is effective for slowing brain aging if the difference calculated in step (d) is smaller than or falls within the corresponding control range of differences, or (ii) determining that the treatment is not effective for slowing brain aging if the difference calculated in step (d) is larger than the corresponding control range of differences.

* * * * *